United States Patent
Youngblood et al.

(10) Patent No.: US 12,318,214 B2
(45) Date of Patent: Jun. 3, 2025

(54) STRESS REDUCTION AND SLEEP PROMOTION SYSTEM

(71) Applicant: Sleep Solutions Inc., Wilmington, DE (US)

(72) Inventors: Todd Youngblood, Mooresville, NC (US); Tara Youngblood, Mooresville, NC (US)

(73) Assignee: SLEEP SOLUTIONS INC, Wilmington, DE (US)

( * ) Notice: Subject to any disclaimer, the term of this patent is extended or adjusted under 35 U.S.C. 154(b) by 0 days.

(21) Appl. No.: 18/495,943

(22) Filed: Oct. 27, 2023

(65) Prior Publication Data

US 2024/0050029 A1    Feb. 15, 2024

Related U.S. Application Data

(63) Continuation of application No. 16/686,394, filed on Nov. 18, 2019, now Pat. No. 11,813,076, which is a continuation-in-part of application No. 15/848,816, filed on Dec. 20, 2017, now Pat. No. 11,013,883, which is a continuation-in-part of application No. 15/705,829, filed on Sep. 15, 2017, now Pat. No.

(Continued)

(51) Int. Cl.
| | |
|---|---|
| *A61B 5/00* | (2006.01) |
| *A61B 5/0205* | (2006.01) |
| *A61B 5/11* | (2006.01) |
| *A61B 5/389* | (2021.01) |
| *A61M 21/00* | (2006.01) |

(52) U.S. Cl.
CPC ........ *A61B 5/4812* (2013.01); *A61B 5/02055* (2013.01); *A61B 5/1118* (2013.01); *A61B 5/389* (2021.01); *A61B 5/4815* (2013.01); *A61B 5/4884* (2013.01); *A61B 5/681* (2013.01); *A61M 2021/0066* (2013.01)

(58) Field of Classification Search
CPC ... A61B 5/4812; A61B 5/02055; A61B 5/118; A61B 5/4815; A61B 5/4884; A61B 5/681
See application file for complete search history.

(56) References Cited

U.S. PATENT DOCUMENTS

| | | |
|---|---|---|
| 2,753,435 A | 7/1956 | Ivar |
| 3,230,556 A | 1/1966 | Wiusor |

(Continued)

FOREIGN PATENT DOCUMENTS

| | | |
|---|---|---|
| KR | 20060019762 A | 3/2006 |
| KR | 20110102637 A | 9/2011 |
| WO | 2014145436 A1 | 9/2014 |

OTHER PUBLICATIONS

Buysse, D.J., Reynolds, C.F., Monk, T.H., Berman, S.R., & Kupfer, D.J. (1989). The Pittsburgh Sleep Quality Index (PSQI): A new instrument for psychiatric research and practice. Psychiatry Research, 28(2), 193-213.

(Continued)

*Primary Examiner* — Nael N Babaa
(74) *Attorney, Agent, or Firm* — Vadim Savyateev; Legal Counsel PC

(57) ABSTRACT

The present invention provides systems, methods, and articles for stress reduction and sleep promotion. A stress reduction and sleep promotion system includes at least one remote device, at least one body sensor, and at least one remote server. In other embodiments, the stress reduction and sleep promotion system includes machine learning.

16 Claims, 41 Drawing Sheets

Related U.S. Application Data 10,986,933, which is a continuation-in-part of application No. 14/777,050, filed as application No. PCT/US2014/030202 on Mar. 17, 2014, now Pat. No. 10,278,511.

(60) Provisional application No. 62/398,257, filed on Sep. 22, 2016, provisional application No. 61/800,768, filed on Mar. 15, 2013, provisional application No. 62/769,183, filed on Nov. 19, 2018.

(56) References Cited

U.S. PATENT DOCUMENTS

| | | |
|---|---|---|
| 4,132,262 A | 1/1979 | Wibell |
| 4,459,468 A | 7/1984 | Bailey |
| 4,777,802 A | 10/1988 | Feher |
| 4,858,609 A | 8/1989 | Cole |
| 5,033,136 A | 7/1991 | Elkins |
| 5,304,112 A | 4/1994 | Mrklas et al. |
| 5,329,096 A | 7/1994 | Suematsu |
| 5,448,788 A | 9/1995 | Wu |
| 5,894,615 A | 4/1999 | Alexander |
| 5,948,303 A | 9/1999 | Larson |
| 6,163,907 A | 12/2000 | Larson |
| 6,273,810 B1 | 8/2001 | Rhodes, Jr. et al. |
| 6,371,976 B1 | 4/2002 | Vrzalik et al. |
| 6,463,743 B1 | 10/2002 | Laliberté |
| 6,484,062 B1 | 11/2002 | Kim |
| 6,581,224 B2 | 6/2003 | Yoon |
| 6,826,792 B2 | 12/2004 | Lin |
| 7,041,049 B1 | 5/2006 | Raniere |
| 7,238,289 B2 | 7/2007 | Suddath |
| 7,248,915 B2 | 7/2007 | Rönnholm |
| 7,306,567 B2 | 12/2007 | Loree |
| 7,382,047 B2 | 6/2008 | Chen et al. |
| 7,460,899 B2 | 12/2008 | Almen |
| 7,524,279 B2 | 4/2009 | Auphan |
| 7,546,653 B2 | 6/2009 | Ye |
| 7,608,041 B2 | 10/2009 | Sutton |
| 7,699,785 B2 | 4/2010 | Nemoto |
| 7,868,757 B2 | 1/2011 | Radivojevic et al. |
| 7,908,687 B2 | 3/2011 | Ward et al. |
| 8,096,960 B2 | 1/2012 | Loree et al. |
| 8,179,270 B2 | 5/2012 | Rai et al. |
| 8,191,187 B2 | 6/2012 | Brykalski et al. |
| 8,290,596 B2 | 10/2012 | Wei et al. |
| 8,348,840 B2 | 1/2013 | Heit et al. |
| 8,418,285 B2 | 4/2013 | Frias |
| 8,529,457 B2 | 9/2013 | Devot et al. |
| 8,617,044 B2 | 12/2013 | Pelgrim et al. |
| 8,768,520 B2 | 7/2014 | Oexman et al. |
| 8,979,730 B2 | 3/2015 | Naujokat et al. |
| 9,044,101 B2 | 6/2015 | Garcia et al. |
| 9,186,479 B1 | 11/2015 | Franceschetti et al. |
| 9,196,479 B1 | 11/2015 | Cheng et al. |
| 9,402,763 B2 | 8/2016 | Bledsoe |
| 9,459,597 B2 | 10/2016 | Kahn et al. |
| 9,750,415 B2 | 9/2017 | Breslow et al. |
| 9,981,107 B2 | 5/2018 | Franceschetti et al. |
| 9,993,195 B2 | 6/2018 | Van Vugt et al. |
| 9,999,744 B2 | 6/2018 | Proud |
| 10,154,932 B2 | 12/2018 | Franceschetti et al. |
| 10,179,064 B2 | 1/2019 | Connor |
| 10,188,222 B2 | 1/2019 | Veron |
| 10,216,485 B2 | 2/2019 | Misra et al. |
| 10,350,108 B1 | 7/2019 | Rittman, III et al. |
| 10,391,009 B2 | 8/2019 | Bhai |
| 10,398,357 B2 | 9/2019 | Chen et al. |
| 10,401,807 B2 | 9/2019 | Jo et al. |
| 10,675,434 B2 | 6/2020 | Van Driel et al. |
| 10,686,626 B2 | 6/2020 | Sarwar et al. |
| 10,709,335 B2 | 7/2020 | Matsuoka et al. |
| 10,764,079 B2 | 9/2020 | Mahar et al. |
| 10,764,374 B1 | 9/2020 | Marquardt et al. |
| 10,824,634 B2 | 11/2020 | Siebel et al. |
| 10,833,888 B2 | 11/2020 | Kim et al. |
| 10,923,226 B2 | 2/2021 | Macary et al. |
| 10,959,667 B2 | 3/2021 | Xin et al. |
| 10,971,261 B2 | 4/2021 | Kahn et al. |
| 11,040,169 B2 | 6/2021 | Jung et al. |
| 11,097,079 B2 | 8/2021 | Shanmugam et al. |
| 11,134,888 B2 | 10/2021 | Wright et al. |
| 11,185,281 B2 | 11/2021 | Molina et al. |
| 2002/0014951 A1 | 2/2002 | Kramer et al. |
| 2002/0080035 A1 | 6/2002 | Youdenko |
| 2002/0124574 A1 | 9/2002 | Guttman et al. |
| 2004/0049132 A1 | 3/2004 | Barron et al. |
| 2005/0143617 A1 | 6/2005 | Auphan |
| 2005/0154330 A1 | 7/2005 | Loree |
| 2006/0137099 A1 | 6/2006 | Feher |
| 2006/0293602 A1 | 12/2006 | Clark |
| 2006/0293608 A1 | 12/2006 | Rothman et al. |
| 2007/0234741 A1 | 10/2007 | Lee et al. |
| 2008/0016881 A1 | 1/2008 | Steffensen et al. |
| 2008/0234785 A1 | 9/2008 | Nakayama et al. |
| 2009/0112069 A1 | 4/2009 | Kanamori et al. |
| 2009/0121826 A1 | 5/2009 | Song et al. |
| 2009/0288800 A1 | 11/2009 | Kang et al. |
| 2010/0011502 A1 | 1/2010 | Brykalski et al. |
| 2010/0100004 A1 | 4/2010 | van Someren |
| 2010/0174198 A1 | 7/2010 | Young et al. |
| 2010/0197996 A1 | 8/2010 | Cornel |
| 2010/0199687 A1 | 8/2010 | Woods et al. |
| 2010/0293715 A1 | 11/2010 | Sakamoto et al. |
| 2010/0324611 A1 | 12/2010 | Deming et al. |
| 2011/0015327 A1 | 1/2011 | Bichler et al. |
| 2011/0015495 A1 | 1/2011 | Dothie et al. |
| 2011/0073292 A1 | 3/2011 | Datta et al. |
| 2011/0107514 A1 | 5/2011 | Brykalski et al. |
| 2011/0153274 A1 | 6/2011 | Ho et al. |
| 2011/0181597 A1 | 7/2011 | Cardno et al. |
| 2011/0230790 A1 | 9/2011 | Kozlov |
| 2011/0247139 A1 | 10/2011 | Tallent et al. |
| 2011/0252461 A1 | 10/2011 | Wetzer et al. |
| 2011/0267196 A1 | 11/2011 | Hu et al. |
| 2012/0054754 A1 | 3/2012 | Teichmann et al. |
| 2012/0136666 A1 | 5/2012 | Corpier et al. |
| 2012/0159968 A1 | 6/2012 | Doucet et al. |
| 2012/0296402 A1 | 11/2012 | Kotter |
| 2013/0019611 A1 | 1/2013 | Sims et al. |
| 2013/0060306 A1 | 3/2013 | Colbauch |
| 2013/0208576 A1 | 8/2013 | Loree, IV et al. |
| 2013/0234823 A1 | 9/2013 | Kahn et al. |
| 2013/0304768 A1 | 11/2013 | Basnight et al. |
| 2014/0006001 A1 | 1/2014 | Kamhi et al. |
| 2014/0208508 A1 | 7/2014 | Mikesell |
| 2014/0277308 A1 | 9/2014 | Cronise et al. |
| 2014/0316495 A1 | 10/2014 | Augustine et al. |
| 2015/0093101 A1 | 4/2015 | Lee |
| 2015/0203068 A1 | 7/2015 | Foo et al. |
| 2015/0257697 A1 | 9/2015 | Sepah |
| 2015/0289666 A1 | 10/2015 | Chandler et al. |
| 2015/0351982 A1 | 12/2015 | Krenik |
| 2015/0366703 A1 | 12/2015 | Du |
| 2016/0015184 A1 | 1/2016 | Nunn et al. |
| 2016/0015315 A1 | 1/2016 | Auphan et al. |
| 2016/0029808 A1 | 2/2016 | Youngblood et al. |
| 2016/0136385 A1 | 5/2016 | Scorcioni |
| 2016/0151603 A1 | 6/2016 | Shouldice et al. |
| 2016/0235610 A1 | 8/2016 | Drake |
| 2016/0239624 A1 | 8/2016 | Short et al. |
| 2016/0249842 A1 | 9/2016 | Lubelchick |
| 2016/0310697 A1 | 10/2016 | Franceschetti et al. |
| 2017/0003666 A1 | 1/2017 | Nunn et al. |
| 2017/0017759 A1 | 1/2017 | MacNeice et al. |
| 2017/0053068 A1 | 2/2017 | Pillai et al. |
| 2017/0095196 A1 | 4/2017 | Oakhill |
| 2017/0138663 A1 | 5/2017 | Wells |
| 2017/0189641 A1 | 7/2017 | Moturu et al. |
| 2017/0231812 A1 | 8/2017 | Boyden et al. |
| 2018/0000255 A1 | 1/2018 | Youngblood et al. |
| 2018/0082550 A1 | 3/2018 | Read et al. |
| 2018/0110960 A1 | 4/2018 | Youngblood et al. |
| 2018/0203744 A1 | 7/2018 | Wiesmaier et al. |

(56) References Cited

U.S. PATENT DOCUMENTS

| | | |
|---|---|---|
| 2018/0226155 A1 | 8/2018 | Mahoney et al. |
| 2018/0260387 A1 | 9/2018 | Ben-Kiki et al. |
| 2018/0285528 A1 | 10/2018 | Healey et al. |
| 2018/0325450 A1 | 11/2018 | Huang |
| 2018/0344517 A1 | 12/2018 | Nofzinger |
| 2019/0099009 A1 | 4/2019 | Connor |
| 2019/0203983 A1 | 7/2019 | Jeon et al. |
| 2019/0209405 A1 | 7/2019 | Sayadi et al. |
| 2019/0231081 A1 | 8/2019 | Youngblood et al. |
| 2019/0265971 A1 | 8/2019 | Behzadi et al. |
| 2019/0349254 A1 | 11/2019 | Nolan et al. |
| 2020/0027552 A1 | 1/2020 | Lee |
| 2020/0046134 A1 | 2/2020 | Youngblood et al. |
| 2020/0077942 A1 | 3/2020 | Youngblood et al. |
| 2020/0100682 A1 | 4/2020 | Abreu et al. |
| 2020/0113344 A1 | 4/2020 | Youngblood et al. |
| 2020/0171268 A1 | 6/2020 | Zhang |
| 2020/0178887 A1 | 6/2020 | Ramírez et al. |
| 2020/0205727 A1 | 7/2020 | Shen et al. |
| 2020/0215295 A1 | 7/2020 | LaPorte et al. |
| 2020/0229967 A1 | 7/2020 | Drew |
| 2020/0236907 A1 | 7/2020 | Nilsson et al. |
| 2020/0281521 A1 | 9/2020 | Cail |
| 2020/0289052 A1 | 9/2020 | Gross |
| 2020/0315368 A1 | 10/2020 | Tsern et al. |
| 2020/0337470 A1 | 10/2020 | Sayadi et al. |
| 2020/0397379 A1 | 12/2020 | Franceschetti et al. |
| 2021/0031000 A1 | 2/2021 | Lee et al. |
| 2021/0146091 A1 | 5/2021 | Kansagra |
| 2021/0178113 A1 | 6/2021 | Bresch et al. |
| 2021/0267379 A1 | 9/2021 | Youngblood et al. |
| 2021/0267380 A1 | 9/2021 | Stusynski |
| 2021/0314405 A1 | 10/2021 | Demirli et al. |
| 2022/0134050 A1 | 5/2022 | Moriyasu |
| 2022/0339398 A1 | 10/2022 | Youngblood et al. |

OTHER PUBLICATIONS

Quan, S. F. et. al; "Healthy Sleep the Characteristics of Sleep" (Sep. 21, 2016) pp. 1-4, retrieved from http://healthysleep.med.harvard.edu/healthy/science/what/characteristics.

Tobaldini, E. et. al; "Heart rate variability in normal and pathological sleep", Frontiers in Physiology, (Oct. 16, 2013), p. 1-11, vol. 4, Article 294, doi: 10.3389/fphys.2013.00294.

U.S. Appl. No. 61/800,768 Youngblood,Thermo electric heating and cooling device, filed Mar. 15, 2013, drawings and specification.

U.S. Appl. No. 62/398,257, Youngblood,Bed Pad With Custom Modulated Temperature Adjustment , filed Sep. 22, 2016, Drawings and Specification.

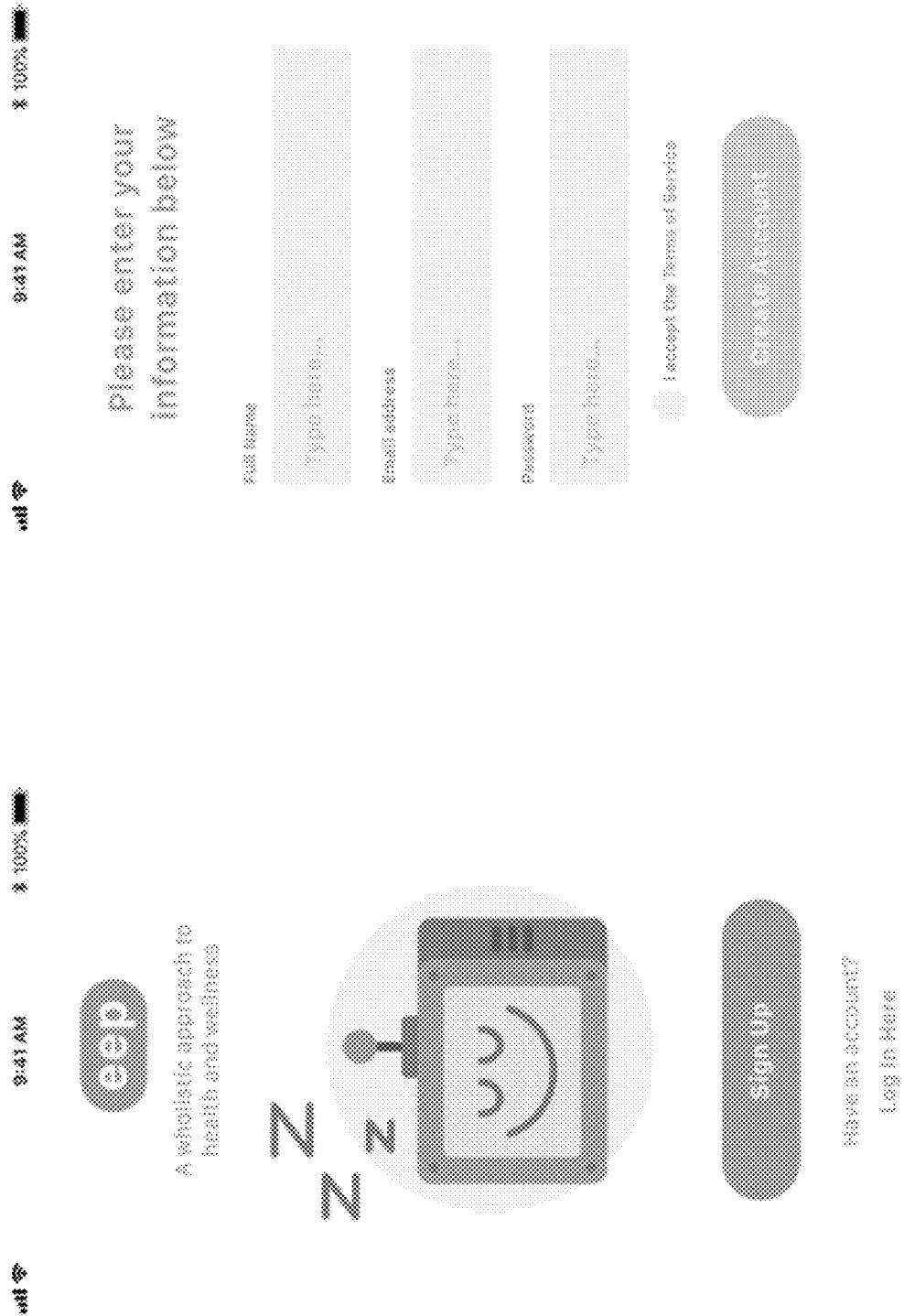

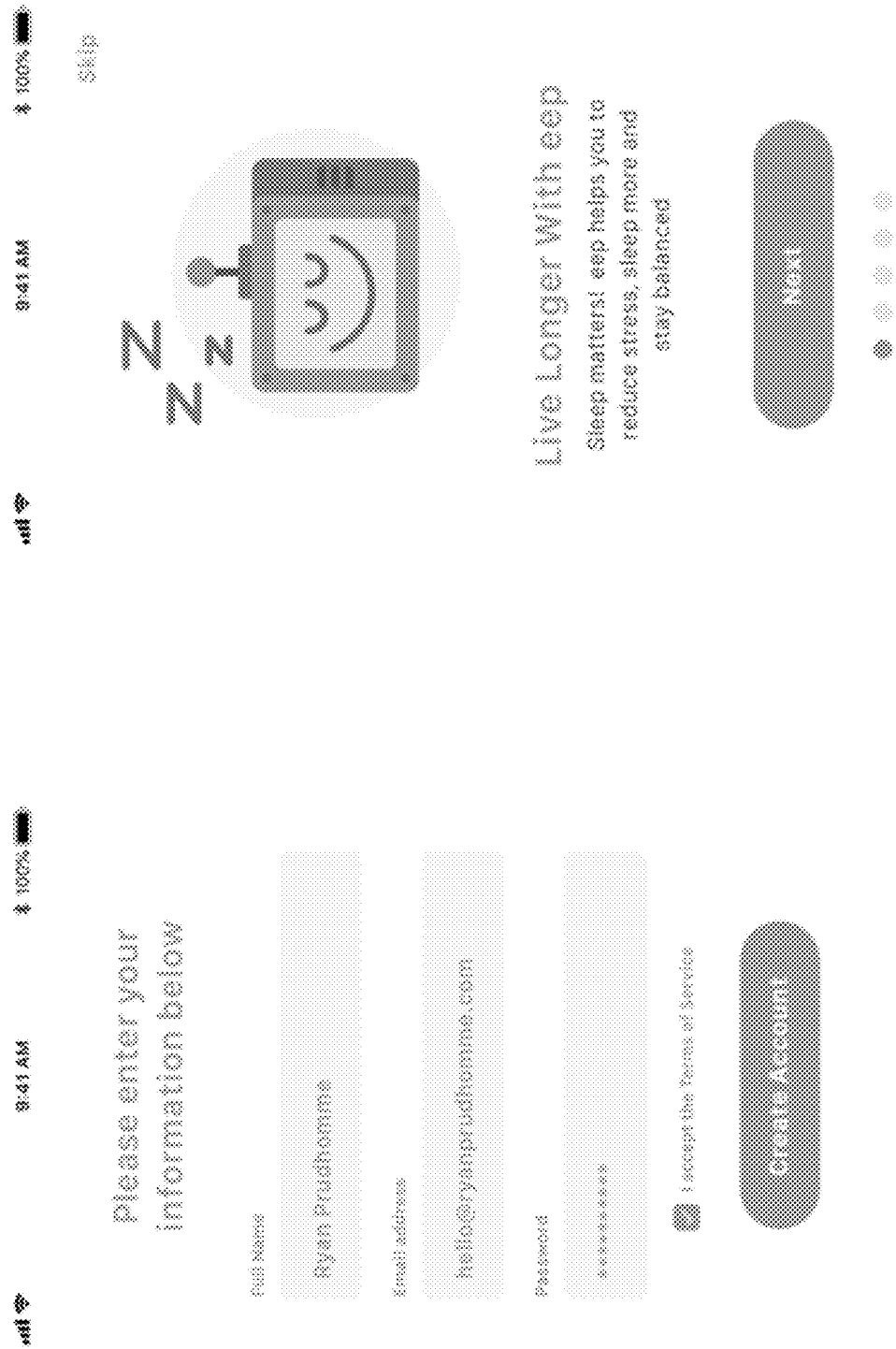

Chronotype Quiz

1. You have to do two hours of physically hard work. If you were entirely free to plan your day, in which of the following periods would you choose to do the work?
    a. 8:00 a.m. – 10:00 a.m. (4 points)
    b. 11:00 a.m. – 1:00 p.m. (3 points)
    c. 3:00 p.m. – 5:00 p.m. (2 points)
    d. 7:00 p.m. – 9:00 p.m. (1 point)
2. You have to take a two-hour test. You know it will be mentally exhausting. If you were entirely free to choose, when would you choose to take the test?
    a. 8:00 a.m. – 10:00 a.m. (4 points)
    b. 11:00 a.m. – 1:00 p.m. (3 points)
    c. 3:00 p.m. – 5:00 p.m. (2 points)
    d. 7:00 p.m. – 9:00 p.m. (1 point)
3. A friend has asked you to join him twice per week for a workout. The best time for him is between 10 p.m. and 11 p.m. With nothing else in mind other than how you normally feel in the evening, how do you think you would perform?
    a. Very poorly (4 points)
    b. Poorly (3 points)
    c. Well enough (2 points)
    d. Very well (1 point)
4. We hear about "morning" and "evening" types of people. Which of these types do you consider yourself?
    a. Definitely morning type (6 points)
    b. More a morning than an evening type (4 points)
    c. More an evening than a morning type (2 points)
    d. Definitely an evening type (0 points)

Add your scores together to get your total and compare your score with the table below to identify your chronotype.

| Points | Type |
|---|---|
| 14-16 | Morning person |
| 11-13 | Less morning person |
| 9-10 | Neither morning person nor night owl |
| 4-8 | Less night owl |
| 0-3 | Night owl |

FIG. 66

| User | Chronotype | Diet | Fitness | Intervention | Influencer | Coach |
|---|---|---|---|---|---|---|
| User 1 | Morning Person | WHOLE30 | Yoga, Swimming | Meditation, Journaling | Influencer 1, Influencer 2 | N/A |
| User 2 | Night Owl | Keto | Weights, Running | Journaling | Influencer 3 | N/A |
| User 3 | Neither Morning or Night Owl | Paleo | Cycling | Breathing Exercises | N/A | Coach 1 |
| User 4 | Less Night Owl | Fasting | Running | Tiny Habits | Influencer 4, Influencer 5 | Coach 2 |
| User 5 | Less Morning Person | Keto | Kickboxing | Meditation | Influencer 1, Influencer 4 | Coach 3 |
| User 6 | Morning Person | Vegan | Yoga | Meditation, Breathing Exercises | Influencer 2, Influencer 5 | Coach 2 |

FIG. 69

STRESS REDUCTION AND SLEEP PROMOTION SYSTEM

CROSS REFERENCE TO RELATED APPLICATIONS

This application relates to and claims priority from the following applications. This application is a continuation of U.S. patent application Ser. No. 16/686,394, filed Nov. 18, 2019, which claims the benefit of U.S. Provisional Patent Application No. 62/769,183, filed Nov. 19, 2018. U.S. patent application Ser. No. 16/686,394 is a continuation-in-part of U.S. patent application Ser. No. 15/848,816, filed Dec. 20, 2017. U.S. patent application Ser. No. 15/848,816 is a continuation-in-part of U.S. application Ser. No. 15/705,829, filed Sep. 15, 2017, which is a continuation-in-part of U.S. application Ser. No. 14/777,050, filed Sep. 15, 2015, which is the National Stage of International Application No. PCT/US2014/030202, filed Mar. 17, 2014, which claims the benefit of U.S. Provisional Application No. 61/800,768, filed Mar. 15, 2013. U.S. application Ser. No. 15/705,829 also claims the benefit of U.S. Provisional Application No. 62/398,257, filed Sep. 22, 2016. Each of the above applications is incorporated herein by reference in its entirety.

BACKGROUND OF THE INVENTION

1. Field of the Invention

This invention relates broadly and generally to articles, methods, and systems for stress reduction and sleep promotion.

2. Description of the Prior Art

Several studies show that stress can negatively impact health by causing diseases or exacerbating existing conditions. Stress impacts the individual on a physiological and psychological level. Further, stress may lead individuals to adopt health damaging behaviors (e.g., smoking, drinking, poor nutrition, lack of physical activity). These physiological changes and health damaging behaviors can cause illnesses, such as sleep disturbances, impaired wound healing, increased infections, heart disease, diabetes, ulcers, pain, depression, and obesity or weight gain.

Therefore, it is important to manage and treat stress to maintain health. However, many individuals are under increased pressure due to a modern lifestyle, which leaves less time for relaxation and sleep. This lack of stress relief and sleep results in an increase in both mental and physical stress.

Various methods of stress relief are known, including exercise, biofeedback, and meditation. These systems often include a physical device that stimulates the body and/or senses. These systems may also shield the user from outside interferences.

Prior art patent documents include the following:

U.S. Pat. No. 5,304,112 for stress reduction system and method by inventors Mrklas et al., filed Oct. 16, 1991 and issued Apr. 19, 1994, is directed to an integrated stress reduction system that detects the stress level of a subject and displays a light pattern reflecting the relationship between the subject's stress level and a target level. At the same time, the system provides relaxing visual, sound, tactile, environmental, and other effects to aid the subject in reducing his or her stress level to the target level. In one preferred embodiment, the intensity, type, and duration of the relaxing effects are controlled by a computer program in response to the measured stress level. The light pattern stress level display uses a laser which is deflected on one axis by a measured stress level signal and on a second axis perpendicular to the first by a target signal representing the target stress level. The pattern produced is more complex when the two signals do not coincide, and becomes a less complex geometric figure as the subject's stress level approaches the target.

U.S. Pat. No. 6,484,062 for computer system for stress relaxation and operating method of the same by inventor Kim, filed Nov. 30, 1999 and issued Nov. 19, 2002, is directed to a computer system provided to relax stresses such as fatigue, VDT syndrome, occupational diseases or psychogenic possibly gained from long hours of computer usage. This new computer system is able to divert the negative effects of conventional computer to affirmative effects by introducing the aroma therapy. The new computer system provides not only the data programs of establishing, playing execution and controlling, but also the stress relief program comprising acoustic therapy, color therapy, fragrance therapy and tactual therapy and a stress perception program. The stress relief program is operated by an emission device through a converter. The equipment of the stress relief is installed on a peripheral device of computer such as a speaker, keyboard or monitor. The new concept of computer system for stress relaxation originates a combination of the computer system and the natural therapies applied the human senses like sight, hearing, feeling and smelling senses. With this new computer system, the computer user has a merit of stress relief during the computer operating.

U.S. Publication No. 20040049132 for device for body activity detection and processing by inventors Barron et al., filed Dec. 9, 2002 and published Mar. 11, 2004, is directed to a method and device for monitoring a body activity. The device has an actimetry sensor for measuring the activity and storage means for receiving data from the actimetry sensor. The data are analysed according to a method using summation algorithm, where a plurality of parameters relating to the activity are summed to provide advisory information relating to that activity. The analysis may include pre-programmed biasing constants or user supplied biasing constants.

U.S. Pat. No. 7,460,899 for apparatus and method for monitoring heart rate variability by inventor Almen, filed Feb. 25, 2005 and issued Dec. 2, 2008, is directed to a wrist-worn or arm band worn heart rate variability monitor. Heart rate variability ("HRV") refers to the variability of the time interval between heartbeats and is a reflection of an individual's current health status. Over time, an individual may use the results of HRV tests to monitor either improvement or deterioration of specific health issues. Thus, one use of the HRV test is as a medical motivator. When an individual has a poor HRV result, it is an indicator that they should consult their physician and make appropriate changes where applicable to improve their health. If an individual's HRV results deviate significantly from their normal HRV, they may be motivated to consult their physician. In addition, the inventive monitor is capable of monitoring the stages of sleep by changes in the heart rate variability and can record the sleep (or rest) sessions with the resulting data accessible by the user or other interested parties. Alternate embodiments of the invention allow assistance in the diagnosis and monitoring of various cardiovascular and sleep breathing disorders and/or conditions. Other embodiments allow communication with internal devices such as defibrillators or drug delivery mechanisms. Still other embodiments analyze HRV data to assist the user in avoiding sleep.

U.S. Pat. No. 7,524,279 for sleep and environment control method and system by inventor Auphan, filed Dec. 29, 2004 and issued Apr. 28, 2009, is directed to a sleep system that includes sensors capable of gathering sleep data from a person and environmental data during a sleep by the person. A processor executes instructions that analyze this data and control the sleep of the person and the environment surrounding the person. Typically, the instructions are loaded in a memory where they execute to generate an objective measure of sleep quality from the sleep data from the person and gather environmental data during the sleep by the person. Upon execution, the instructions receive a subjective measure of sleep quality from the person after the sleep, create a sleep quality index from the objective measure of sleep quality and subjective measure of sleep quality, correlate the sleep quality index and a current sleep system settings with a historical sleep quality index and corresponding historical sleep system settings. The instructions then may modify the current set of sleep system settings depending on the correlation between the sleep quality index and the historic sleep quality index. These sleep system settings control and potentially change one or more different elements of an environment associated with the sleep system.

U.S. Pat. No. 7,699,785 for method for determining sleep stages by inventor Nemoto, filed Feb. 23, 2005 and issued Apr. 20, 2010, is directed to a method for determining sleep stages of an examinee, including detecting signals of the examinee with a biosignal detector, calculating a signal strength deviation value that indicates deviation of a signal strength of the detected signals, and determining a sleep stage by using the signal strength deviation value or a value of a plurality of values based on the signal strength deviation value as an indicator value.

U.S. Publication No. 20100100004 for skin temperature measurement in monitoring and control of sleep and alertness by inventor van Someren, filed Dec. 15, 2008 and published Apr. 22, 2010, is directed to a method of an arrangement for monitoring sleep in a subject by measuring within a prescribed interval skin temperature of a predetermined region of the subject's body and a motion sensor for sensing motion of the subject, comparing the measured skin temperature of the predetermined region with a predetermined temperature threshold, and classifying the subject as being asleep or awake based on whether the skin temperature of the predetermined region is above or below the temperature threshold and on the motion data. In alternative aspects the invention relates to methods of and arrangements for manipulating sleep, as well as monitoring or manipulating alertness.

U.S. Pat. No. 7,868,757 for method for the monitoring of sleep using an electronic device by inventors Radivojevic et al., filed Dec. 29, 2006 and issued Jan. 11, 2011, is directed to a method where sleep sensor signals are obtained to a mobile communication device from sensor devices. The mobile communication device checks the sleep sensor signals for a sleep state transition, determines the type of the sleep state transition, forms control signals based on the type of the sleep state transition and sends the control signals to at least one electronic device.

U.S. Publication No. 20110015495 for method and system for managing a user's sleep by inventors Dothie et al., filed Jul. 16, 2010 and published Jan. 20, 2011, is directed to a sleep management method and system for improving the quality of sleep of a user which monitors one or more objective parameters relevant to sleep quality of the user when in bed and receives from the user in waking hours via a portable device such as a mobile phone feedback from objective test data on cognitive and/or psychomotor performance.

U.S. Publication No. 20110267196 for system and method for providing sleep quality feedback by inventors Hu et al., filed May 3, 2011 and published Nov. 3, 2011, is directed to a system and method for providing sleep quality feedback that includes receiving alarm input on a base device from a user; the base device communicating an alarm setting based on the alarm input to an individual sleep device; the individual sleep device collecting sleep data based on activity input of a user; the individual sleep device communicating sleep data to the base device; the base device calculating sleep quality feedback from the sleep data; communicating sleep quality feedback to a user; and the individual sleep device activating an alarm, wherein activating the alarm includes generating tactile feedback to the user according to the alarm setting.

U.S. Pat. No. 8,290,596 for therapy program selection based on patient state by inventors Wei et al., filed Sep. 25, 2008 and issued Oct. 16, 2012, is directed to selecting a therapy program based on a patient state, where the patient state comprises at least one of a movement state, sleep state or speech state. In this way, therapy delivery is tailored to the patient state, which may include specific patient symptoms. The therapy program is selected from a plurality of stored therapy programs that comprise therapy programs associated with a respective one at least two of the movement, sleep, and speech states. Techniques for determining a patient state include receiving volitional patient input or detecting biosignals generated within the patient's brain. The biosignals are nonsymptomatic and may be incidental to the movement, sleep, and speech states or generated in response to volitional patient input.

U.S. Pat. No. 8,348,840 for device and method to monitor, assess and improve quality of sleep by inventors Heit et al., filed Feb. 4, 2010 and issued Jan. 8, 2013, is directed to a medical sleep disorder arrangement that integrates into current diagnosis and treatment procedures to enable a health care professional to diagnose and treat a plurality of subjects suffering from insomnia. The arrangement may include both environmental sensors and body-worn sensors that measure the environmental conditions and the condition of the individual patient. The data may be collected and processed to measure clinically relevant attributes of sleep quality automatically. These automatically determined measures, along with the original sensor data, may be aggregated and shared remotely with the health care professional. A communication apparatus enables the healthcare professional to remotely communicate with and further assess the patient and subsequently administer the treatment. Thus, a more accurate diagnosis and more effective treatment is provided while reducing the required clinician time per patient for treatment delivery.

U.S. Pat. No. 8,529,457 for system and kit for stress and relaxation management by inventors Devot et al., filed Aug. 20, 2010 and issued Sep. 10, 2013, is directed to a system and a kit for stress and relaxation management. A cardiac activity sensor is used for measuring the heart rate variability (HRV) signal of the user and a respiration sensor for measuring the respiratory signal of the user. The system contains a user interaction device having an input unit for receiving user specific data and an output unit for providing information output to the user. A processor is used to assess the stress level of the user by determining a user related stress index. The processor is also used to monitor the user during a relaxation exercise by means of determining a relaxation index based on the measured HRV and respiratory signals, the relaxation index being continuously adapted to the incoming measured signals and based thereon the processor instructs the output unit to provide the user with biofeedback and support messages. Finally, the processor uses the user specific data as an input in generating a first set of rules defining an improvement plan for self-management of stress and relaxation. The first set of rules is adapted to trigger commands instructing the output unit to provide the user with motivation related messages. Also, at least a portion of said user specific data is further used to define a second set of rules indicating the user's personal goals.

U.S. Pat. No. 8,617,044 for stress reduction by inventors Pelgrim et al., filed Jun. 5, 2009 and issued Dec. 31, 2013, is directed to a method and system for reducing stress in a working environment. In a conditioning phase a positive association of a sensory stimulus, such as a scent, image and/or sound with a relaxed feeling is created. Following the creation of this positive association the "relaxing" stimulus will be used as a de-stressor in the usage phase. That is, when it is detected that the user is stressed, the "relaxing" stimulus is released to reduce stress.

U.S. Pat. No. 8,979,730 for method and system for providing behavioural therapy for insomnia by inventors Naujokat, et al., filed Jun. 1, 2010 and issued Mar. 17, 2015, is directed to a system and method to provide for the automatic assessment of the presence/severity of the sleep problem and its exact nature. The assessment is based on qualitative information about sleep patterns, insomnia-related factors and daytime consequences, as well as quantitative information about sleep patterns measured by a sensor. By combining the different sources of information (subjective as well as objective data), the diagnosis gives more insight into the nature of the sleep problem and is therefore more accurate. Furthermore, the disclosed system may be used to select specific components of the system that are medically relevant to the individual and therefore create a personalized program. The system teaches a selection of self-management skills that could help the individual to better cope with sleep disturbances and target those factors that maintain the problem or make it worse by a particular individual.

U.S. Publication No. 20150257697 for method and system for mobile, social, behavioral treatment of sleep by inventor Sepah, filed Mar. 17, 2014 and published Sep. 17, 2015, is directed to a method and system for mobile behavioral treatment of sleep issues such as insomnia comprising of: placing, participants into an online software platform that includes an online coach and group/community to reinforce compliance and provide social support; providing, a curriculum, compromising of modules of evidence-based behavioral treatments (e.g. cognitive-behavioral therapy (CBT), intensive sleep retraining (ISR)); providing, a wireless wearable body metric measurement device configured to communicate remotely with a mobile computing device and network; receiving a set of body metric measurement data via a mobile computing device; transmitting and storing the body metric measurement data on a server; determining trends and changes in the body metric measurement of the participant; providing, visual feedback regarding sleep quantity and quality to the participant via an online software platform that is accessible through mobile devices; calculating individualized recommendations based on body metric measurements and CBT protocols; providing, behavioral alerts to the participant via a wireless body metric device to alter sleep behaviors.

U.S. Publication No. 20160151603 for methods and systems for sleep management by inventors Shouldice et al., filed Dec. 21, 2015 and published Jun. 2, 2016, is directed to a processing system including methods to promote sleep. The system may include a monitor such as a non-contact motion sensor from which sleep information may be determined. User sleep information, such as sleep stages, hypnograms, sleep scores, mind recharge scores and body scores, may be recorded, evaluated and/or displayed for a user. The system may further monitor ambient and/or environmental conditions corresponding to sleep sessions. Sleep advice may be generated based on the sleep information, user queries and/or environmental conditions from one or more sleep sessions. Communicated sleep advice may include content to promote good sleep habits and/or detect risky sleep conditions. In some versions of the system, any one or more of a bedside unit sensor module, a smart processing device, such as a smart phone or smart device, and network servers may be implemented to perform the methodologies of the system.

U.S. Publication No. 20170017759 for cognitive behavioral therapy (CBT) method, system and application by inventors MacNeice, et al., filed Jul. 18, 2016 and published Jan. 19, 2017, is directed to a cognitive behavioral therapy (CBT) method, system and application for treating disorders/conditions such as e.g., insomnia, smoking cessation, alcohol addiction, depression, and nightmares, among others.

U.S. Publication No. 20170053068 for methods for enhancing wellness associated with habitable environments by inventors Pillai, et al., filed Aug. 26, 2016 and published Feb. 23, 2017, is directed to controlling environmental characteristics of habitable environments (e.g., hotel or motel rooms, spas, resorts, cruise boat cabins, offices, hospitals and/or homes, apartments or residences) to eliminate, reduce or ameliorate adverse or harmful aspects and introduce, increase or enhance beneficial aspects in order to improve a "wellness" or sense of "wellbeing" provided via the environments. Control of intensity and wavelength distribution of passive and active illumination addresses various issues, symptoms or syndromes, for instance to maintain a circadian rhythm or cycle, adjust for "jet lag" or season affective disorder, etc. Air quality and attributes are controlled. Scent(s) may be dispersed. Noise is reduced and sounds (e.g., masking, music, natural) may be provided. Environmental and biometric feedback is provided. Experimentation and machine learning are used to improve health outcomes and wellness standards.

U.S. Publication No. 20170189641 for method and system for characterizing and/or treating poor sleep behavior by inventors Moturu, et al., filed Mar. 21, 2017 and published Jul. 6, 2017, is directed to a method and system for improving sleep characterization and/or a sleeping-related disorder for a user associated with a sleep session that can include receiving a log of use dataset corresponding to user digital communication behavior at a mobile device, the log of use dataset associated with the sleep session; receiving a supplementary dataset characterizing activity of the user and/or mobile device, the supplementary dataset associated with the sleep session; characterizing a sleep-related parameter for the user based on at least one of the log of use dataset and the supplementary dataset; determining a sleep care plan for the user based on the sleep-related parameter, the sleep care plan including a therapeutic intervention; and promoting a therapeutic intervention to the user according to the sleep care plan.

U.S. Pat. No. 9,999,744 for monitoring device and cognitive behavior therapy by inventor Proud, filed Jun. 28, 2016 and issued Jun. 19, 2018, is directed to a user monitoring device system including a user monitoring device with a microphone and sensors to determine air quality, sound level/quality, light quality and ambient temperature near the user. A movement detection device detects a user's movement information. The movement detection device and the monitoring system assist to determine user sleep information and sleep behavior information. The microphone records user movement sounds detected by the movement detection device. The movement detection device is configured to cause the microphone to stop recording user movement sounds when the movement sounds are not directed to a sleep related parameter. In response to determining user sleep information or sleep behavior information the system is used for treatment of sleep or psychiatric disorders.

U.S. Publication No. 20180226155 for methods and systems for cognitive behavioral therapy by inventors Mahoney, et al., filed Feb. 2, 2018 and published Aug. 9, 2018, is directed to methods and systems for cognitive behavioral therapy. A first set of data and a second set of data related to a health attribute are received, over a first time period. The first and second sets of data are displayed in a first and a second graphical item. A graphical button is displayed on the first graphical item and configured to move it on a display. Using the graphical button, the first graphical item is, at least partially, overlaid upon the second graphical item. In response to the overlaying a third set of data is generated and displayed in a third graphical item. The third set of data is at least partially based on associating the first set of data with the second set of data using one or more sets of rules that establish the relationship between the first set of data and the second set of data.

U.S. Publication No. 20180260387 for systems and methods for dynamic user interaction for improving happiness by inventors Ben-Kiki, et al., filed May 9, 2018 and published Sep. 13, 2018, is directed to a computing system for interacting with a user comprises a processor and a memory storing executable software which, when executed by the processor, causes the processor to commence an interactive session with a user, receive input data from the user during the interactive session, analyze the received input data and output a response to the user to continue the interactive session with the user. The processor, prior to outputting the response, identifies one or more topics from the received input data, ascertains a tone of the received input data, generates a mirroring prompt based on the ascertained tone of the received input data, and output to the user the generated mirroring prompt. The processor outputs the mirroring prompt to the user during the interactive session to cause an increase in a level of engagement of the user with the interactive session.

U.S. Publication No. 20180285528 for sensor assisted mental health therapy by inventors Healey, et al., filed Mar. 30, 2017 and published Oct. 4, 2018, is directed to computer systems to allow users to record sensor readings of their environment and correlate these sensor readings with mental health events for later analysis to improve mental health diagnoses and treatments. A monitoring system comprising a computing device and a sensor set (comprising one or more sensors integral to or communicatively coupled to the computing device) may collect and store data collected about the user. This data may be stored in the computing device, or may be stored in a cloud based data-storage service. This data may be annotated or correlated (either manually, or automatically) with mental health events of the user and used for later analysis.

SUMMARY OF THE INVENTION

The present invention relates to articles, methods, and systems for stress reduction and sleep promotion.

In one embodiment, the present invention provides a system to reduce stress and promote sleep, including at least one remote device, at least one remote server, and at least one body sensor, wherein the at least one body sensor includes a heart rate sensor, wherein the at least one remote device is in network communication with the at least one remote server and the at least one body sensor, wherein the at least one remote device collects body sensor data from the at least one body sensor, wherein the at least one remote device is operable to analyze the body sensor data, thereby creating analyzed body sensor data, wherein the analyzed body sensor data includes at least a resting heart rate and a heart rate variability, wherein the at least one remote device is operable to estimate sleep stages from the body sensor data and/or the analyzed body sensor data, wherein the at least one remote device stores a chronotype for a user, wherein the at least one remote device classifies a user into at least one group based on a user profile, the body sensor data, and/or user provided information, and wherein the at least one remote server is operable to run at least one algorithm to suggest at least one intervention to the user to reduce stress and/or promote sleep based on the user profile, the body sensor data, the analyzed body sensor data, and the user provided information.

In another embodiment, the present invention provides a system to reduce stress and promote sleep, including at least one remote device, at least one remote server, and at least one body sensor, wherein the at least one body sensor includes a heart rate sensor, wherein the at least one remote device is in network communication with the at least one remote server and the at least one body sensor, wherein the at least one remote device collects body sensor data from the at least one body sensor, wherein the at least one remote device analyzes the body sensor data, thereby creating analyzed body sensor data, wherein the analyzed body sensor data includes at least a resting heart rate and a heart rate variability, wherein the at least one remote device is operable to estimate sleep stages from the body sensor data and/or the analyzed body sensor data, wherein the at least one remote device stores a chronotype for a user, wherein the at least one remote device classifies a user into at least one group based on a user profile, the body sensor data, and/or user provided information, wherein the at least one remote server is operable to run at least one algorithm to suggest at least one intervention to the user to reduce stress and/or promote sleep based on the user profile, the body sensor data, the analyzed body sensor data, and the user provided information, and wherein the at least one intervention includes automatically adjusting a temperature of a sleeping surface using a mattress, a mattress pad, and/or a blanket.

In yet another embodiment, the present invention provides a system to reduce stress and promote sleep, including at least one remote device, at least one remote server, at least one body sensor, wherein the at least one body sensor includes a heart rate sensor, and at least one environmental sensor, wherein the at least one remote device is in network communication with the at least one remote server, the at least one body sensor, and the at least one environmental sensor, wherein the at least one remote device collects body sensor data from the at least one body sensor and environmental sensor data from the at least one environmental sensor, wherein the at least one remote device is operable to analyze the body sensor data, thereby creating analyzed body sensor data, wherein the analyzed body sensor data includes at least a resting heart rate and a heart rate variability, wherein the at least one remote device is operable to analyze the environmental sensor data, thereby creating analyzed environmental sensor data, wherein the at least one remote device is operable to estimate sleep stages from the body sensor data, wherein the at least one remote device stores a chronotype for a user, wherein the chronotype is determined by a body temperature sensor and/or a genetic test, wherein the at least one remote device classifies a user into at least one group based on a user profile, the body sensor data, and/or user provided information, wherein the at least one remote server is operable to run at least one algorithm to suggest at least one intervention to the user to reduce stress and/or promote sleep based on the user profile, the body sensor data, the analyzed body sensor data, the analyzed environmental sensor data, and the user provided information, and wherein the at least one intervention includes automatically adjusting a temperature of a sleeping surface using a mattress, a mattress pad, and/or a blanket.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 5 illustrates a welcome screen for one embodiment of a GUI for a mobile application.

FIG. 6 illustrates an account creation screen for one embodiment of a GUI for a mobile application.

FIG. 7 illustrates the account creation screen with the user information added.

FIG. 8 illustrates an example of a GUI describing benefits of using the mobile application.

FIG. 66 illustrates an example of a chronotype self-assessment quiz.

FIG. 69 shows a table with an example of connections for users.

DETAILED DESCRIPTION

Figure 1:
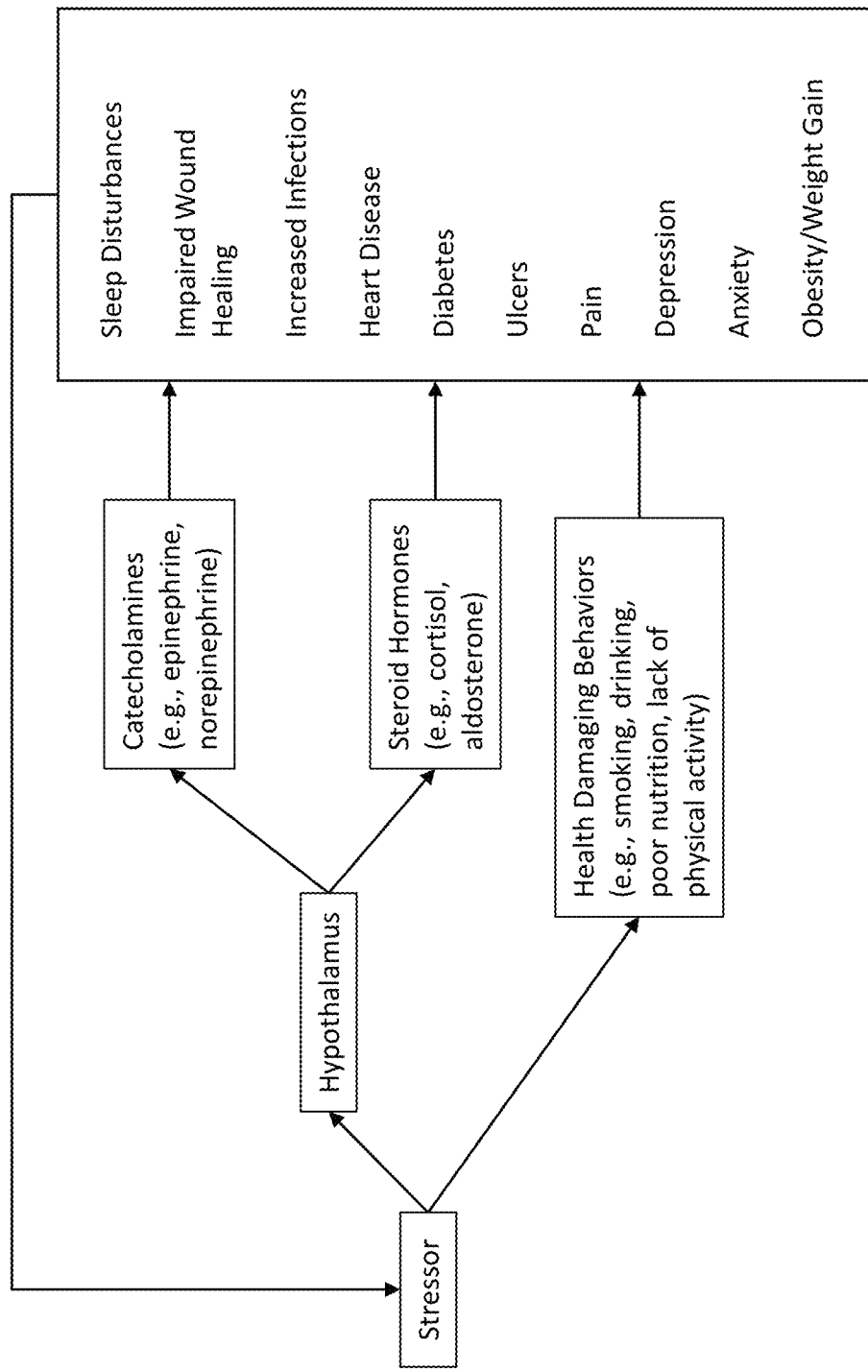
FIG. 1 illustrates the effects of a stressor on the body.

The present invention is generally directed to articles, methods, and systems for stress reduction and sleep promotion.

In one embodiment, the present invention provides a system to reduce stress and promote sleep, including at least one remote device, at least one remote server, and at least one body sensor, wherein the at least one body sensor includes a heart rate sensor, wherein the at least one remote device is in network communication with the at least one remote server and the at least one body sensor, wherein the at least one remote device collects body sensor data from the at least one body sensor, wherein the at least one remote device is operable to analyze the body sensor data, thereby creating analyzed body sensor data, wherein the analyzed body sensor data includes at least a resting heart rate and a heart rate variability, wherein the at least one remote device is operable to estimate sleep stages from the body sensor data and/or the analyzed body sensor data, wherein the at least one remote device stores a chronotype for a user, wherein the at least one remote device classifies a user into at least one group based on a user profile, the body sensor data, and/or user provided information, and wherein the at least one remote server is operable to run at least one algorithm to suggest at least one intervention to the user to reduce stress and/or promote sleep based on the user profile, the body sensor data, the analyzed body sensor data, and the user provided information.

In another embodiment, the present invention provides a system to reduce stress and promote sleep, including at least one remote device, at least one remote server, and at least one body sensor, wherein the at least one body sensor includes a heart rate sensor, wherein the at least one remote device is in network communication with the at least one remote server and the at least one body sensor, wherein the at least one remote device collects body sensor data from the at least one body sensor, wherein the at least one remote device analyzes the body sensor data, thereby creating analyzed body sensor data, wherein the analyzed body sensor data includes at least a resting heart rate and a heart rate variability, wherein the at least one remote device is operable to estimate sleep stages from the body sensor data and/or the analyzed body sensor data, wherein the at least one remote device stores a chronotype for a user, wherein the at least one remote device classifies a user into at least one group based on a user profile, the body sensor data, and/or user provided information, wherein the at least one remote server is operable to run at least one algorithm to suggest at least one intervention to the user to reduce stress and/or promote sleep based on the user profile, the body sensor data, the analyzed body sensor data, and the user provided information, and wherein the at least one intervention includes automatically adjusting a temperature of a sleeping surface using a mattress, a mattress pad, and/or a blanket.

In yet another embodiment, the present invention provides a system to reduce stress and promote sleep, including at least one remote device, at least one remote server, at least one body sensor, wherein the at least one body sensor includes a heart rate sensor, and at least one environmental sensor, wherein the at least one remote device is in network communication with the at least one remote server, the at least one body sensor, and the at least one environmental sensor, wherein the at least one remote device collects body sensor data from the at least one body sensor and environmental sensor data from the at least one environmental sensor, wherein the at least one remote device is operable to analyze the body sensor data, thereby creating analyzed body sensor data, wherein the analyzed body sensor data includes at least a resting heart rate and a heart rate variability, wherein the at least one remote device is operable to analyze the environmental sensor data, thereby creating analyzed environmental sensor data, wherein the at least one remote device is operable to estimate sleep stages from the body sensor data, wherein the at least one remote device stores a chronotype for a user, wherein the chronotype is determined by a body temperature sensor and/or a genetic test, wherein the at least one remote device classifies a user into at least one group based on a user profile, the body sensor data, and/or user provided information, wherein the at least one remote server is operable to run at least one algorithm to suggest at least one intervention to the user to reduce stress and/or promote sleep based on the user profile, the body sensor data, the analyzed body sensor data, the analyzed environmental sensor data, and the user provided information, and wherein the at least one intervention includes automatically adjusting a temperature of a sleeping surface using a mattress, a mattress pad, and/or a blanket.

Several studies show a link between stress and illness. Stress may cause physiological changes and lead individuals to adopt health damaging behaviors (e.g., smoking, drinking, poor nutrition, lack of physical activity). These physiological changes and health damaging behaviors can cause illnesses, such as sleep disturbances, impaired wound healing, increased infections, heart disease, diabetes, ulcers, pain, depression, and obesity or weight gain.

The body reacts to stress through two systems: the autonomic nervous system and the hypothalamic-pituitary-adrenal (HPA) axis. The autonomic nervous system, which consists of the sympathetic nervous system and the parasympathetic nervous system, is responsible for reacting to short term ("acute") stress. In response to short term stress, the sympathetic nervous system activates the "fight or flight response" through the sympathoadrenal medullary (SAM) axis. This causes the adrenal medulla to secrete catecholamines (e.g., epinephrine and norepinephrine), which causes blood glucose levels to rise, blood vessels to constrict, heart rate to increase, and blood pressure to rise. Blood is diverted from nonessential organs to the heart and skeletal muscles, which leads to decreased digestive system activity and reduced urine output. Additionally, the metabolic rate increases and bronchioles dilate. The parasympathetic nervous system then returns the body to homeostasis.

The HPA axis is responsible for reacting to long term ("chronic") stress. This causes the adrenal cortex to secrete steroid hormones (e.g., mineralocorticoids and glucocorticoids). Mineralocorticoids (e.g., aldosterone) cause retention of sodium and water by the kidneys, increased blood pressure, and increased blood volume. Glucocorticoids (e.g., cortisol) cause proteins and fats to be converted to glucose or broken down for energy, increased blood glucose, and suppression of the immune system.

Thus, stress impacts the body on a cellular level and is a precursor to many disease states. Therefore, it is important to manage and treat stress to maintain health. However, as a result of modern lifestyles, most people are busy, tired, and stressed out. Most people also lack the time and energy to obtain treatments for minor ailments or treatments to prevent disease. What is needed is a convenient treatment that reduces stress and inflammation and promotes healing.

Energy medicine (e.g., biofield therapies, bioelectromagnetic therapies, acupuncture, homeopathy) focuses on the principle that small changes repeated over time can change the dynamics of the body and stimulate healing. The present invention utilizes that principle to reduce stress, promote sleep, and stimulate healing. Further, the present invention reduces stress and stimulates healing in small increments throughout the day and by encouraging more restful sleep at night, which are both convenient for the user.

Referring now to the drawings in general, the illustrations are for the purpose of describing a preferred embodiment of the invention and are not intended to limit the invention thereto.

FIG. 1 illustrates the effects of a stressor on the body. The body releases catecholamines or steroid hormones as a physiological response to the stressor. Stress may also lead individuals to adopt health damaging behaviors (e.g., smoking, drinking, poor nutrition, lack of physical activity). This may lead to illnesses, such as sleep disturbances, impaired wound healing, increased infections, heart disease, diabetes, ulcers, pain, depression, anxiety, and/or obesity or weight gain. These illnesses themselves may become a stressor, which triggers the cycle to continue and causes further physical and mental problems.

Figure 2:
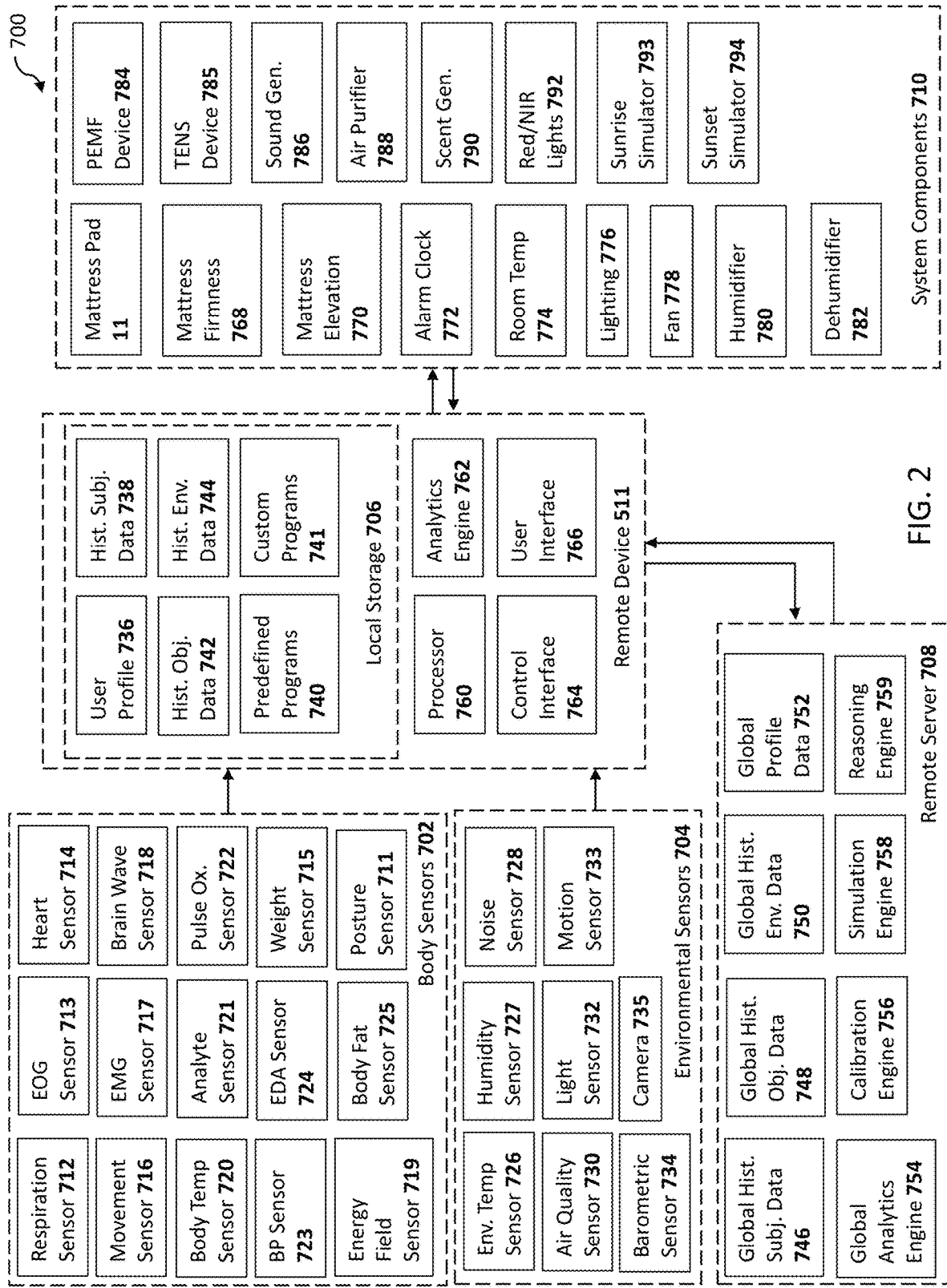
FIG. 2 is a block diagram of one embodiment of the stress reduction and sleep promotion system.

FIG. 2 is a block diagram of one embodiment of a stress reduction and sleep promotion system. The stress reduction and sleep promotion system 700 includes body sensors 702, environmental sensors 704, a remote device 511 with local storage 706, a remote server 708, and system components 710. The body sensors 702 include a posture sensor 711, a respiration sensor 712, an electrooculography (EOG) sensor 713, a heart rate sensor 714, a body weight sensor 715, a movement sensor 716, an electromyography (EMG) sensor 717, a brain wave sensor 718, a body temperature sensor 720, an analyte sensor 721, a pulse oximeter sensor 722, a blood pressure (BP) sensor 723, an electrodermal activity (EDA) sensor 724, and/or a body fat sensor 725. In one embodiment, at least one body sensor 702 is implanted in the body of a user. In a preferred embodiment, at least one body sensor 702 is operable to transmit data to the remote device 511 and/or the remote server 708 in real time.

The posture sensor 711 measures a posture of an individual. In one embodiment, the posture sensor 711 includes at least one pressure sensor. The at least one pressure sensor is preferably embedded in a seat and/or seat cushion (e.g., DARMA, SENSIMAT). In another embodiment, the posture sensor 711 is a wearable device (e.g., LUMOback Posture Sensor). In another embodiment, the posture sensor 711 includes at least one camera. The at least one camera is operable to detect a posture of the individual using, e.g., computer vision.

The respiration sensor 712 measures a respiratory rate. In one embodiment, the respiration sensor 712 is incorporated into a wearable device (e.g., a chest strap). In another embodiment, the respiration sensor 712 is incorporated into a patch or a bandage. Alternatively, the respiratory rate is estimated from an electrocardiogram, a photoplethysmogram (e.g., a pulse oximeter), and/or an accelerometer. In yet another embodiment, the respiratory sensor 712 uses a non-contact motion sensor to monitor respiration.

The electrooculography (EOG) sensor 713 measures the corneo-retinal standing potential that exists between the front and the back of the eye. Measurements of eye movements are done by placing pairs of electrodes either above and below the eye or to the left and right of the eye. If the eye moves to a position away from the center and toward one of the electrodes, a potential difference occurs between the electrodes. The recorded potential is a measure of the eye's position.

The heart sensor 714 is preferably incorporated into a wearable device (e.g., APPLE WATCH, FITBIT, SAMSUNG GALAXY WATCH). Alternatively, the heart sensor 714 is attached to the user with a chest strap. In another embodiment, the heart sensor 714 is incorporated into a patch or a bandage. In yet another embodiment, the heart sensor 714 is incorporated into a sensor device on or under the mattress (e.g., BEDDIT, EMFIT QS). Alternatively, the heart sensor 714 is embedded in the mattress. A heart rate is determined using electrocardiography, pulse oximetry, ballistocardiography, or seismocardiography. In one embodiment, the heart sensor 714 measures heart rate variability (HRV). HRV is a measurement of the variation in time intervals between heartbeats. A high HRV measurement is indicative of less stress, while a low HRV measurement is indicative of more stress. Studies have linked abnormalities in HRV to diseases where stress is a factor (e.g., diabetes, depression, congestive heart failure). In one embodiment, a Poincare plot is generated to display HRV on a device such as a smartphone. In another embodiment, the heart sensor 714 is an electrocardiogram.

The body weight sensor 715 is preferably a smart scale (e.g., FITBIT ARIA, WITHINGS BODY+, GARMIN INDEX, PIVOTAL LIVING SMART SCALE, IHEALTH CORE). Alternatively, the body weight sensor 715 is at least one pressure sensor embedded in a mattress or a mattress topper. In one embodiment, the stress reduction and sleep promotion system 700 is also operable to determine a height of a user using the at least one pressure sensor embedded in a mattress or a mattress topper. In another embodiment, a body mass index (BMI) of the user is calculated using the body weight of the user and the height of the user as measured by the at least one pressure sensor.

The movement sensor 716 is an accelerometer and/or a gyroscope. In one embodiment, the accelerometer and/or the gyroscope are incorporated into a wearable device (e.g., FITBIT, APPLE WATCH, SAMSUNG GALAXY WATCH, actigraph). In another embodiment, the accelerometer and/or the gyroscope are incorporated into a smartphone. In alternative embodiment, the movement sensor 716 is a non-contact sensor. In one embodiment, the movement sensor 716 is at least one piezoelectric sensor. In another embodiment, the movement sensor 716 is a pyroelectric infrared sensor (i.e., a "passive" infrared sensor). In yet another embodiment, the movement sensor 716 is at least one pressure sensor embedded in a mattress or mattress topper. Alternatively, the movement sensor 716 is incorporated into a smart fabric. In still another embodiment, the movement sensor 716 is operable to analyze a gait of a user.

The electromyography (EMG) sensor 717 records the electrical activity produced by skeletal muscles. Impulses are recorded by attaching electrodes to the skin surface over the muscle. In a preferred embodiment, three electrodes are placed on the chin. One in the front and center and the other two underneath and on the jawbone. These electrodes demonstrate muscle movement during sleep, which can be used to detect REM or NREM sleep. In another embodiment, two electrodes are placed on the inside of each calf muscle about 2 to 4 cm (about 0.8 to 1.6 inches) apart. In yet another embodiment, two electrodes are placed over the anterior tibialis of each leg. The electrodes on the leg can be used to detect movement of the legs during sleep, which may occur with Restless Leg Syndrome or Periodic Limb Movements of Sleep.

The brain wave sensor 718 is preferably an electroencephalogram (EEG) with at least one channel. In a preferred embodiment, the EEG has at least two channels. Multiple channels provide higher resolution data. The frequencies in EEG data indicate particular brain states. The brain wave sensor 718 is preferably operable to detect delta, theta, alpha, beta, and gamma frequencies. In another embodiment, the brain wave sensor 718 is operable to identify cognitive and emotion metrics, including focus, stress, excitement, relaxation, interest, and/or engagement. In yet another embodiment, the brain wave sensor 718 is operable to identify cognitive states that reflect the overall level of engagement, attention and focus and/or workload that reflects cognitive processes (e.g., working memory, problem solving, analytical reasoning).

The energy field sensor 719 measures an energy field of a user. In one embodiment, the energy field sensor 719 is a gas discharge visualization (GDV) device. Examples of a GDV device are disclosed in U.S. Pat. Nos. 7,869,636 and 8,321,010 and U.S. Publication No. 20100106424, each of which is incorporated herein by reference in its entirety. The GDV device utilizes the Kirlian effect to evaluate an energy field. In a preferred embodiment, the GDV device utilizes a high-intensity electric field (e.g., 1024 Hz, 10 kV, square pulses) input to an object (e.g., human fingertips) on an electrified glass plate. The high-intensity electric field produces a visible gas discharge glow around the object (e.g., fingertip). The visible gas discharge glow is detected by a charge-coupled detector and analyzed by software on a computer. The software characterizes the pattern of light emitted (e.g., brightness, total area, fractality, density). In a preferred embodiment, the software utilizes Mandel's Energy Emission Analysis and the Su-Jok system of acupuncture to create images and representations of body systems. The energy field sensor 719 is preferably operable to measure stress levels, energy levels, and/or a balance between the left and right sides of the body.

The body temperature sensor 720 measures core body temperature and/or skin temperature. The body temperature sensor 720 is a thermistor, an infrared sensor, or thermal flux sensor. In one embodiment, the body temperature sensor 720 is incorporated into a ring, an armband, or a wristband. In another embodiment, the body temperature sensor 720 is incorporated into a patch or a bandage. In yet another embodiment, the body temperature sensor 720 is an ingestible core body temperature sensor (e.g., CORTEMP). The body temperature sensor 720 is preferably wireless.

The analyte sensor 721 monitors levels of an analyte in blood, sweat, tears, saliva, or interstitial fluid. Alternatively, the analyte sensor 721 monitors levels of an analyte in lymph, urine, or breath (i.e., breathalyzer). In one embodiment, the analyte is an electrolyte, a small molecule (molecular weight<900 Daltons), a protein (e.g., C-reactive protein), and/or a metabolite. In another embodiment, the analyte is glucose, lactate, glutamate, oxygen, sodium, chloride, potassium, calcium, ammonium, copper, magnesium, iron, zinc, creatinine, uric acid, oxalic acid, urea, ethanol, an amino acid, a hormone (e.g., cortisol, melatonin), a steroid, a neurotransmitter, a catecholamine, a cytokine, and/or an interleukin (e.g., IL-6). The analyte sensor 721 is preferably non-invasive. Alternatively, the analyte sensor 721 is minimally invasive or implanted. In one embodiment, the analyte sensor 721 is incorporated into a wearable device. Alternatively, the analyte sensor 721 is incorporated into a patch or a bandage.

The pulse oximeter sensor 722 monitors oxygen saturation. In one embodiment, the pulse oximeter sensor 722 is worn on a finger, a toe, or an ear. In another embodiment, the pulse oximeter sensor 722 is incorporated into a patch or a bandage. The pulse oximeter sensor 722 is preferably wireless. Alternatively, the pulse oximeter sensor 722 is wired. In one embodiment, the pulse oximeter sensor 722 is connected by a wire to a wrist strap or a strap around a hand. In another embodiment, the pulse oximeter sensor 722 is combined with a heart rate sensor 714. In yet another embodiment, the pulse oximeter sensor 722 uses a camera lens on a smartphone or a tablet.

The blood pressure (BP) sensor 723 is a sphygmomanometer. The sphygmomanometer is preferably wireless. Alternatively, the blood pressure sensor 723 estimates the blood pressure without an inflatable cuff (e.g., SALU PULSE+). In one embodiment, the blood pressure sensor 723 is incorporated into a wearable device.

The electrodermal activity sensor 724 measures sympathetic nervous system activity. Electrodermal activity is more likely to have high frequency peak patterns (i.e., "storms") during deep sleep. In one embodiment, the electrodermal activity sensor 724 is incorporated into a wearable device. Alternatively, the electrodermal activity sensor 724 is incorporated into a patch or a bandage.

The body fat sensor 725 is preferably a bioelectrical impedance device. In one embodiment, the body fat sensor 725 is incorporated into a smart scale (e.g., FITBIT ARIA, WITHINGS BODY+, GARMIN INDEX, PIVOTAL LIVING SMART SCALE, IHEALTH CORE). Alternatively, the body fat sensor 725 is a handheld device.

The environmental sensors 704 include an environmental temperature sensor 726, a humidity sensor 727, a noise sensor 728, an air quality sensor 730, a light sensor 732, a motion sensor 733, a barometric sensor 734, and/or a camera 735. In one embodiment, the environmental temperature sensor 726, the humidity sensor 727, the noise sensor 728, the air quality sensor 730, the light sensor 732, the motion sensor 733, the barometric sensor 734, the camera 735 are incorporated into a home automation system (e.g., AMAZON ALEXA, APPLE HOMEKIT, GOOGLE HOME, IF THIS THEN THAT (IFTTT), NEST). Alternatively, the environmental temperature sensor 726, the humidity sensor 727, the noise sensor 728, the light sensor 732, and/or the camera 735 are incorporated into a smartphone or tablet. In one embodiment, the noise sensor 728 is a microphone. In one embodiment, the air quality sensor 730 measures carbon monoxide, carbon dioxide, nitrogen dioxide, sulfur dioxide, particulates, and/or volatile organic compounds (VOCs). In another embodiment, at least one environmental sensor 704 is operable to transmit data to the remote device 511 and/or the remote server 708 in real time.

The remote device 511 is preferably a smartphone or a tablet. Alternatively, the remote device 511 is a laptop or a desktop computer. The remote device 511 includes a processor 760, an analytics engine 762, a control interface 764, and a user interface 766. The remote device 511 accepts data input from the body sensors 702 and/or the environmental sensors 704. The remote device also accepts data input from the remote server 708. The remote device 511 stores data in a local storage 706.

The local storage 706 on the remote device 511 includes a user profile 736, historical subjective data 738, predefined programs 740, custom programs 741, historical objective data 742, and historical environmental data 744. The user profile 736 stores stress reduction and sleep promotion system preferences and information about the user, including but not limited to, age, weight, height, gender, medical history (e.g., sleep conditions, medications, diseases), fitness (e.g., fitness level, fitness activities), sleep goals, stress level, and/or occupational information (e.g., occupation, shift information). The medical history includes caffeine consumption, alcohol consumption, tobacco consumption, use of prescription sleep aids and/or other medications, blood pressure, restless leg syndrome, narcolepsy, headaches, heart disease, sleep apnea, depression, stroke, diabetes, insomnia, anxiety or post-traumatic stress disorder (PTSD), and/or neurological disorders.

In one embodiment, the medical history incorporates information gathered from the Epworth Sleepiness Scale (ESS), the Insomnia Severity Index (IR), Generalized Anxiety Disorder 7-item (GAD-7) Scale, and/or Patient Heath Questionnaire-9 (PHQ-9) (assessment of depression). The ESS is described in Johns M W (1991). "A new method for measuring daytime sleepiness: the Epworth sleepiness scale", *Sleep,* 14 (6): 540-5, which is incorporated herein by reference in its entirety. The ISI is described in Morin et al. (2011). "The Insomnia Severity Index: Psychometric Indicators to Detect Insomnia Cases and Evaluate Treatment Response", *Sleep,* 34(5): 601-608, which is incorporated herein by reference in its entirety. The GAD-7 is described in Spitzer et al., "A brief measure for assessing generalized anxiety disorder: the GAD-7", *Arch Intern Med.,* 2006 May 22; 166(1):1092-7, which is incorporated herein by reference in its entirety. The PHQ-9 is described in Kroenke et al., "The PHQ-9: Validity of a Brief Depression Severity Measure", *J. Gen. Intern. Med.,* 2001 September; 16(9): 606-613, which is incorporated herein by reference in its entirety.

In one embodiment, the weight of the user is automatically uploaded to the local storage from a third-party application. In one embodiment, the third-party application obtains the information from a smart scale (e.g., FITBIT ARIA, WITHINGS BODY+, GARMIN INDEX, PIVOTAL LIVING SMART SCALE, IHEALTH CORE). In another embodiment, the medical history includes information gathered from a Resting Breath Hold test.

The historical objective data 742 includes information gathered from the body sensors 702. This includes information from the respiration sensor 712, the electrooculography sensor 713, the heart sensor 714, the movement sensor 716, the electromyography sensor 717, the brain wave sensor 718, the energy field sensor 719, the body temperature sensor 720, the analyte sensor 721, the pulse oximeter sensor 722, the blood pressure sensor 723, and/or the electrodermal activity sensor 724. In another embodiment, the historical objective data 742 includes information gathered from the Maintenance of Wakefulness Test, the Digit Symbol Substitution Test, and/or the Psychomotor Vigilance Test. The Maintenance of Wakefulness Test is described in Doghramji, et al., "A normative study of the maintenance of wakefulness test (MWT)", *Electroencephalogr. Clin. Neurophysiol.,* 1997 November; 103(5): 554-562, which is incorporated herein by reference in its entirety. The Digit Symbol Substitution Test is described in Wechsler, D. (1997). Wechsler Adult Intelligence Scale-Third edition (WAIS-III). San Antonio, TX: Psychological Corporation and Wechsler, D. (1997). Wechsler Memory Scale-Third edition (WMS-III). San Antonio, TX: Psychological Corporation, each of which is incorporated herein by reference in its entirety. The Psychomotor Vigilance Test is described in Basner et al., "Maximizing sensitivity of the psychomotor vigilance test (PVT) to sleep loss", *Sleep,* 2011 May 1; 34(5): 581-91, which is incorporated herein by reference in its entirety.

In another embodiment, the historical objective data 742 includes results from at least one genetic test (e.g., ANCESTRYDNA, 23ANDME). In one embodiment, the at least one genetic test includes information regarding at least one gene, wherein the at least one gene includes RGS16, VIP, PER2, HCRTR2, RASD1, PER3, FBXL3, PLCL1, APH1A, FBXL13, NOL4, TOX3, AKS, DLSX5, PER1, and/or ALG10B. In another embodiment, the at least one genetic test includes information regarding at least one marker, wherein the at least one marker includes rs12736689, rs9479402, rs55694368, rs35833281, rs11545787, rs11121022, rs9565309, rs1595824, rs34714364, rs3972456, rs12965577, rs12927162, rs10493596, rs2948276, and/or rs6582618.

In yet another embodiment, the historical objective data 742 includes a chronotype. In one embodiment, the chronotype is determined using a self-assessment. In another embodiment, the chronotype is determined used the results from the at least one genetic test (e.g., PER3 gene). In yet another embodiment, the chronotype is determined using the body temperature sensor 720. Additional information regarding chronotype is in Putilov, et al., *How many diurnal types are there? A search for two further "bird species"* in Personality and Individual Differences, Volume 72, January 2015, pages 12-17, Schuster, et al. (2019). *Shift-specific associations between age, chronotype and sleep duration.* Chronobiology International, 36(6), 784-795. doi: 10.1080/07420528.2019.1586719, and Breus, Michael. *The Power of When: Discover Your Chronotype.* Little, Brown and Company, 2016, each of which is incorporated herein by reference in its entirety. In one embodiment, the system calculates a mid-sleep point. For example, if a sleep onset time is 11:00 μm and a sleep end time is 7:00 am, the mid-sleep point is 3:00 am.

The historical environmental data 744 includes information gathered from the environmental sensors 704. This includes information from the environmental temperature sensor 726, the humidity sensor 727, the noise sensor 728, the air quality sensor 730, the light sensor 732, the barometric sensor 734, and/or the camera 735.

The historical subjective data 738 includes information regarding sleep and/or stress. In one embodiment, the information regarding sleep is gathered from manual sleep logs (e.g., Pittsburgh Sleep Quality Index). The manual sleep logs include, but are not limited to, a time sleep is first attempted, a time to fall asleep, a time of waking up, hours of sleep, number of awakenings, times of awakenings, length of awakenings, perceived sleep quality, use of medications to assist with sleep, difficulty staying awake and/or concentrating during the day, difficulty with temperature regulation at night (e.g., too hot, too cold), trouble breathing at night (e.g., coughing, snoring), having bad dreams, waking up in the middle of the night or before a desired wake up time, twitching or jerking in the legs while asleep, restlessness while asleep, difficulty sleeping due to pain, and/or needing to use the bathroom in the middle of the night. The Pittsburgh Sleep Quality Index is described in Buysse, et al., "The Pittsburgh sleep quality index: A new instrument for psychiatric practice and research". *Psychiatry Research.* 28 (2): 193-213 (May 1989), which is incorporated herein by reference in its entirety.

In another embodiment, the historical subjective data 738 includes information gathered regarding sleepiness (e.g., Karolinska Sleepiness Scale, Stanford Sleepiness Scale, Epworth Sleepiness Scale). The Karolinska Sleepiness Scale is described in Åkerstedt, et al., "Subjective and objective sleepiness in the active individual", *Int J Neurosc.,* 1990; 52:29-37 and Baulk et al., "Driver sleepiness—evaluation of reaction time measurement as a secondary task", *Sleep,* 2001; 24(6):695-698, each of which is incorporated herein by reference in its entirety. The Stanford Sleepiness Scale is described in Hoddes E. (1972). "The development and use of the Stanford sleepiness scale (SSS)" *Psychophysiology.* 9 (150) and Maclean, et al (1992-03-01). "Psychometric evaluation of the Stanford Sleepiness Scale". *Journal of Sleep Research.* 1 (1): 35-39, each of which is incorporated herein by reference in its entirety.

In yet another embodiment, the historical subjective data 738 includes information regarding tension or anxiety, depression or dejection, anger or hostility, and/or fatigue or inertia gathered from the Profile of Mood States. The Profile of Mood States is described in the Profile of Mood States, $2^{nd}$ Edition published by Multi-Health Systems (2012) and Curran et al., "Short Form of the Profile of Mood States (POMS-SF): Psychometric information", *Psychological Assessment.* 7 (1): 80-83 (1995), each of which is incorporated herein by reference in its entirety. In another embodiment, the historical subjective data 738 includes information gathered from the Ford Insomnia Response to Stress Test (FIRST), which asks how likely a respondent is to have difficulty sleeping in nine different situations. The FIRST is described in Drake et al., "Vulnerability to stress-related sleep disturbance and hyperarousal", *Sleep,* 2004; 27:285-91 and Drake et al., "Stress-related sleep disturbance and polysomnographic response to caffeine", *Sleep Med.,* 2006; 7:567-72, each of which is incorporated herein by reference in its entirety. In still another embodiment, the historical subjective data 738 includes information gathered from the Impact of Events, which assesses the psychological impact of stressful life events. A subscale score is calculated for intrusion, avoidance, and/or hyperarousal. The Impact of Events is described in Weiss, D. S., & Marmar, C. R. (1996). The Impact of Event Scale—Revised. In J. Wilson & T. M. Keane (Eds.), Assessing psychological trauma and PTSD (pp. 399-411). New York: Guilford, which is incorporated herein by reference in its entirety. In one embodiment, the historical subjective data 738 includes information gathered from the Social Readjustment Rating Scale (SRRS). The SRRS lists 52 stressful life events and assigns a point value based on how traumatic the event was determined to be by a sample population. The SRRS is described in Holmes et al., "The Social Readjustment Rating Scale", *J. Psychosom. Res.* 11(2): 213-8 (1967), which is incorporated herein by reference in its entirety.

In one embodiment, the predefined programs 740 are general sleep settings for various conditions and/or body types (e.g., weight loss, comfort, athletic recovery, hot flashes, bed sores, depression, multiple sclerosis, alternative sleep cycles). In one embodiment, a weight loss predefined program sets a surface temperature at a very cold setting (e.g., 15.56-18.89° C. (60-66° F.)) to increase a metabolic response, resulting in an increase in calories burned, which then leads to weight loss. Temperature settings are automatically adjusted to be as cold as tolerable by the user after the first sleep cycle starts to maximize the caloric burn while having the smallest impact on sleep quality. The core temperature of an overweight individual may fail to drop due to a low metabolism. In one example, the surface temperature is 20° C. (68° F.) at the start of a sleep period, 18.89° C. (66° F.) during N1-N2 sleep, 18.33° C. (65° F.) during N3 sleep, 19.44° C. (67° F.) during REM sleep, and 20° C. (68° F.) to wake the user.

In one embodiment, the custom programs 741 are sleep settings defined by the user. In one example, the user creates a custom program by modifying a predefined program (e.g., the weight loss program above) to be 1.11° C. (2° F.) cooler during the N3 stage. In another example, the user creates a custom program by modifying a predefined program to have a start temperature of 37.78° C. (100° F.). The custom programs 741 allow a user to save preferred sleep settings.

The remote server 708 includes global historical subjective data 746, global historical objective data 748, global historical environmental data 750, global profile data 752, a global analytics engine 754, a calibration engine 756, a simulation engine 758, and a reasoning engine 759. The global historical subjective data 746, the global historical objective data 748, the global historical environmental data 750, and the global profile data 752 include data from multiple users.

The system components 710 include a mattress pad 11 with adjustable temperature control, a mattress with adjustable firmness 768, a mattress with adjustable elevation 770, an alarm clock 772, a thermostat to adjust the room temperature 774, a lighting system 776, a fan 778, a humidifier 780, a dehumidifier 782, a pulsed electromagnetic field (PEMF) device 784, a transcutaneous electrical nerve stimulation (TENS) device 785, a sound generator 786, an air purifier 788, a scent generator 790, a red light and/or near-infrared lighting device 792, a sunrise simulator 793, and/or a sunset simulator 794.

The body sensors 702, the environmental sensors 704, the remote device 511 with local storage 706, the remote server 708, and the system components 710 are designed to connect directly (e.g., Universal Serial Bus (USB) or equivalent) or wirelessly (e.g., BLUETOOTH, WI-FI, ZIGBEE) through systems designed to exchange data between various data collection sources. In a preferred embodiment, the body sensors 702, the environmental sensors 704, the remote device 511 with local storage 706, the remote server 708, and the system components 710 communicate wirelessly through BLUETOOTH. Advantageously, BLUETOOTH emits lower electromagnetic fields (EMFs) than WI-FI and cellular signals.

Additional information regarding the stress reduction and sleep promotion system is in U.S. Publication Nos. 20180000255 and 20180110960, each of which is incorporated herein by reference in its entirety. U.S. Application No. 62/780,637, filed Dec. 17, 2018, discusses a system for enhancing sleep recovery and promoting weight loss and is incorporated herein by reference in its entirety. U.S. Application No. 62/792,572, filed Jan. 15, 2019, discusses a health data exchange platform and is incorporated herein by reference in its entirety.

Figure 3:
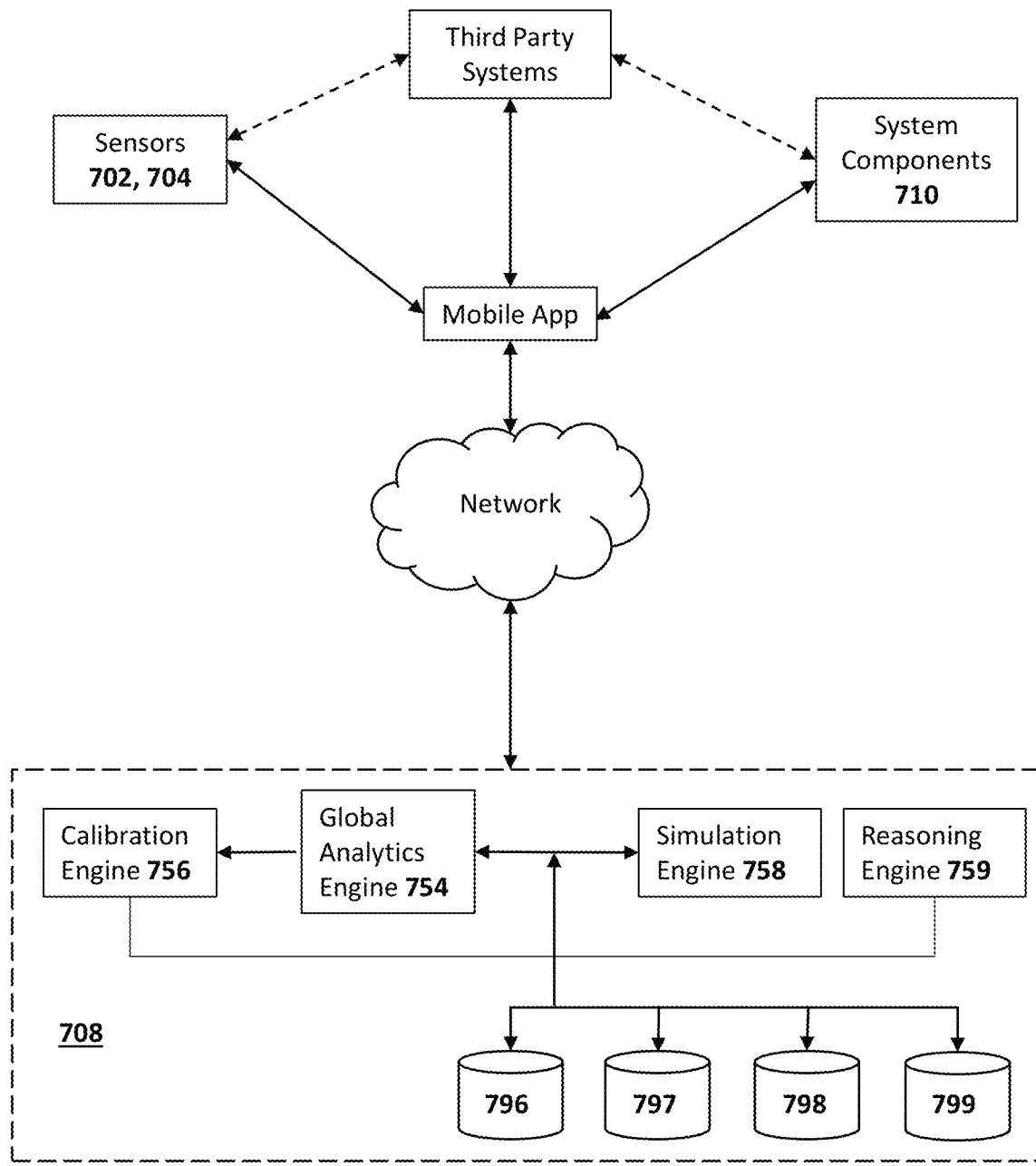
FIG. 3 is a block diagram of one embodiment of the system architecture.

As shown in FIG. 3, in one embodiment, the remote server 708 hosts a global analytics engine 754, a calibration engine 756, a simulation engine 758, a reasoning engine 759, and databases 796, 797, 798, and 799. Although four databases are shown, it is equally possible to have any number of databases greater than one. The global analytics engine 754 generates predicted values for a monitored stress reduction and sleep promotion system using a virtual model of the stress reduction and sleep promotion system based on real-time data. The calibration engine 756 modifies and updates the virtual model based on the real-time data. Any operational parameter of the virtual model may be modified by the calibration engine 756 as long as the resulting modification is operable to be processed by the virtual model.

The global analytics engine 754 analyzes differences between the predicted values and optimized values. If the difference between the optimized values and the predicted values is greater than a threshold, then the simulation engine 758 determines optimized values of the monitored stress reduction and sleep promotion system based on the real-time data and user preferences. In one embodiment, the global analytics engine 754 determines whether a change in parameters of the system components 710 is necessary to optimize sleep based on the output of the simulation engine 758. If a change in parameters is necessary, the new parameters are transmitted to a mobile application on the remote device and then to the system components 710. The calibration engine 756 then updates the virtual model with the new parameters. Thus, the system autonomously optimizes the stress reduction and sleep promotion system (e.g., surface temperature) without requiring input from a user.

In another embodiment, the remote server 708 includes a reasoning engine 759 built with artificial intelligence (AI) algorithms. The reasoning engine 759 is operable to generate a reasoning model based on multiple sets of training data. The multiple sets of training data are a subset of global historical subjective data, global historical objective data, global historical environmental data, and global profile data. For example, a user's stress level and/or sleep efficiency significantly improve after engaging in an activity over a period of time, which is then included in the training data. The training data includes context data (e.g., baseline data, body sensor data) and action data (e.g., activity data, system component use). The reasoning model is updated periodically when there is an anomaly indicated in the action data produced by the reasoning data based on the context data. Each of U.S. Pat. No. 9,922,286 titled "Detecting and Correcting Anomalies in Computer-Based Reasoning Systems" and U.S. application Ser. No. 15/900,398 is incorporated herein by reference in its entirety.

Figure 4:
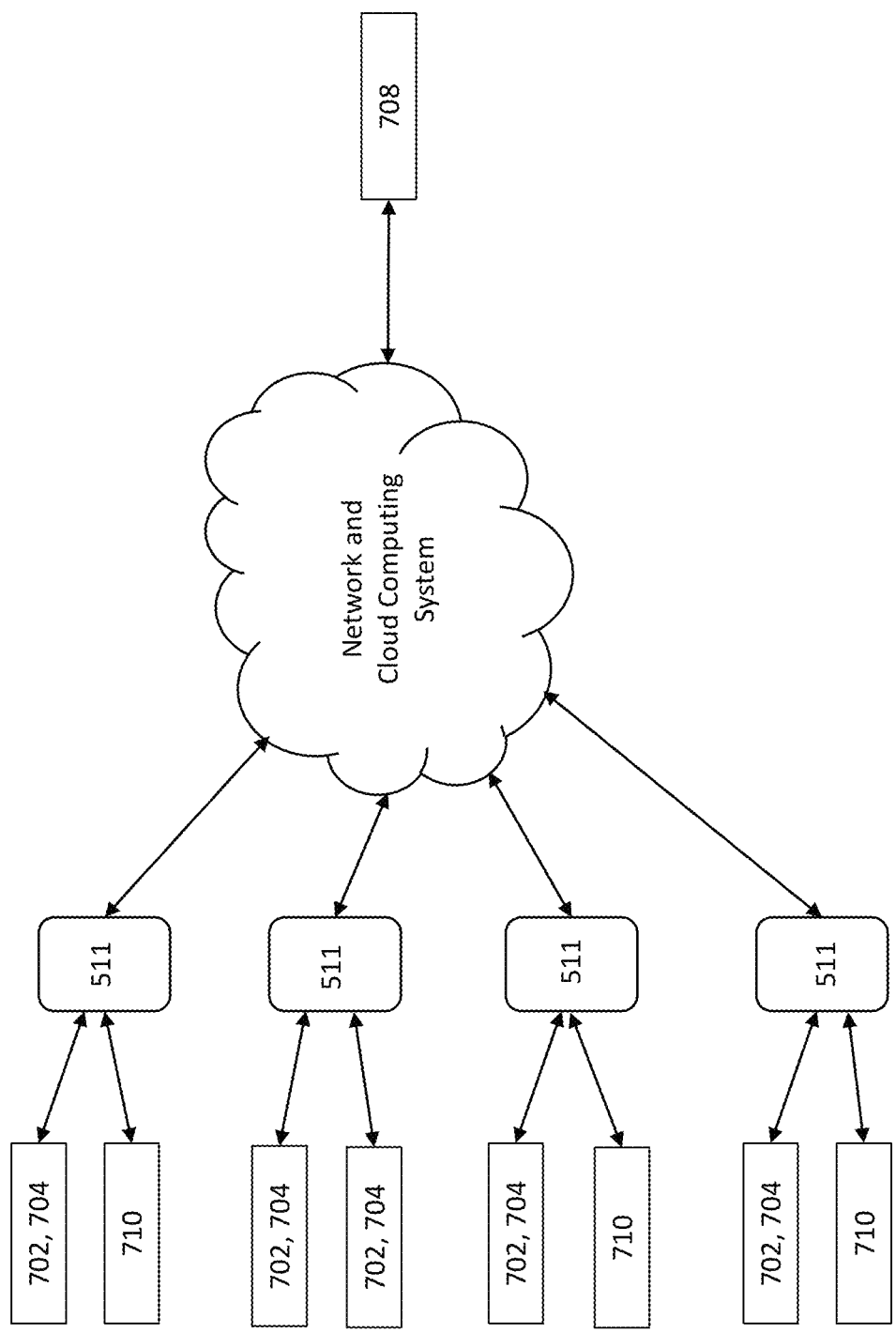
FIG. 4 is an illustration of a network of stress reduction and sleep promotion systems.

FIG. 4 is an illustration of a network of stress reduction and sleep promotion systems. Data from multiple users can be stored on a remote server 708. The remote server 708 is connected through a network and cloud computing system to a plurality of remote devices 511. Each of the plurality of remote devices 511 is connected to body sensors 702 and/or environmental sensors 704, as well as system components 710. Although one remote server is shown, it is equally possible to have any number of remote servers greater than one. A user may opt into sending their data to the remote server 708, which is stored in at least one database on the remote server 708. The simulation engine on the remote server 708 is operable to use data from the multiple users to determine customized and optimized sleep settings for the user based on personal preferences (e.g., a target number of hours of sleep, a preferred bed time, a preferred wake time, a faster time to fall asleep, fewer awakenings during the sleeping period, more REM sleep, more deep sleep, and/or a higher sleep efficiency) or physical condition (e.g., weight loss, comfort, athletic recovery, hot flashes, bed sores, depression). In one example, the temperature settings for a temperature-conditioned mattress pad for a user with hot flashes are automatically determined by the simulation engine examining data obtained from other users with hot flashes and a temperature-conditioned mattress pad stored in databases on the remote server. The simulation engine is also operable to use data from the multiple users to provide recommendations (e.g., activities, system components) to users with a similar background (e.g., gender, age, health condition).

The stress reduction and sleep promotion system includes a virtual model of the stress reduction and sleep promotion system. The virtual model is initialized based on the program selected. The virtual model of the stress reduction and sleep promotion system is dynamic, changing to reflect the status of the stress reduction and sleep promotion system in real time or near real time. The virtual model includes information from the body sensors and the environmental sensors. Based on the data from the body sensors and the environmental sensors, the virtual model generates predicted values for the stress reduction and sleep promotion system.

A sleep stage (e.g., awake, Stage N1, Stage N2, Stage N3, REM sleep) for the user is determined from the data from the body sensors.

The stress reduction and sleep promotion system is monitored to determine if there is a change in status of the body sensors (e.g., change in body temperature), the environmental sensors (e.g., change in room temperature), the system components (e.g., change in temperature of mattress pad), or sleep stage of the user. If there is a change in status, the virtual model is updated to reflect the change in status. Predicted values are generated for the stress reduction and sleep promotion system. If a difference between the optimized values and the predicted values is greater than a threshold, a simulation is run on the simulation engine to optimize the stress reduction and sleep promotion system based on the real-time data. The simulation engine uses information including, but not limited to, global historical subjective data, global historical objective data, global historical environmental data, and/or global profile data to determine if a change in parameters is necessary to optimize the stress reduction and sleep promotion system. In one example, the temperature of the mattress pad is lowered to keep a user in Stage N3 sleep for a longer period of time. In another example, the mobile application provides recommendations of an activity to a user.

As previously mentioned, the at least one remote device preferably has a user interface (e.g., a mobile application for a smartphone or tablet) that allows the stress reduction and sleep promotion system to adjust the parameters of the stress reduction and sleep promotion system. The parameters of the stress reduction and sleep promotion system (e.g., target temperatures of a mattress pad) can be manipulated through the sleeping period using a predefined program or a customized program based on user preferences to produce a deeper, more restful sleep.

Because the target temperatures may be set at any time, those target temperatures may be manipulated through the sleeping period in order to match user preferences or a program to correlate with user sleep cycles to produce a deeper, more restful sleep.

In one embodiment, the mobile application measures a time when a user began attempting to sleep (TATS), a TATS start time, a TATS end time, a time in bed (TIB), a TIB start time, and/or a TIB end time. The mobile application calculates a total TATS duration based on the TATS start time and the TATS end time. The mobile application also calculates a total TIB duration based on the TIB start time and the TIB end time. In one embodiment, the TATS start time, the TATS end time, the TIB start time, and/or the TIB end time are indicated by the user (e.g., by pressing a button in the mobile application). Alternatively, the TATS start time, the TATS end time, the TIB start time, and/or the TIB end time are determined by sensors. In one example, the TATS start time is determined by a user's eyes closing while in bed. In another example, the TATS end time is determined by increased motion as measured by a movement sensor and/or opening of the eyes. In yet another example, the TIB start time is determined by sensors indicating a user is horizontal and/or bed or room sensors indicating the user is in bed. In still another example, the TIB end time is determined by sensors indicating a user is not horizontal and/or bed or room sensors indicating the user is not in bed.

The mobile application is operable to determine whether a user is awake or asleep. The state of wakefulness (i.e., "awake") is characterized by cognitive awareness and/or consciousness, responsiveness to environmental cues, sustained movement detected by a movement sensor, beta and/or alpha waves as detected by EEG, increased heart rate, increased respiration, increased blood pressure, increased electrodermal activity, increased body temperature, open eyes, voluntary eye movements, and/or increased EMG on the chin. The state of sleep (i.e., "asleep") is characterized by loss of alertness and/or consciousness, lack of response to environmental cues, lack of movement, reduction in alpha waves as detected by EEG, increased theta and delta waves as detected by EEG, decreased heart rate, decreased respiration, decreased blood pressure, decreased body temperature, closed eyes, eye twitches, and/or decreased oxygen saturation.

In a preferred embodiment, the mobile application is operable to measure an initial sleep onset time and/or a final awakening time. The initial sleep onset time is a first occurrence of sleep after the TATS start time. The final awakening time is a time immediately after the last occurrence of sleep before the TATS end time. In one embodiment, the mobile application calculates a latency to sleep onset as the duration of a time interval between the TATS start time to the initial sleep onset time. In another embodiment, the mobile application calculates a latency to arising as the duration of a time interval between the final awakening time to the TATS end time. In a preferred embodiment, the mobile application is operable to calculate a sleep efficiency percentage. In one embodiment, the sleep efficiency percentage is defined as the total sleep time divided by the total TATS duration. In an alternative embodiment, the sleep efficiency percentage is defined as the total sleep time divided by the total TIB duration.

In one embodiment, the mobile application is operable to determine a total sleep period duration, a total sleep time, a sleep maintenance percentage, a total wakefulness duration, a wakefulness duration after initial sleep onset, a total number of awakenings, an awakening rate per hour, and/or a sleep fragmentation rate.

In another embodiment, the mobile application is operable to determine REM sleep, N1 sleep, N2 sleep, and/or N3 sleep. REM sleep is characterized by low-voltage, mixed-frequency EEG activity with less than 15 seconds of alpha activity, saw-tooth theta EEG activity, rapid eye movements, and/or decreased or absent EMG activity on the chin. N1 sleep is characterized by low-voltage, mixed-frequency EEG activity with less than 15 seconds of alpha activity in a 30-second epoch, no sleep spindles or K complexes, possible slow rolling eye movements, and/or diminished EMG activity on the chin. N2 sleep is characterized by sleep spindle and/or K complex activity, absence of eye movements, and/or diminished EMG activity on the chin. N3 sleep is characterized by high amplitude (e.g., greater than 75 µV peak-to-peak), slow wave (e.g., frequency of 4 Hz or less) EEG activity. In yet another embodiment, the mobile application is operable to calculate REM sleep duration, percentage, and latency from sleep onset; N1 sleep duration, percentage, and latency from sleep onset; N2 sleep duration, percentage, and latency from sleep onset; and/or N3 sleep duration, percentage, and latency from sleep onset.

Alternatively, the calculations and determining of sleep states described above are determined over the network on a remote server. In one embodiment, the calculations and determining of sleep states are then transmitted to at least one remote device. In yet another embodiment, the calculations and determining of sleep states described above are determined using third party software and transmitted to the mobile application.

The mobile application preferably serves as a hub to interface with the system components, the body sensors, the environmental sensors, and/or at least one third-party application (e.g., APPLE HEALTH, MYFITNESSPAL, nutrition tracker). The mobile application is operable to obtain data from a mattress pad (e.g., OOLER) and/or a wearable (e.g., OURA, APPLE WATCH, FITBIT, SAMSUNG GALAXY WATCH). The mobile application is operable to recognize patterns the user does not already see and help guide them to a new pattern. For example, many nutrition trackers monitor food and water intake and set daily and long-term calorie and weight goals. However, these nutrition trackers do not combine this information with additional data. In one example, data from the nutrition tracker is combined with GPS information to prompt a user before they eat fast food. The mobile application uses the chatbot to interact with the user before they eat fast food (e.g., positive quote, breathing exercise, reminder about goals). Additionally, the mobile application encourages the user to add the food into the mobile application and/or third-party application before they eat so the user is aware of what they are consuming. The mobile application also is operable to propose a meal for the user and/or an exercise plan that allows the user to meet goals or minimize damage from the fast food.

Additionally, the mobile application uses cognitive behavioral therapy (CBT) with artificial intelligence (AI) to help a user make incremental changes to improve sleep and health. CBT relies on three components: actions, thoughts, and feelings. The mobile application encourages activities, positive thoughts, and social interaction to increase happiness and decrease depression. The mobile application preferably uses a chatbot to interact with the user. Alternatively, the mobile application has at least one coach to interact with the user. The mobile application is operable to provide repetitive coaching, which is necessary for long-term habit change. For example, the mobile application reminds a user to take a vitamin every morning until the user begins logging the action on their own. The mobile application also reminds the user to take the vitamin when the user does not log the action. The mobile application is also operable to assist a user in creating positive coping mechanisms to manage and diffuse stress daily. For example, the mobile application learns over time that the user enjoys walking for stress relief. When the mobile application detects that a user is stressed, the mobile application recommends taking a walk. Further, the mobile application is operable to understand natural language voices, converse with the user, and execute voice commands.

The mobile application uses machine learning to identify positive behaviors, negative behaviors, antecedents or causes of positive behaviors, antecedents or causes of negative behaviors, triggers, early or past experiences that impact current behavior, and/or core belief structures and patterns. The mobile application is also operable to use machine learning to identify timing of the positive behaviors, the negative behaviors, the antecedents or causes of positive behaviors, the antecedents or causes of negative behaviors, and/or the triggers. The timing is a daily, weekly, monthly, or other interval (e.g., two weeks, six weeks) basis.

The mobile application also uses machine learning to identify patterns of habits and behaviors. For example, the mobile application is operable to determine when to push notifications based on when a user is likely to be looking at their phone (e.g., before work, during lunch, after work). The mobile application is also operable to determine when a user is stressed (e.g., via user identification and/or sensor data). In one embodiment, the machine learning incorporates information, including, but not limited to, mobile phone usage, mobile application usage, GPS location, and/or sensor data.

In one embodiment, the mobile application updates the machine learning models via feedback from a user, a friend, a family member, a healthcare provider, and/or an expert (e.g., nutritionist, sleep coach, trainer, therapist, fitness coach).

In one embodiment, the mobile application asks the user to identify at least one problem the user wants to improve. The mobile application is operable to identify patterns, triggers, and stimuli for stress. In another embodiment, the mobile application is operable to analyze the at least one problem to determine which one of the at least one problem is easiest for the user to remedy. In one example, the mobile application prioritizes the one of the at least one problem. Advantageously, this allows the user to experience success with achieving a goal, providing motivation to tackle additional problems. The mobile application is operable to document a user's progress over time. In one embodiment, the mobile application provides positive feedback to a user when goals are achieved. In another embodiment, the mobile application is operable to designate at least one goal based on an amount of time to achieve the at least one goal (e.g., short term goal, medium term goal, long term goal).

In another embodiment, the mobile application provides a journaling component. In one example, a user is worried about financial problems, which can be dealt with via budget, planning, and/or organization tips via the mobile application. However, the journaling component provides a way to document and validate the user's stress, allowing the user to focus on other tasks during the day and sleep at night. In one embodiment, the journaling component includes a gratitude journal.

The mobile application preferably provides a social network component for a user to interact with other users with similar interests or health conditions. In one embodiment, the mobile application identifies at least one group for a user based on health markers, mental health markers, goals, age, gender, social and economic groups, religion, etc. The social network component also allows for the creation of sharing groups that promote trust. In one example, the mobile application allows for the creating of a sharing group dedicated to domestic abuse survivors to provide emotional support to members of the group. Further, patterns of response trigger movement between groups. For example, a user with social anxiety falls into multiple groups, but based on their response to interventions and the types of interventions that are having success, the prediction of what will help the most and, therefore, the group assignment will change. In another example, an overweight user with sleep apnea who loses weight and remedies the sleep apnea naturally will move out of the sleep apnea group after the weight loss. However, that user may also move into a group that focuses on social anxiety and/or using food as a coping mechanism. Additionally, the social network component allows for a user to challenge other users to complete activities.

The mobile application allows a user to identify stress, label the source of the stress, and put users into patterns of emotions, thoughts, and behaviors to categorize intervention suggestions. In one example, a user suffers from social anxiety and, therefore, avoids phone calls and large group events. The mobile application allows a user to rank activities based on stress level (e.g., scale from 1 to 10). The mobile application provides suggestions for how to manage stress and requests feedback from the user to identify what is working. For example, the mobile application encourages a user to meditate both before and after a large group event. Additionally, the mobile application provides a checklist and measurements for success.

In another example, the mobile application assists a user through a death. Based on time and patterns for grief (e.g., Kübler-Ross model), the mobile application encourages a user through the process of healing. The mobile application includes visualization exercises (e.g., visualizing putting bigger hurts in a closet and taking them out in small moments). The mobile application is operable to map a tree of support (e.g., family, friends, other users of the mobile application). The mobile application provides a positive quote, encourages meditation, and/or encourages a walk when the user is having a bad day (e.g., as noted by the user and/or detected by sensors).

In a preferred embodiment, the mobile application includes geolocation data. The geolocation data allows for targeted suggestions that are relevant to a user's location. For example, the mobile application suggests activities (e.g., races, events) located near the user. Additionally, geolocation data allows for tracking activity and behaviors by location. For example, the geolocation data allows for analysis of sleep, stress, and health (e.g., mental health) patterns for users in Alaska versus users located near the equator.

FIG. 5 illustrates a welcome screen for one embodiment of a GUI for a mobile application. The welcome screen allows a user to sign up for an account or log in to an established account. FIG. 6 illustrates an account creation screen for one embodiment of a GUI for a mobile application. The user enters a name (e.g., first and last), an email address, and a password. FIG. 7 illustrates the account creation screen with the user information added.

Figure 10:
FIG. 10 illustrates an example of a GUI describing how incremental changes in lifestyle add time to a user's life.
Figure 9:
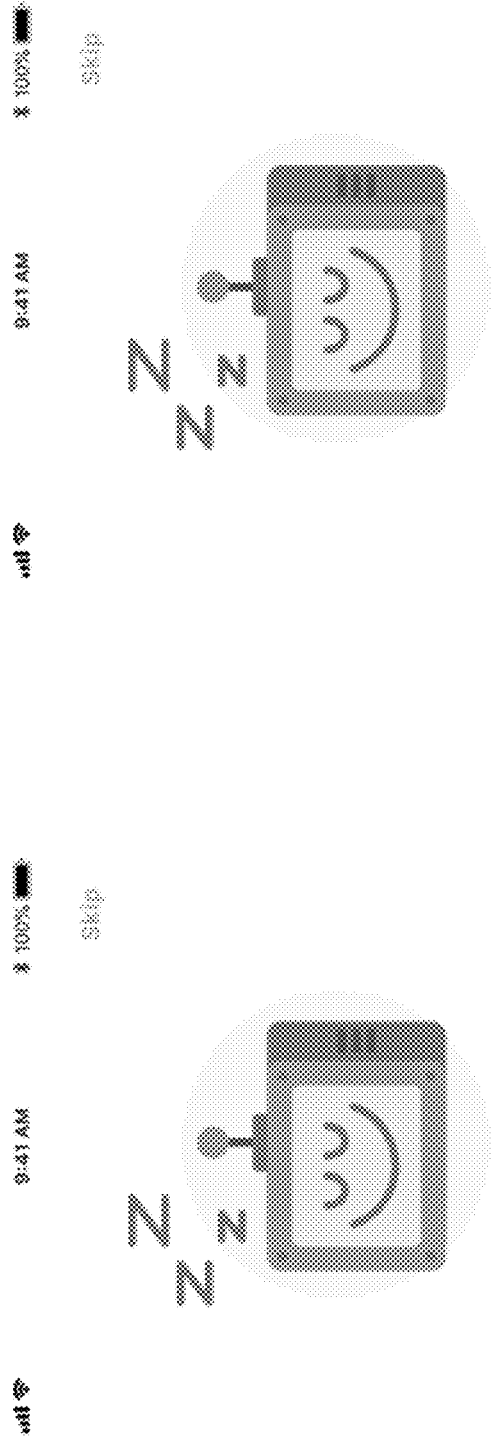
FIG. 9 illustrates an example of a GUI describing the relationship between stress and sleep.
Figures 11, 12:
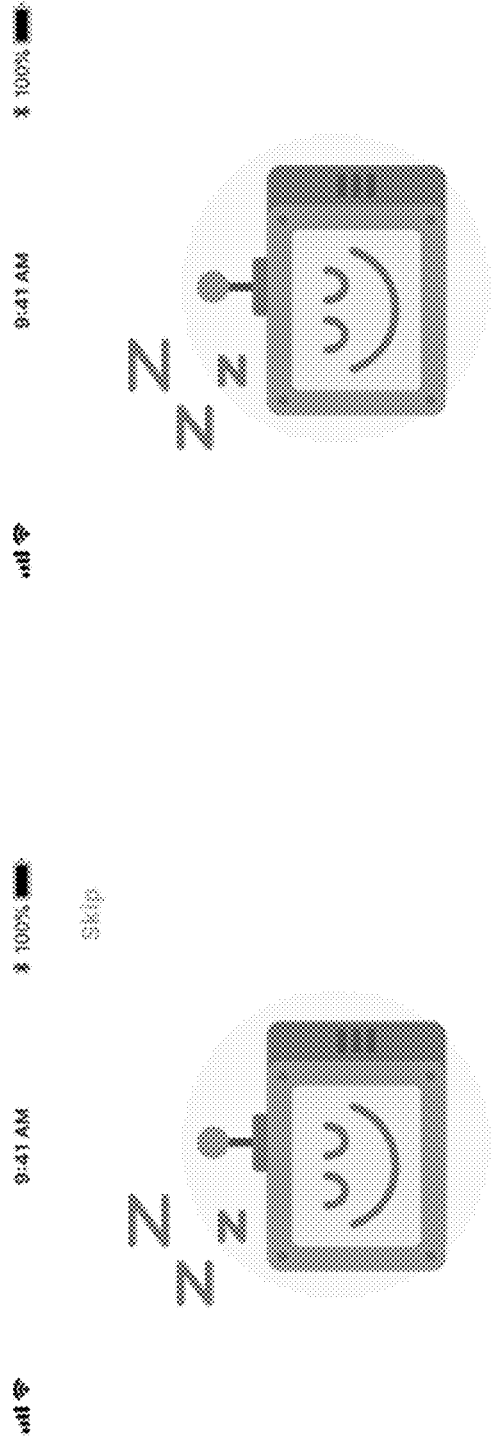
FIG. 11 illustrates an example of a GUI describing the combination of science, sleep, diet, and exercise adds time to a user's life.
FIG. 12 illustrates an example of a GUI describing the mobile application as a technological assistant to improve quality of life.

FIGS. 8-12 illustrate examples of onboarding screens for one embodiment of a GUI for a mobile application. FIG. 8 illustrates an example of a GUI describing benefits of using the mobile application. FIG. 9 illustrates an example of a GUI describing the relationship between stress and sleep. FIG. 10 illustrates an example of a GUI describing how incremental changes in lifestyle (e.g., mindfulness activities, sleep improvement, stress reduction) add time to a user's life. FIG. 11 illustrates an example of a GUI describing the combination of science, sleep, diet, and exercise adds time to a user's life. FIG. 12 illustrates an example of a GUI describing the mobile application as a technological assistant to improve quality of life (e.g., less stress, more sleep).

Figure 14:
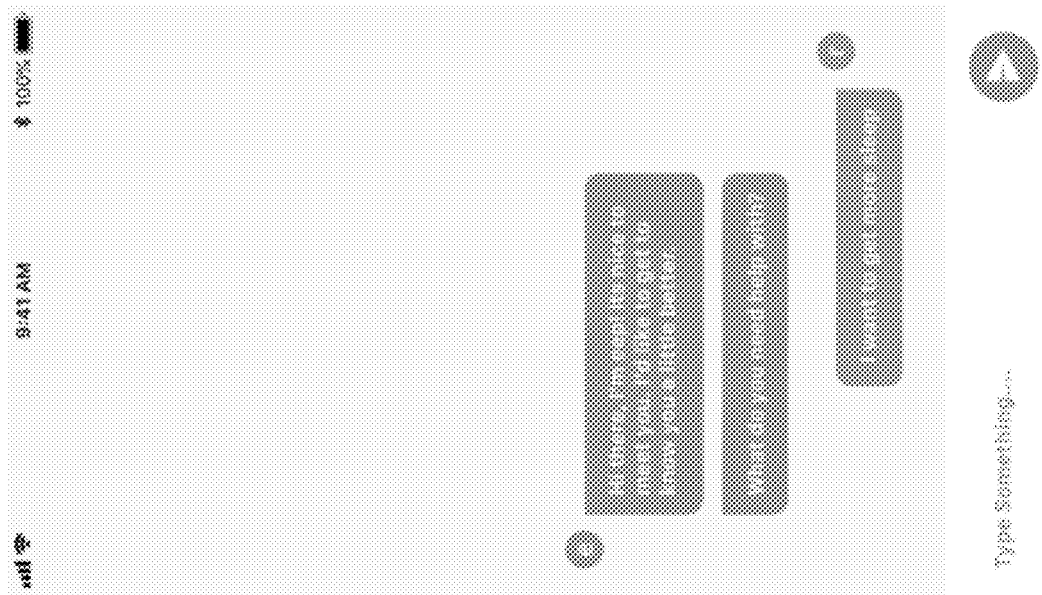
FIG. 14 illustrates an example of a chat where the user requests help getting more sleep.
Figure 13:
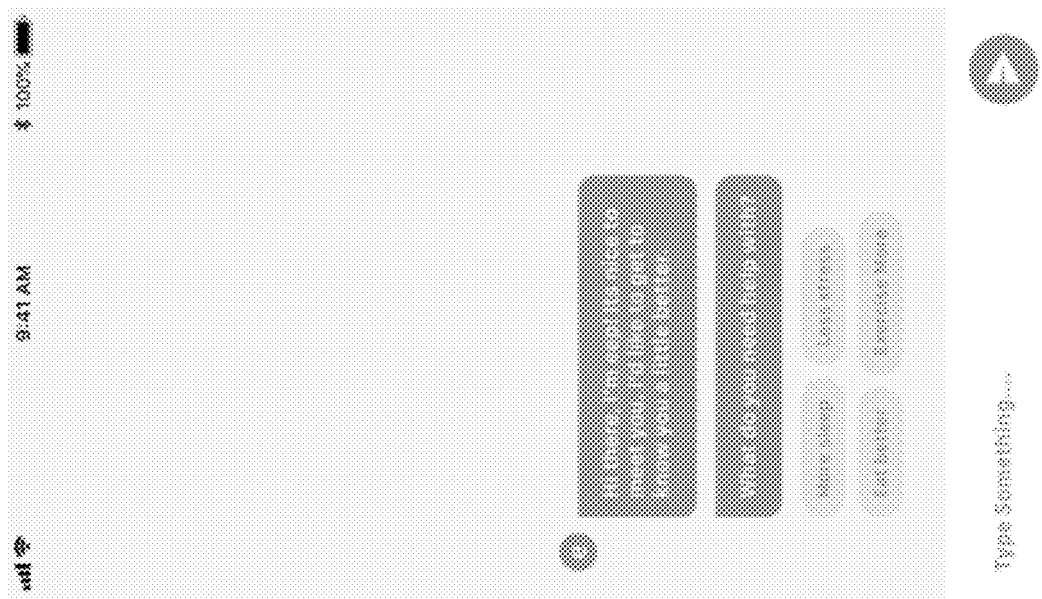
FIG. 13 illustrates an example of a chat where a chatbot asks what the user needs help with and provides buttons to select a topic.
Figure 16:
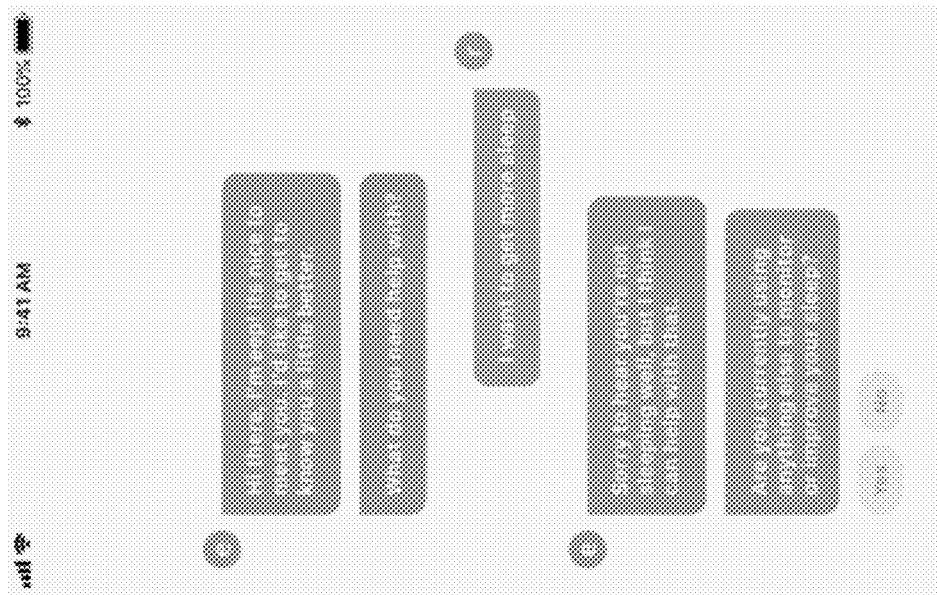
FIG. 16 illustrates an example of a chat where the chatbot allows a user to select yes or no in response to the question in FIG. 15.
Figure 15:
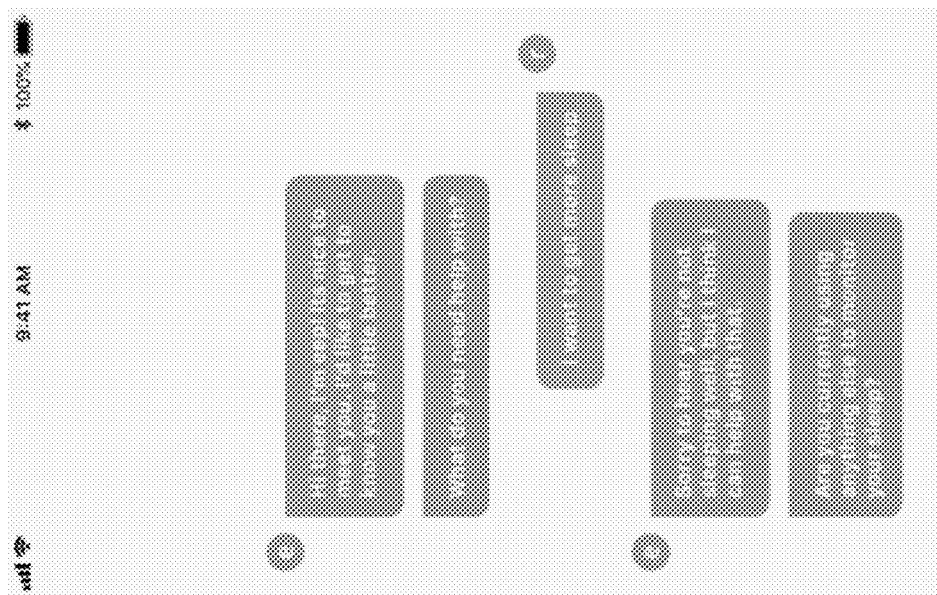
FIG. 15 illustrates an example of a chat where the chatbot asks if the user is currently using anything to monitor their sleep.
Figure 18:
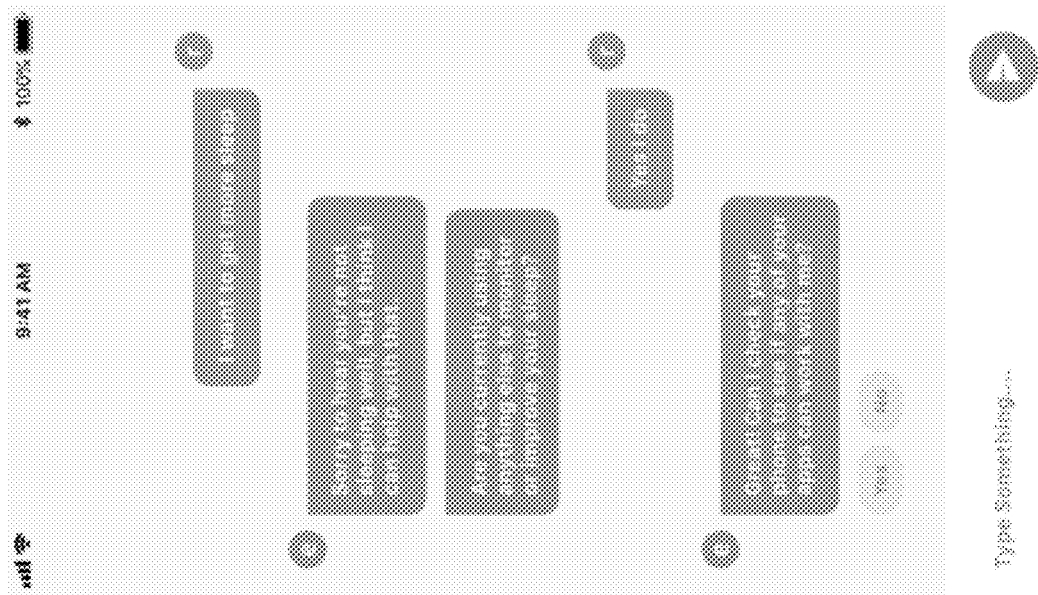
FIG. 18 illustrates an example of a chat where the chatbot asks if the mobile application can check the mobile device for other applications compatible with the mobile application.
Figure 17:
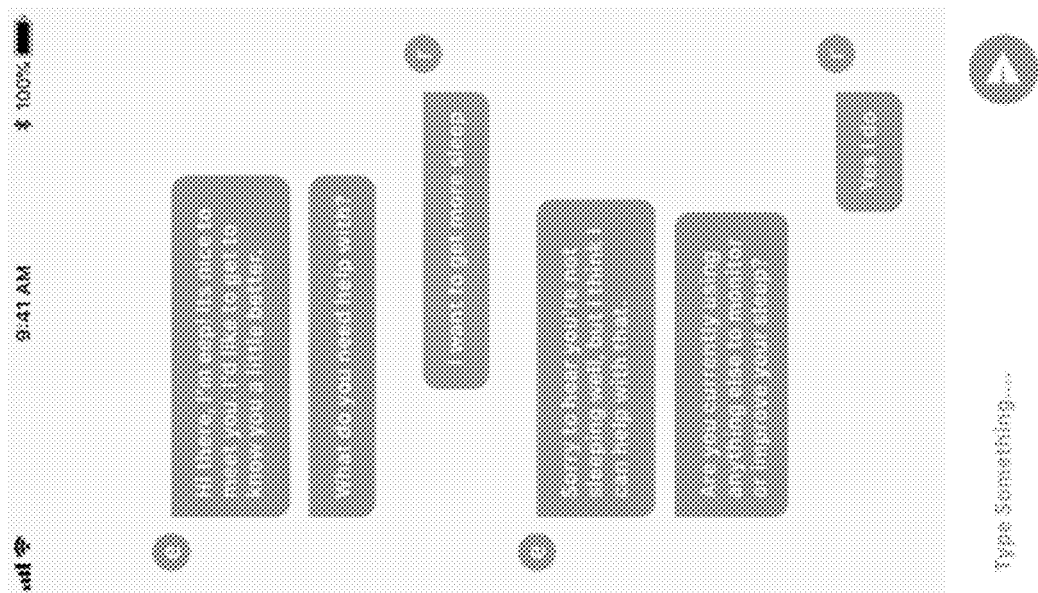
FIG. 17 illustrates an example of a chat where the user's response to the question in FIG. 15 is recorded.
Figure 20:
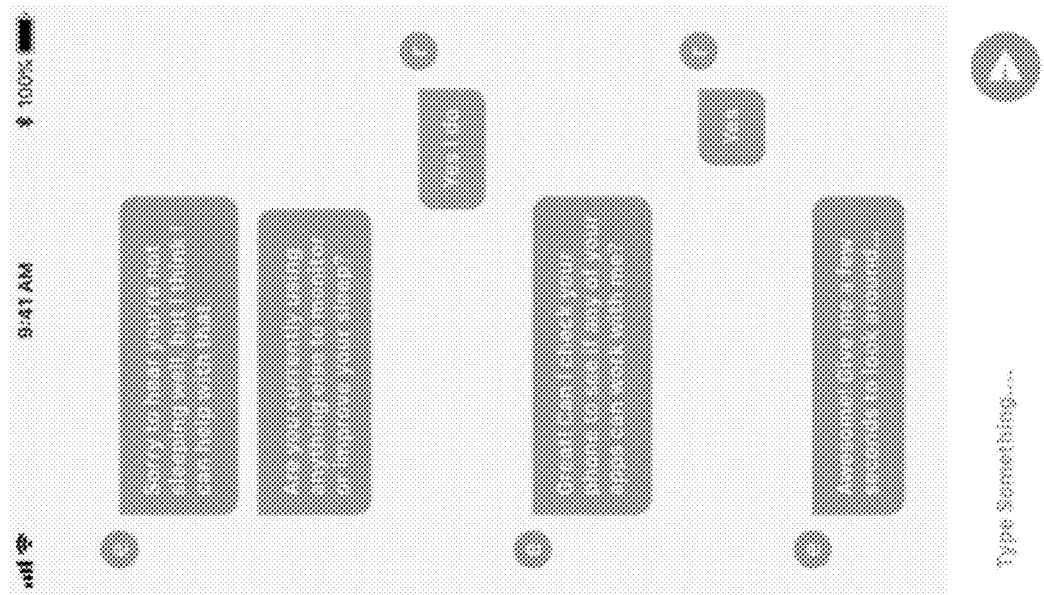
FIG. 20 illustrates an example of a chat where the chatbot thanks the user for the response and communicates that the mobile application is looking for other compatible applications.
Figure 19:
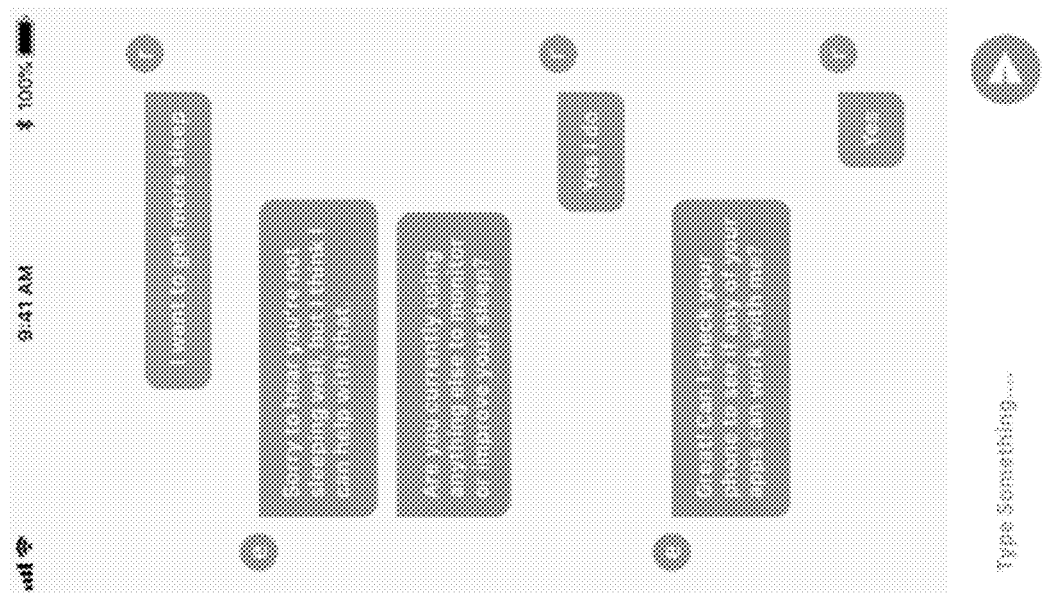
FIG. 19 illustrates an example of a chat where the user's response to the question in FIG. 18 is recorded.

FIGS. 13-20 illustrate examples of an onboarding chat for one embodiment of a GUI for a mobile application. FIG. 13 illustrates an example of a chat where a chatbot asks what the user needs help with and provides buttons to select a topic (e.g., more sleep, less stress, eat better, exercise more). FIG. 14 illustrates an example of a chat where the user requests help getting more sleep. FIG. 15 illustrates an example of a chat where the chatbot asks if the user is currently using anything to monitor their sleep. FIG. 16 illustrates an example of a chat where the chatbot allows a user to select yes or no in response to the question in FIG. 15. FIG. 17 illustrates an example of a chat where the user's response to the question in FIG. 15 is recorded. FIG. 18 illustrates an example of a chat where the chatbot asks if the mobile application can check the mobile device (e.g., phone, tablet) for other applications compatible with the mobile application. The chatbot allows a user to select yes or no in response to the question. FIG. 19 illustrates an example of a chat where the user's response to the question in FIG. 18 is recorded. FIG. 20 illustrates an example of a chat where the chatbot thanks the user for the response and communicates that the mobile application is looking for other compatible applications.

The mobile application is operable to determine a user's preferences over time. For example, if the user never selects running as a physical option, the chatbot asks why the user does not like to run. The chatbot allows a user to select a response (e.g., it hurts, don't like it, no place to do it). The chatbot is operable to provide a suggestion based on the user's response. For example, if the user selects "no place to do it", the chatbot may provide suggestions of gyms and/or free recreational facilities near the user's work or home. As the mobile application learns more about a user's preferences and health, the mobile application can use machine learning (e.g., via the reasoning engine) to make better predictions about what would help the user.

Figure 22:
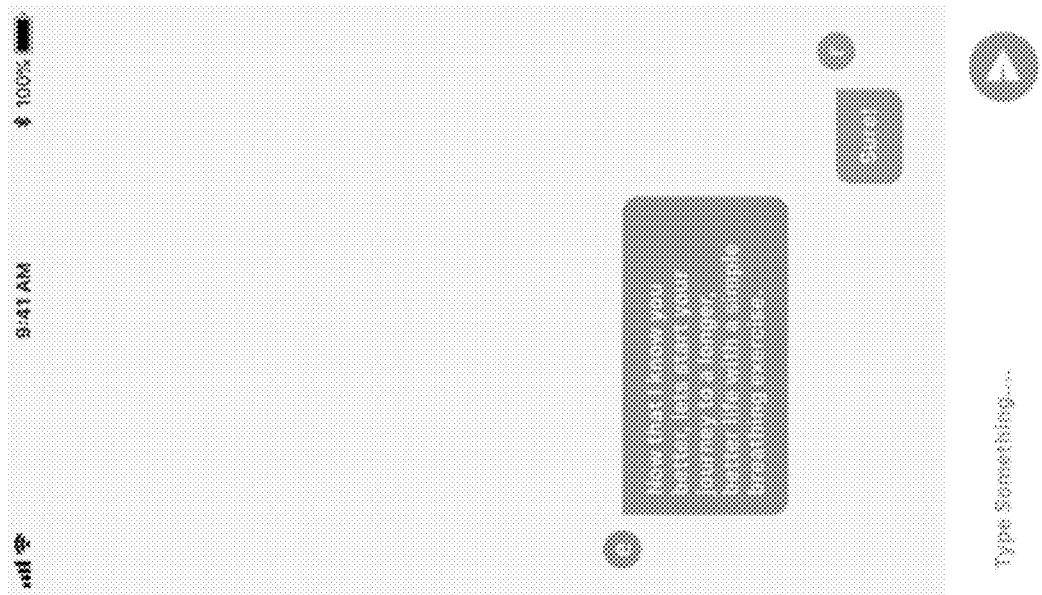
FIG. 22 illustrates an example of a chat where the user's response to the question in FIG. 21 is recorded.
Figure 21:
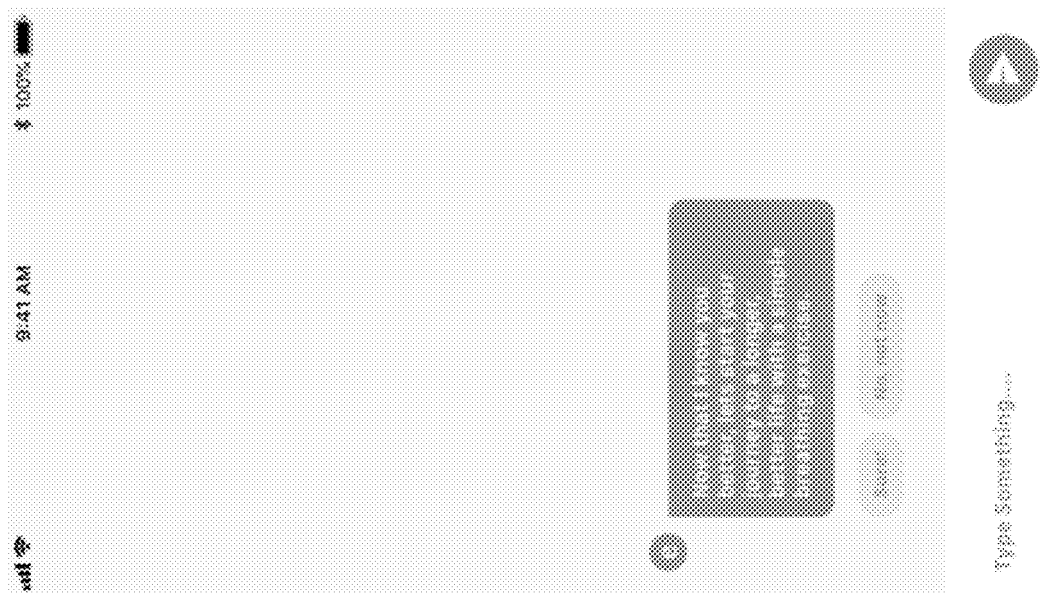
FIG. 21 illustrates an example of a chat where the chatbot asks if the user would like to complete a breathing exercise.
Figure 23:
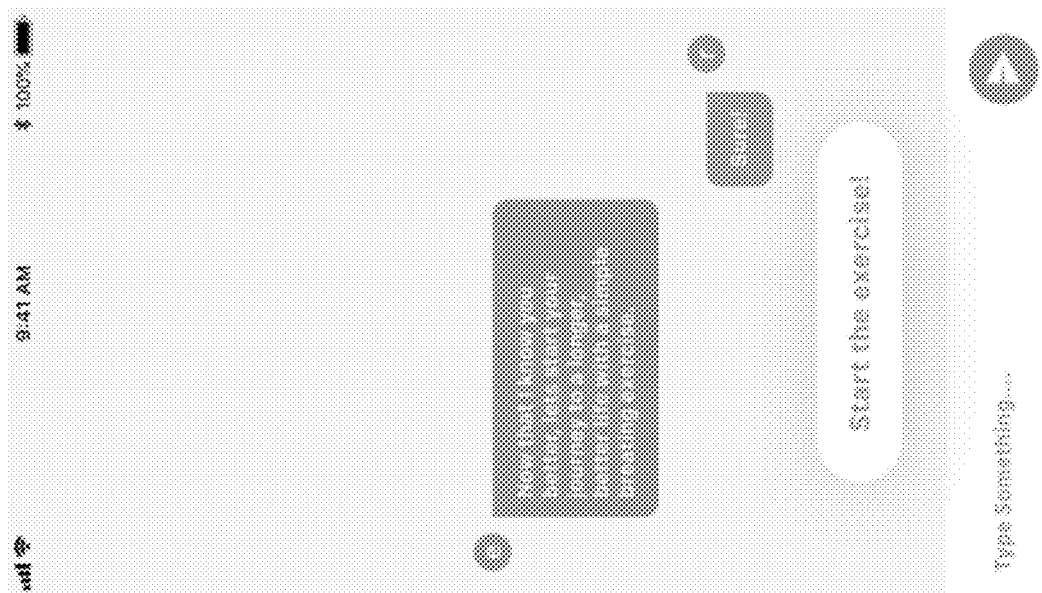
FIG. 23 illustrates an example of a chat where the chatbot allows the user to start the exercise.

FIGS. 21-23 illustrate examples of a breathing exercise chat for one embodiment of a GUI for a mobile application. FIG. 21 illustrates an example of a chat where the chatbot asks if the user would like to complete a breathing exercise. The chatbot allows a user to select a positive or negative response (e.g., yes or no) in response to the question. FIG. 22 illustrates an example of a chat where the user's response to the question in FIG. 21 is recorded. FIG. 23 illustrates an example of a chat where the chatbot allows the user to start the exercise.

Figure 24:
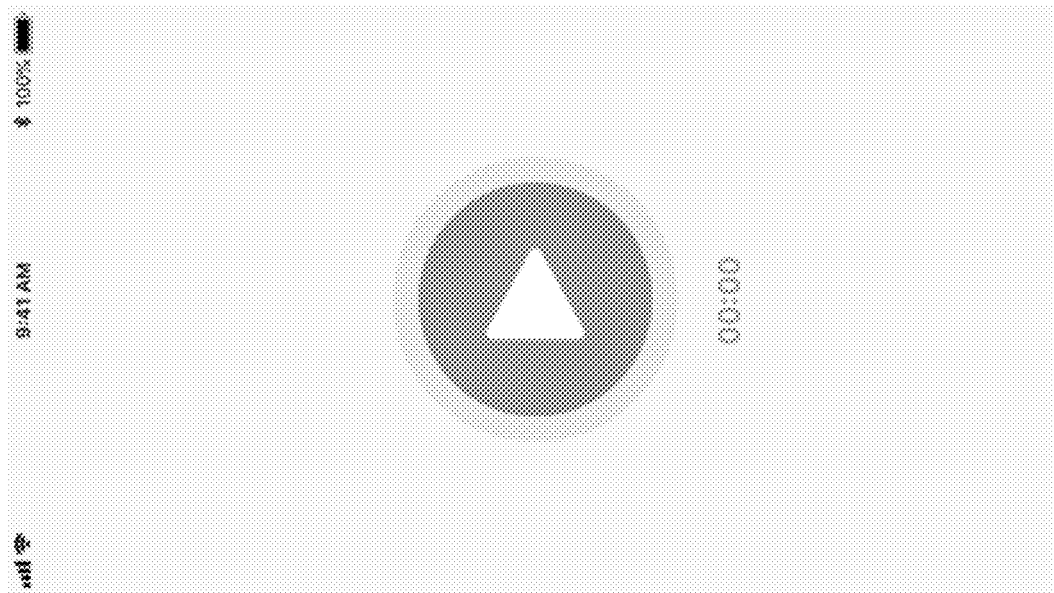
FIG. 24 illustrates an example of a start screen for a breathing exercise.
Figure 26:
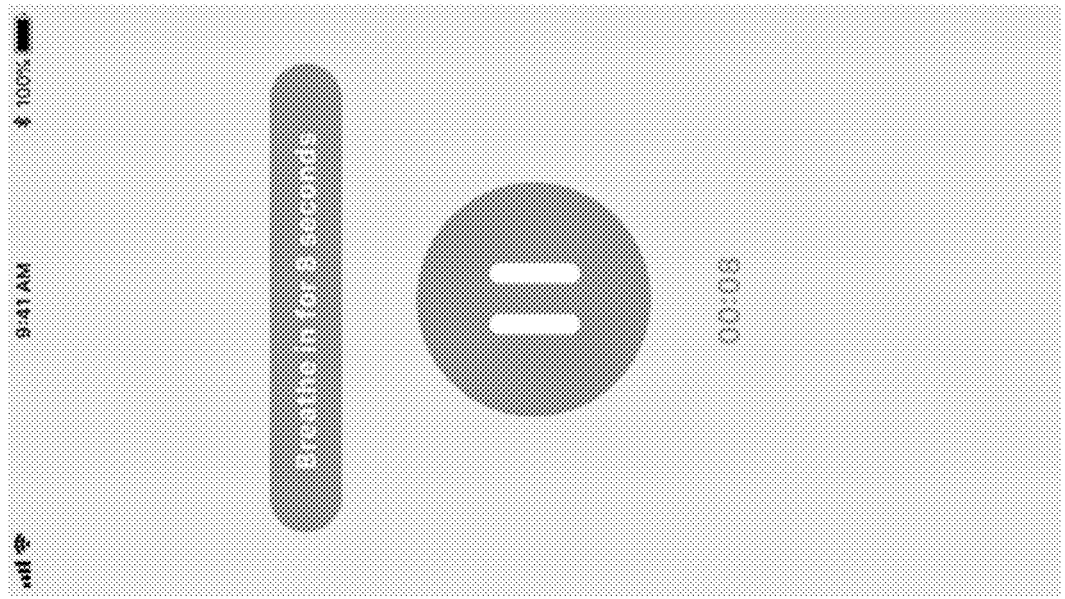
FIG. 26 illustrates another example of a breathing exercise in progress.
Figure 25:
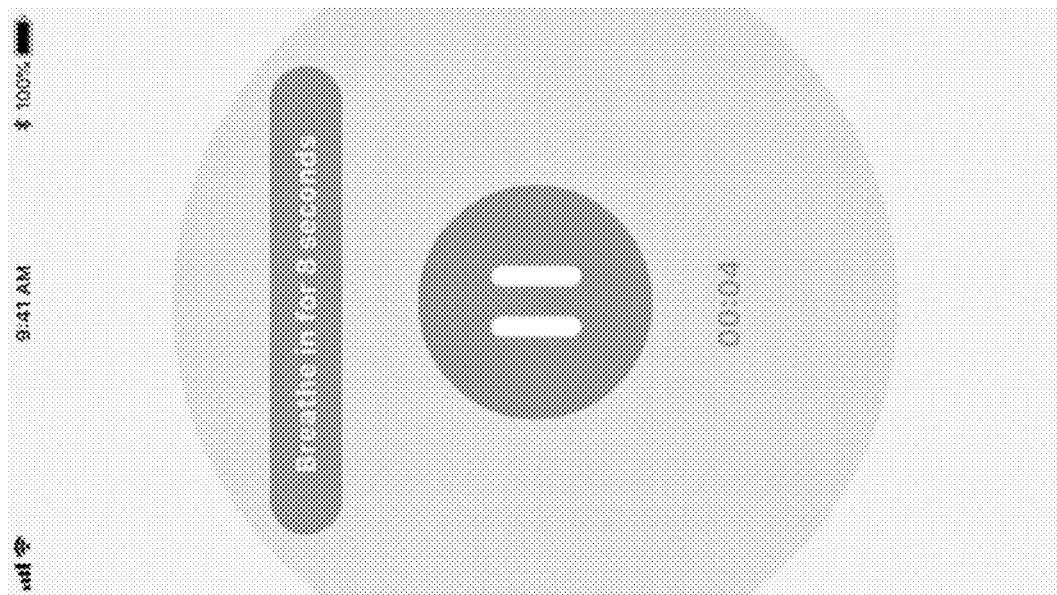
FIG. 25 illustrates an example of a breathing exercise in progress.
Figure 28:
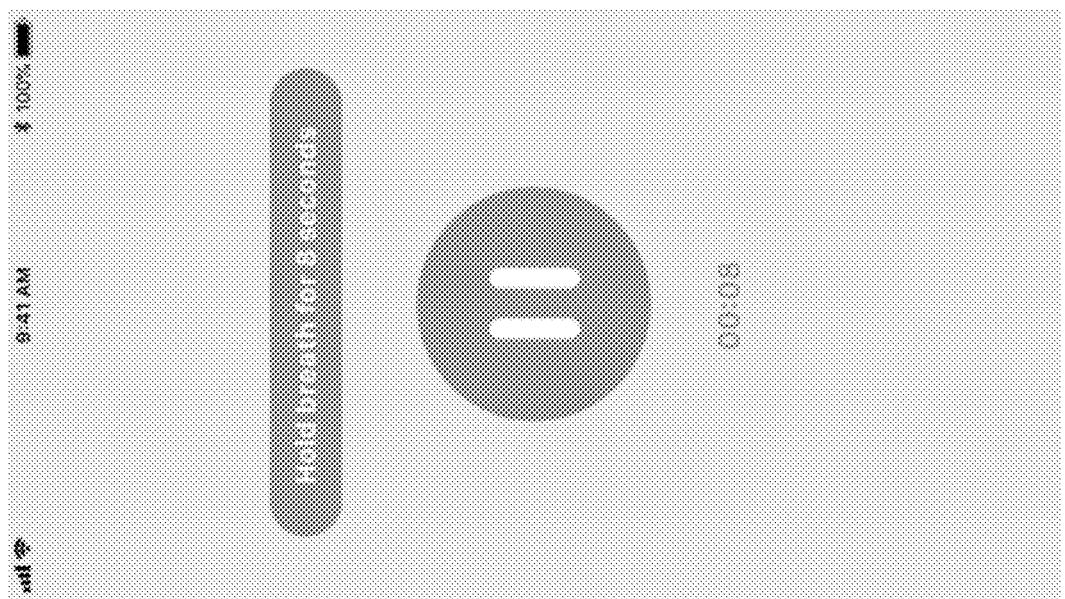
FIG. 28 illustrates still another example of a breathing exercise in progress.
Figure 27:
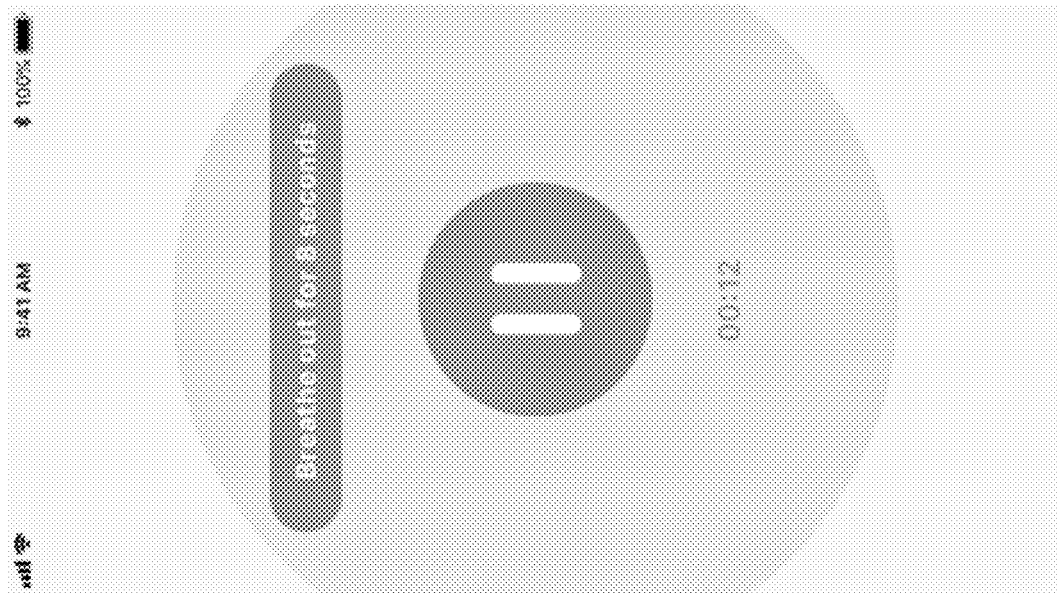
FIG. 27 illustrates yet another example of a breathing exercise in progress.
Figure 29:
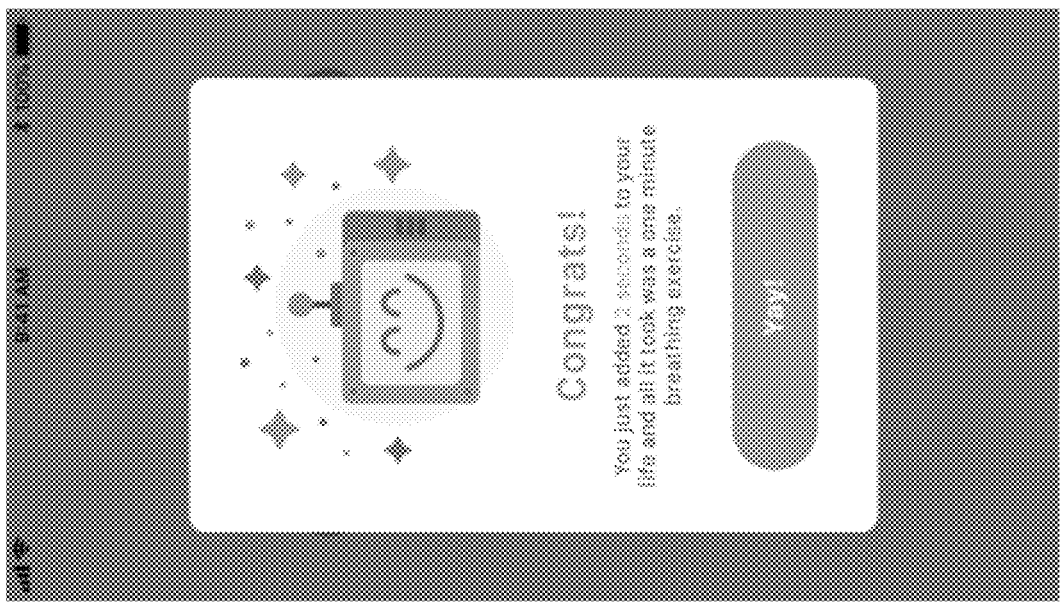
FIG. 29 illustrates a congratulations screen for completing the breathing exercise.

FIGS. 24-29 illustrate examples of a breathing exercise for one embodiment of a GUI for a mobile application. FIG. 24 illustrates an example of a start screen for a breathing exercise. The breathing exercise begins when the play button is pressed. FIG. 25 illustrates an example of a breathing exercise in progress (e.g., 4 seconds into breathing in for 8 seconds). FIG. 26 illustrates another example of a breathing exercise in progress (e.g., 8 seconds into breathing in for 8 seconds). FIG. 27 illustrates yet another example of a breathing exercise in progress (e.g., hold breath for 8 seconds). FIG. 28 illustrates still another example of a breathing exercise in progress (e.g., breathe out for 8 seconds). FIG. 29 illustrates a congratulations screen for completing the breathing exercise.

Figure 30:
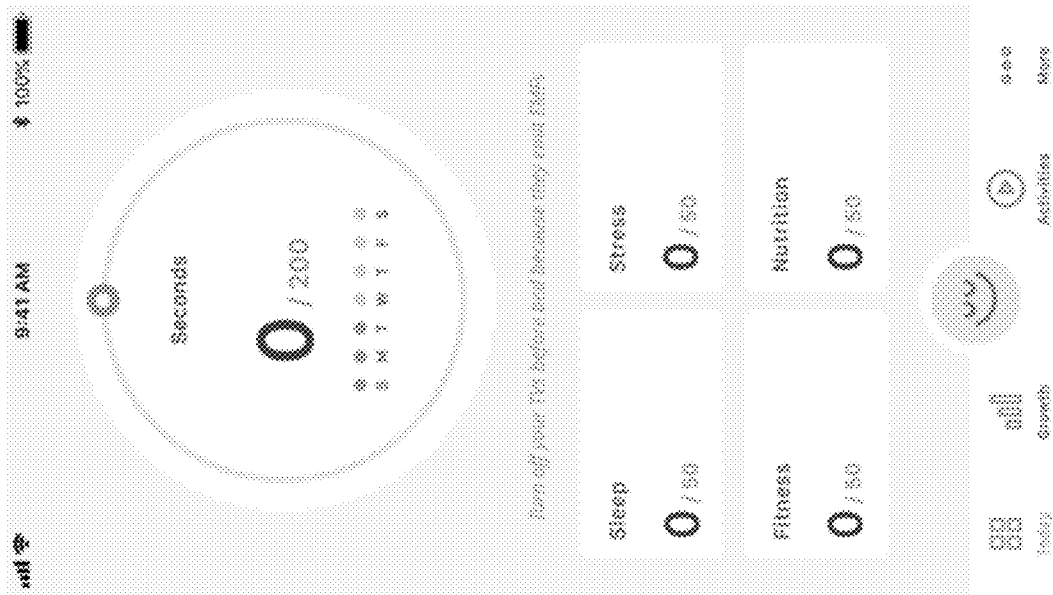
FIG. 30 illustrates an example of a dashboard at the start of a day.
Figure 32:
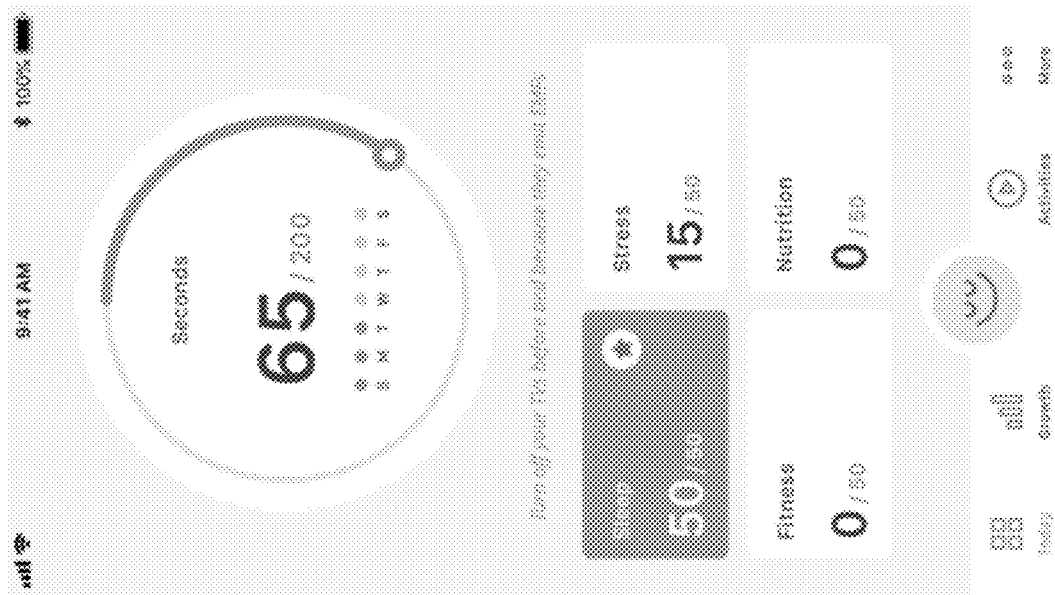
FIG. 32 illustrates an example of a dashboard with 65 seconds added.
Figure 31:
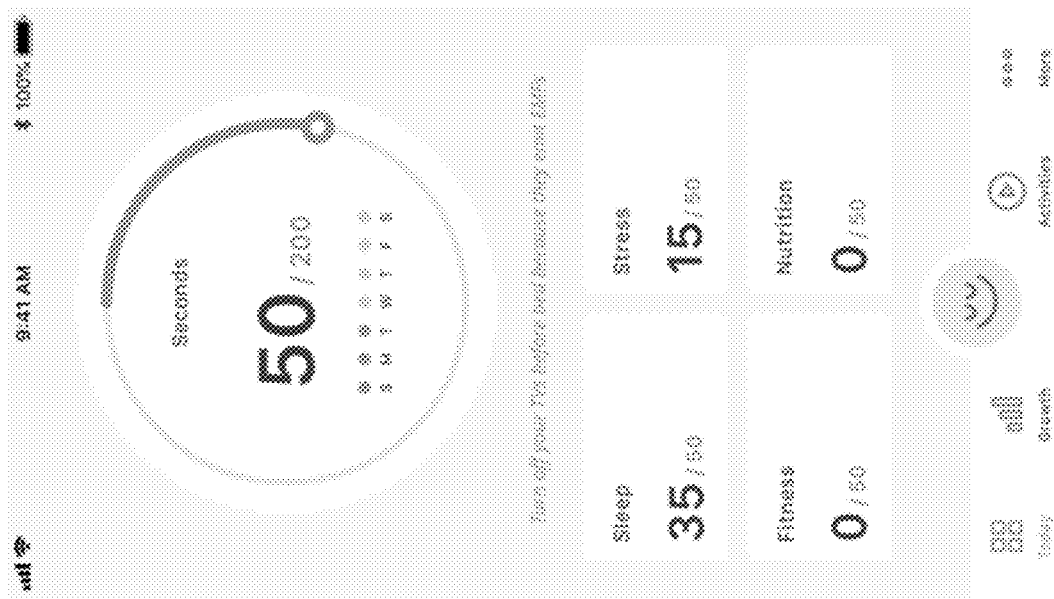
FIG. 31 illustrates an example of a dashboard with 50 seconds added.
Figure 33:
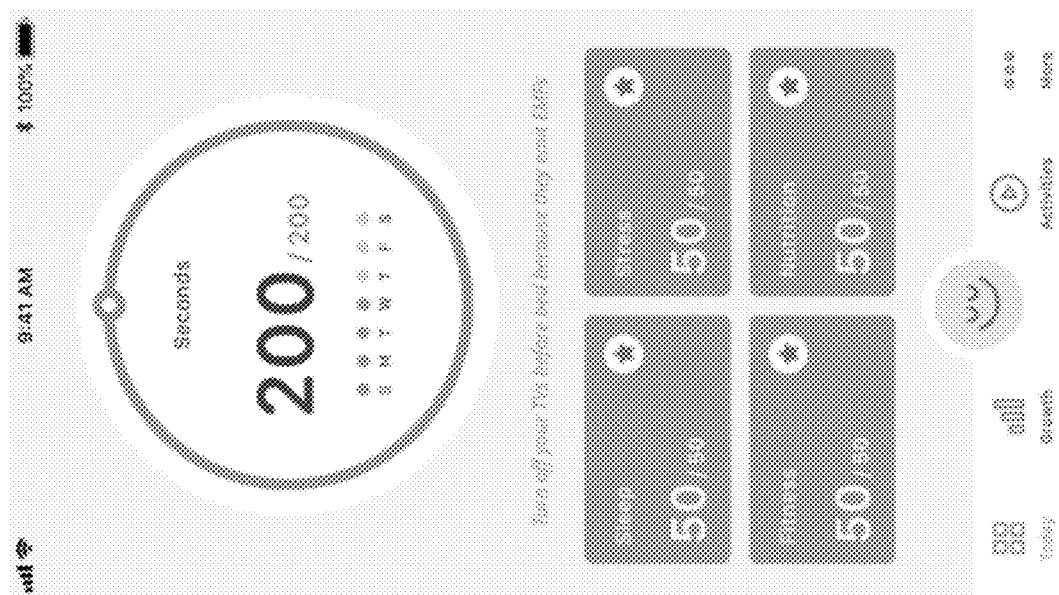
FIG. 33 illustrates an example of a dashboard with 200 seconds added.

FIGS. 30-33 illustrate examples of a dashboard for one embodiment of a GUI for a mobile application. In a preferred embodiment, the mobile application tracks a number of seconds (e.g., 200) added to a life due to healthy choices. FIG. 30 illustrates an example of a dashboard at the start of a day. FIG. 31 illustrates an example of a dashboard with 50 seconds added. FIG. 32 illustrates an example of a dashboard with 65 seconds added. FIG. 33 illustrates an example of a dashboard with 200 seconds added.

Figure 34:
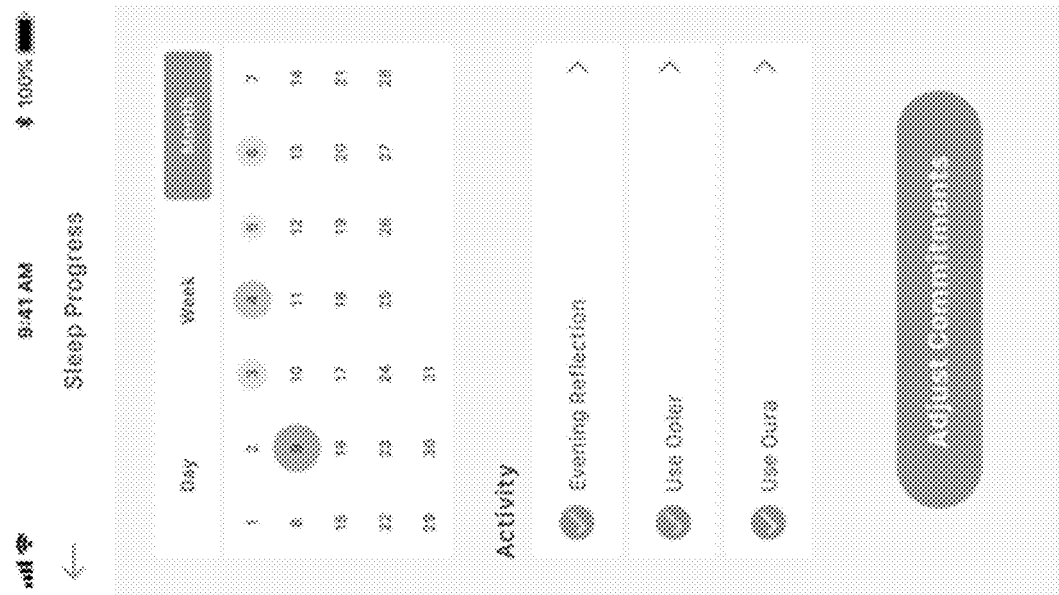
FIG. 34 illustrates an example of a month view of a sleep progress screen.
Figures 35, 36:
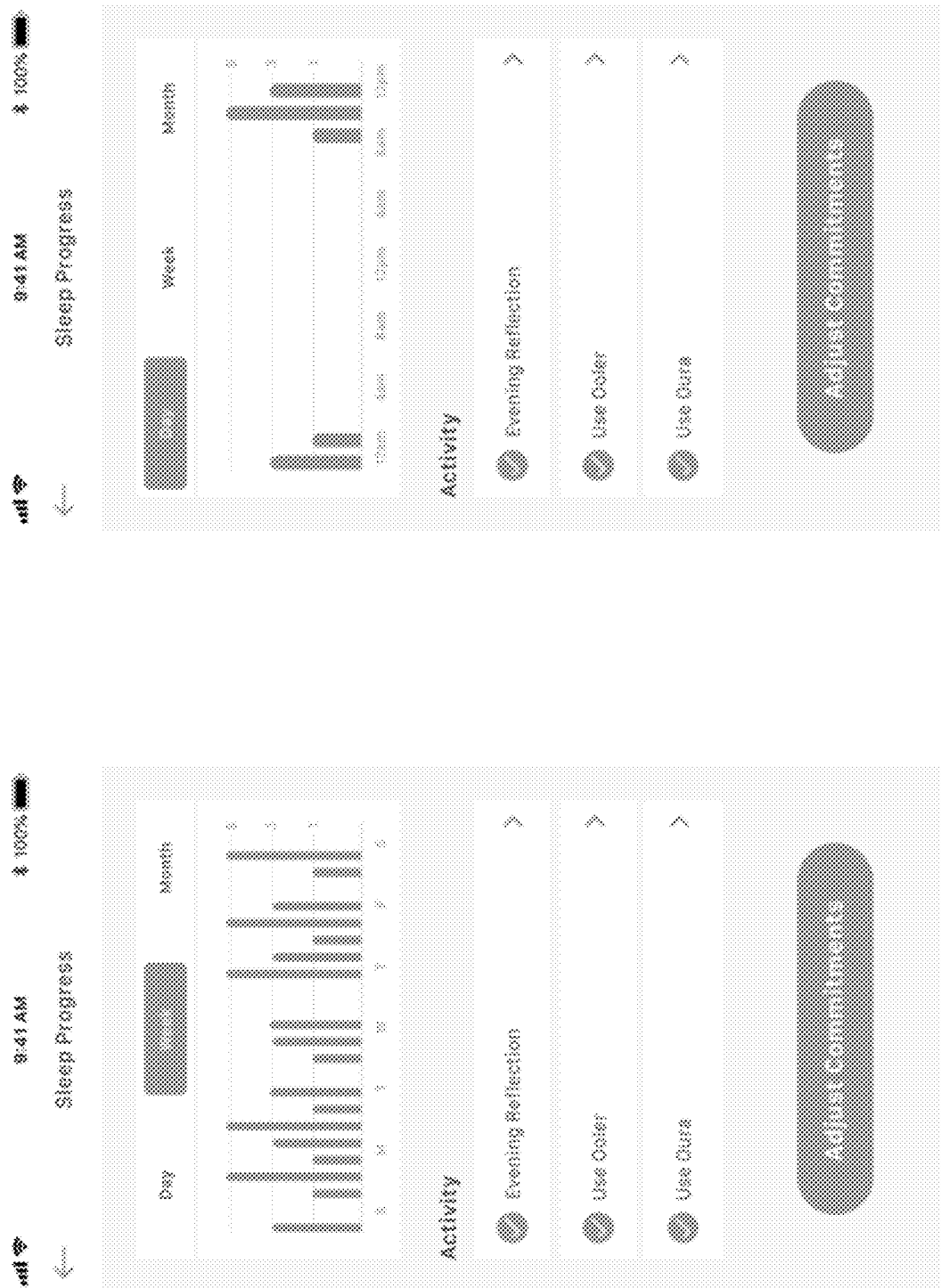
FIG. 35 illustrates an example of a week view of a sleep progress screen.
FIG. 36 illustrates a daily view of a sleep progress screen.

FIGS. 34-36 illustrate examples of a sleep progress screen for one embodiment of a GUI for a mobile application. FIG. 34 illustrates an example of a month view of a sleep progress screen. The sleep progress screen includes links for activities, including, but not limited to, evening reflection, a temperature control device (e.g., OOLER), and a sleep tracker (e.g., OURA). FIG. 35 illustrates an example of a week view of a sleep progress screen. FIG. 36 illustrates a daily view of a sleep progress screen.

Figures 37, 38:
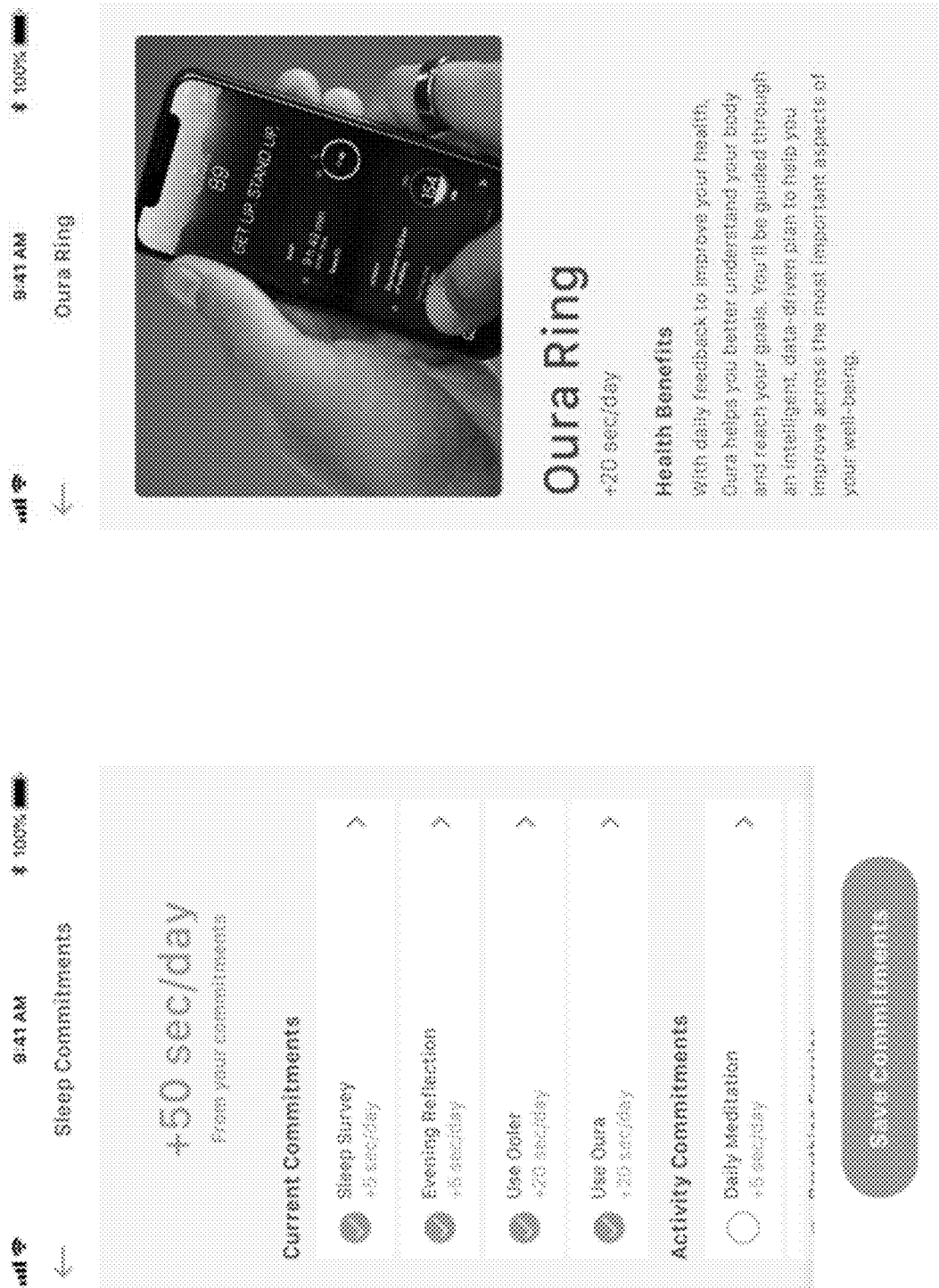
FIG. 37 illustrates an example of a sleep commitment screen where an additional 50 seconds are added per day based on the user's commitments.
FIG. 38 illustrates an example of a sleep commitment screen describing the benefits of using the sleep tracker.

The mobile application preferably allows a user to make commitments to activities. The mobile application preferably provides rewards (e.g., points, badges) and/or other incentives for completing activities over a time period. FIGS. 37-38 illustrate examples of a sleep commitment screen for one embodiment of a GUI for a mobile application. FIG. 37 illustrates an example of a sleep commitment screen where an additional 50 seconds are added per day based on the user's commitments. The user is committed to a sleep survey, evening reflection, using a temperature control device (e.g., OOLER), and using a sleep tracker (e.g., OURA). Additionally, the user can select daily meditation. FIG. 38 illustrates an example of a sleep commitment screen describing the benefits of using the sleep tracker.

Figures 39, 40:
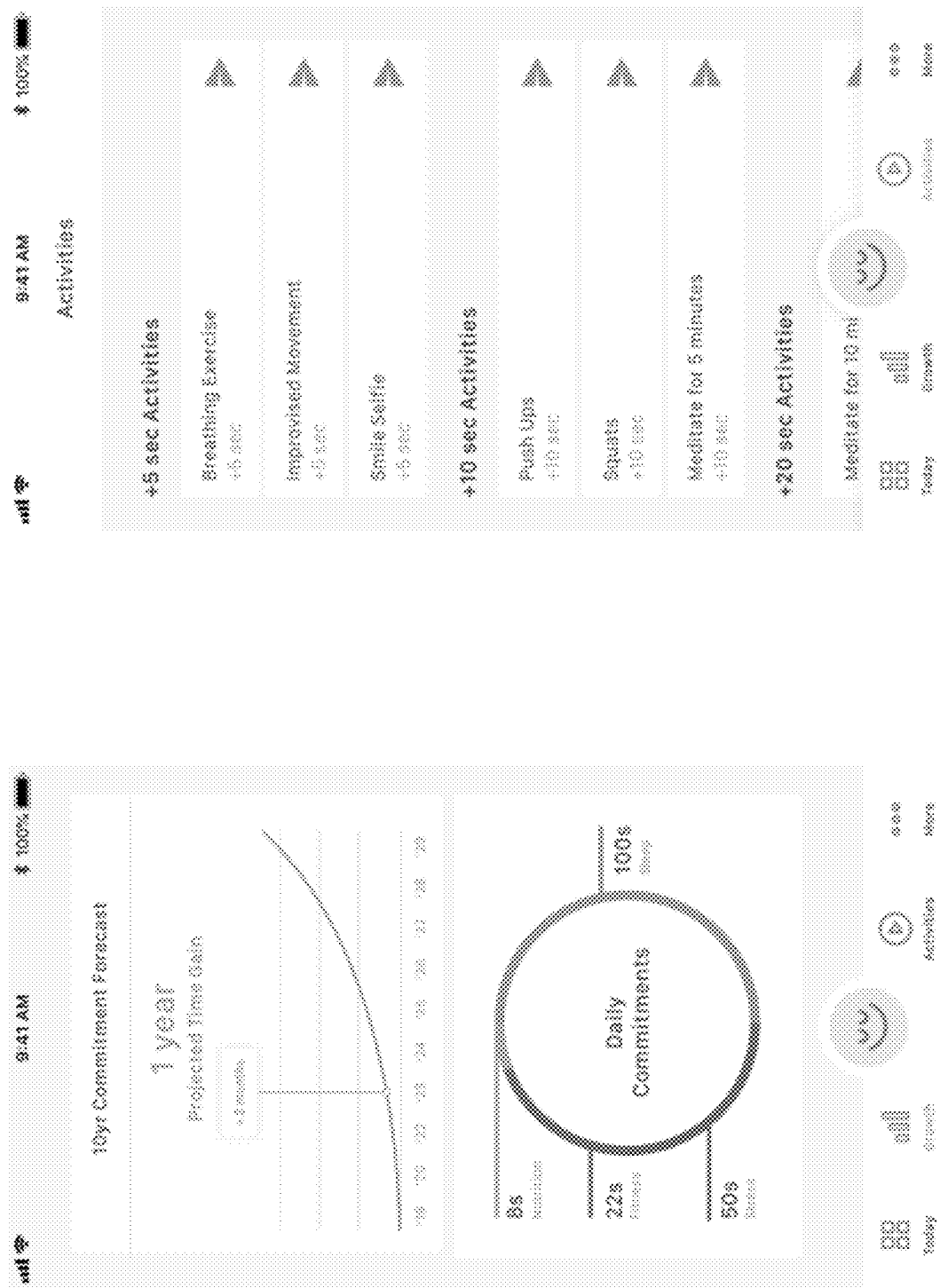
FIG. 39 illustrates an example of a commitment forecast screen for one embodiment of a GUI for a mobile application.
FIG. 40 illustrates an example of an activity screen various activities and scores associated with each activity.

FIG. 39 illustrates an example of a commitment forecast screen for one embodiment of a GUI for a mobile application. In the example shown in FIG. 39, the mobile application projects a 1-year time gain with continual use of the mobile application for a 10-year period. A daily commitment graph illustrates a contribution from nutrition, fitness, stress reduction, and sleep.

Figure 42:
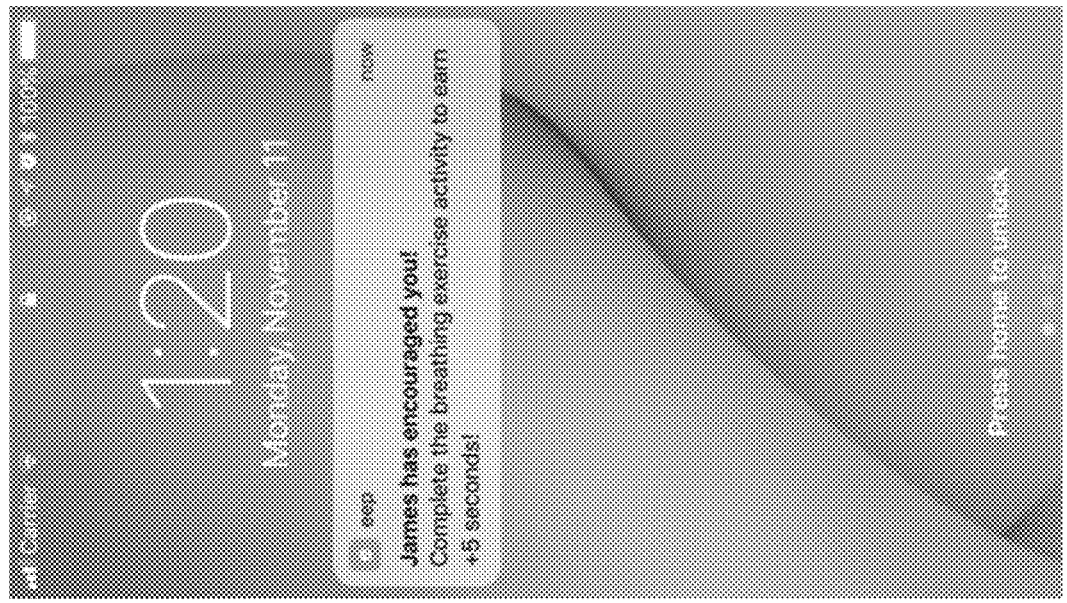
FIG. 42 illustrates an example of an activity challenge notification for one embodiment of a GUI for a mobile application.
Figure 41:
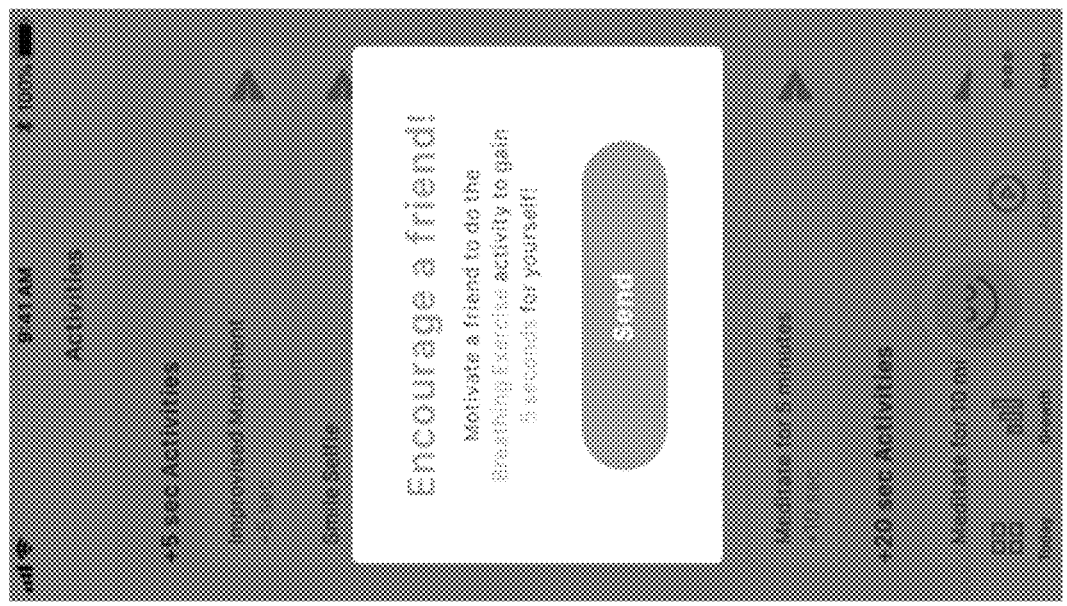
FIG. 41 illustrates an example of sending a challenge to another user to complete an activity.

FIGS. 40-41 illustrate examples of an activity screen for one embodiment of a GUI for a mobile application. FIG. 40 illustrates an example of an activity screen various activities and scores (e.g., in time) associated with each activity. In the example shown in FIG. 40, the activity screen lists 5 second activities (e.g., breathing exercise, improvised movement, smile selfie) and 10 second activities (e.g., push ups, squats, meditation for 5 minutes). The mobile application encourages users to increase minutes of exercise, improve diet, include flexibility training (e.g., yoga) into a regimen of high-intensity interval and/or weight training (e.g., CROSS-FIT), walk and/or bike to work, spend time being active with children, watch less television, try aromatherapy, a new supplement, add more minutes of sunshine each day, and spend more time performing good behaviors instead of bad. FIG. 41 illustrates an example of sending a challenge to another user to complete an activity. FIG. 42 illustrates an example of an activity challenge notification for one embodiment of a GUI for a mobile application.

As previously discussed, the mobile application allows a user to challenge another user to complete an activity and/or share an activity with another user. In one embodiment, the mobile application allows a user to share a game that requires motor movement and/or memory utilization with an elderly grandparent. In one example, the user shares a Simon Says game with a grandparent with Parkinson's disease. Daily improvised movement can help to improve mobility, strength, and quality of life. In another example, the mobile application allows a specialist (e.g., doctor, psychologist) to share an exercise in CBT.

In another embodiment, the mobile application allows a user to share data, research, and/or information with another user (e.g., physician, psychologist, coach, nutritionist, friend). In one example, a fitness or sport coach shares data and information with an athlete. In yet another embodiment, the mobile application allows for users to establish group commitments. In one example, a group of people commit to a race, an event, and/or a change in habit. For example, a group of co-workers decide to quit smoking, run a race, and/or lose weight together. The challenges and/or the shared activities in the mobile application provides for accountability within the mobile application and/or outside of the mobile application (e.g., with family and friends).

Figure 44:
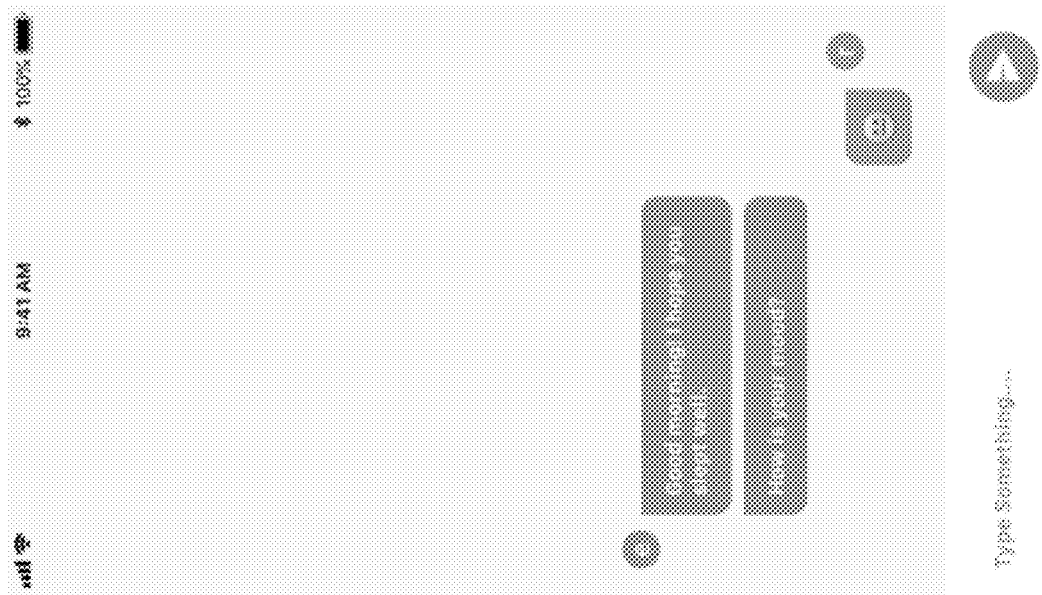
FIG. 44 illustrates an example of a chat where the user's response to the question in FIG. 43 is recorded.
Figure 43:
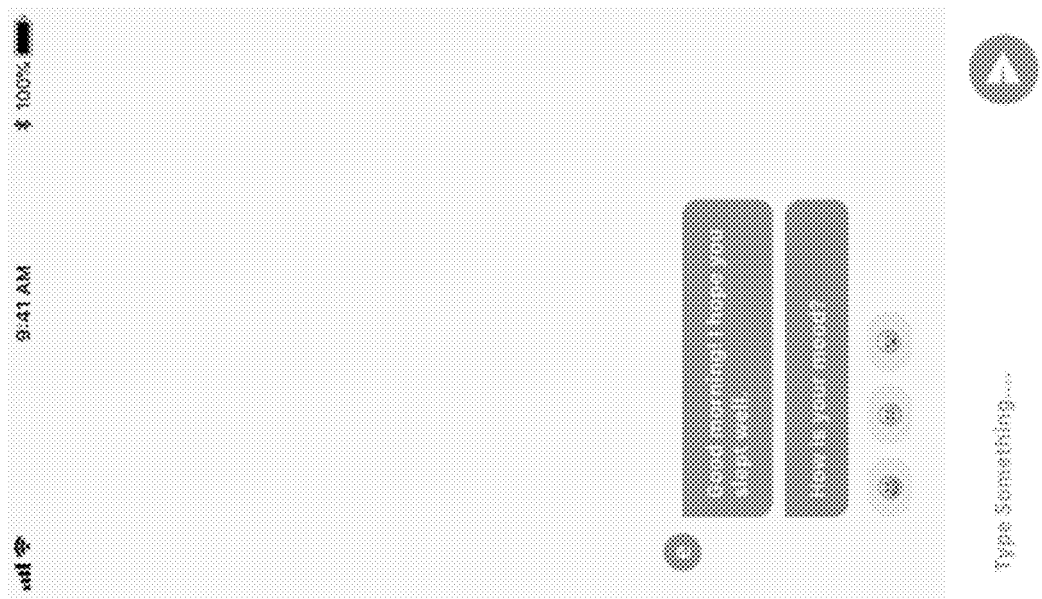
FIG. 43 illustrates an example of a chat where the chatbot asks about the user's mood.
Figure 46:
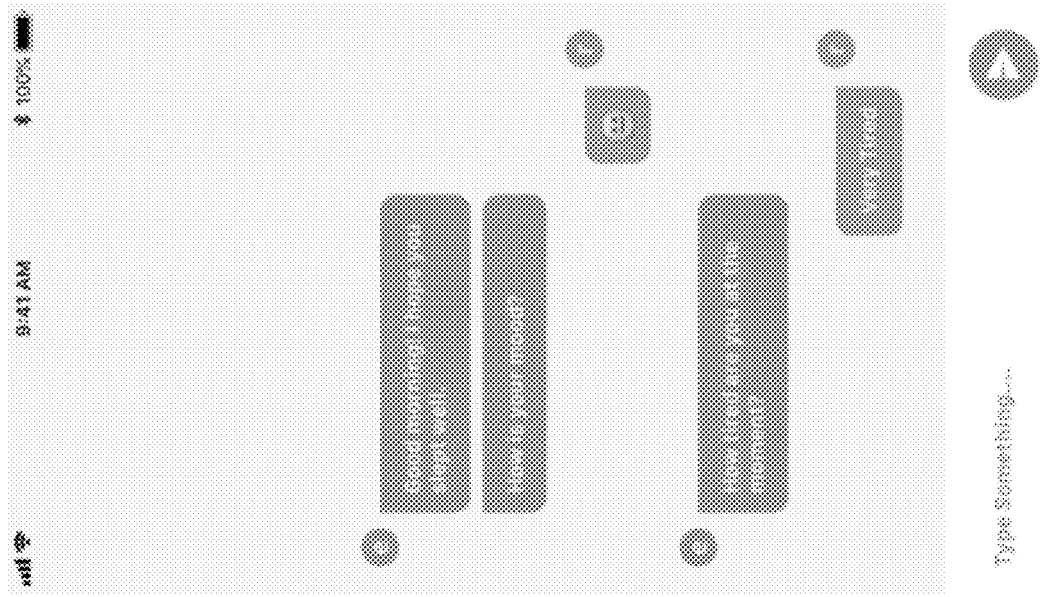
FIG. 46 illustrates an example of a chat where the user's response to the question in FIG. 45 is recorded.
Figure 45:
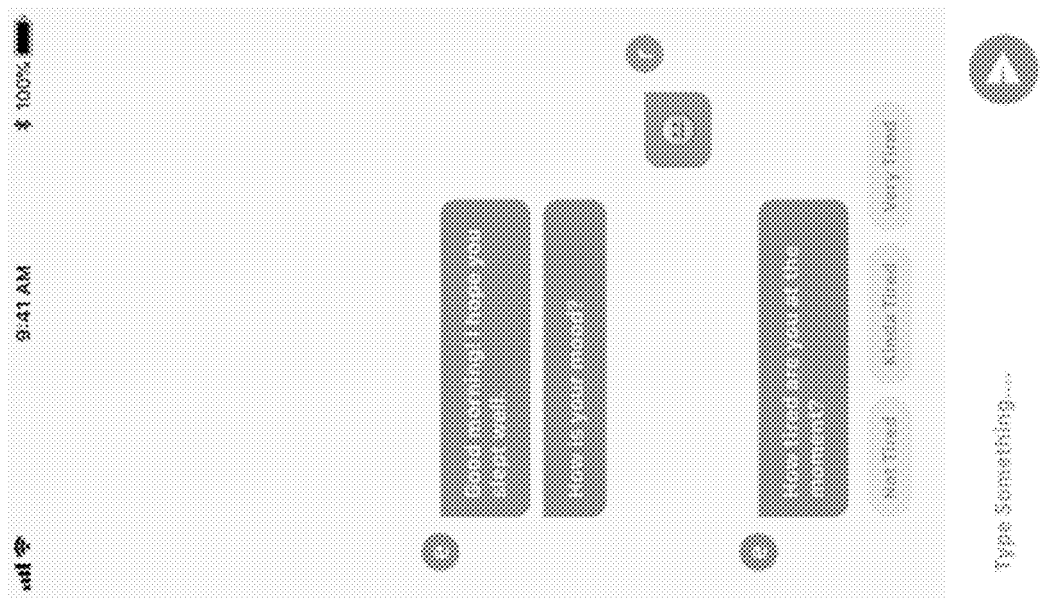
FIG. 45 illustrates an example of a chat where the chatbot asks about how tired the user is at the moment.
Figure 47:
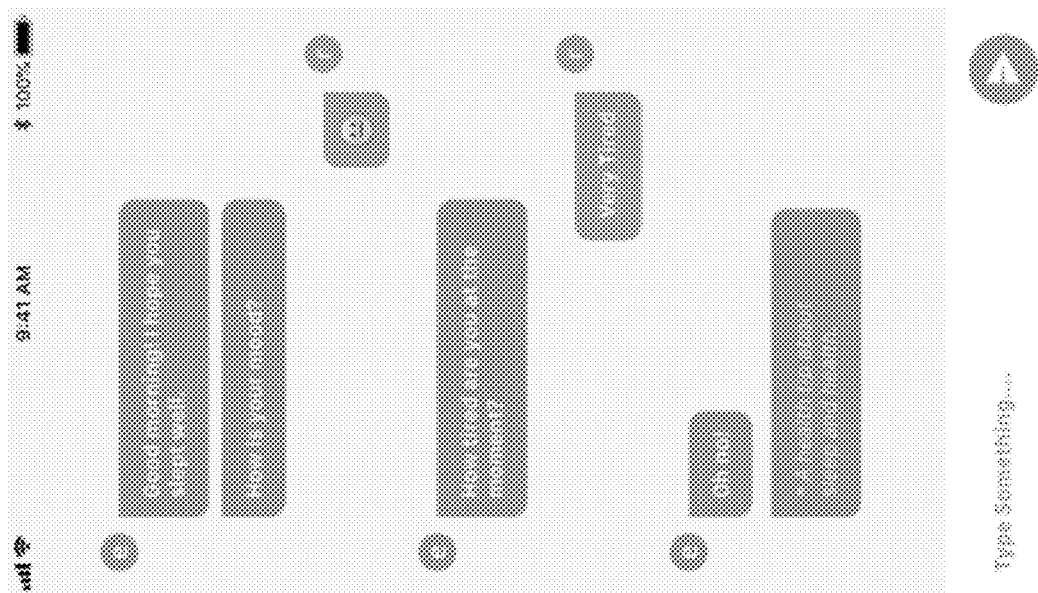
FIG. 47 illustrates an example of a chat where the chatbot includes a health tip about sleep and health.

FIGS. 43-47 illustrate examples of a mood survey chat for one embodiment of a GUI for a mobile application. FIG. 43 illustrates an example of a chat where the chatbot asks about the user's mood. In the example shown in FIG. 43, the chatbot allows the user to select an emoji reflecting the user's mood (e.g., happy, neutral, sad). FIG. 44 illustrates an example of a chat where the user's response to the question in FIG. 43 is recorded. FIG. 45 illustrates an example of a chat where the chatbot asks about how tired the user is at the moment. In the example shown in FIG. 45, the chatbot allows a user to select a response to the question (e.g., not tired, kinda tired, very tired). FIG. 46 illustrates an example of a chat where the user's response to the question in FIG. 45 is recorded. FIG. 47 illustrates an example of a chat where the chatbot includes a health tip about sleep and health.

In one embodiment, the mobile application is operable to determine a user's mood via body sensor data and/or information from third-party applications. For example, if information from a third-party food tracker indicates that a user is eating a significantly higher number of calories for the day, the mobile application asks if the user is stressed. In another example, the mobile application uses data supplied by the EDA sensor to determine changes in emotion (e.g., high skin conductivity indicates a greater amount of sweating due to stress). In yet another example, the mobile application uses data supplied by the heart sensor and movement sensor to determine changes in emotion (e.g., high heart rate with low movement indicates stress). In still another embodiment, the mobile application uses data supplied by the heart sensor to measure stress over time (e.g., decrease in HRV indicates stress, while increase in HRV indicates reduced stress). In one embodiment, the mobile application uses data supplied by the posture sensor determine changes in emotion (e.g., user is slouching, indicating sadness).

The mobile application is preferably operable to display a mood calendar. The mood calendar displays a user's mood over a period of time (e.g., week, month, year). Examples of moods that are tracked using the mobile application include, but are not limited to, joyful, angry, surprised, fearful, sad, disgusted, relaxed, stressed, nervous, upset, depressed, bored, fatigued, relaxed, and happy.

In another embodiment, the mobile application is operable to display a wheel of life. The wheel of life includes, but is not limited to, physical environment, business/career, finances, health, family, friends, romance, personal growth, fun and recreation, emotional health, spiritual health, and/or intellectual challenge. The mobile application allows a user to rate an aspect of the wheel of life (e.g., spiritual health). The mobile application tracks a user's ratings over time. For example, if the rating drops, the mobile application is operable to ask questions to determine the problem and provide suggestions to the user. In one example, the mobile application suggests that a user practice meditation, start a gratitude journal, and/or join a religious study group to improve spiritual health.

Figure 48:
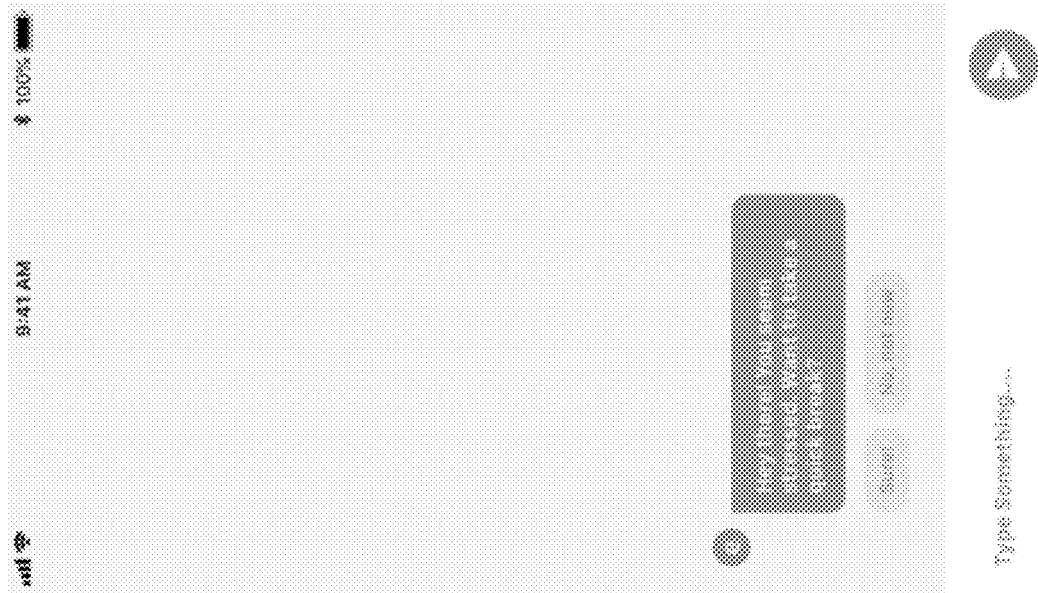
FIG. 48 illustrates an example of a chat where the chatbot observes that the user seems stressed and asks if the user would like to take a break.
Figure 50:
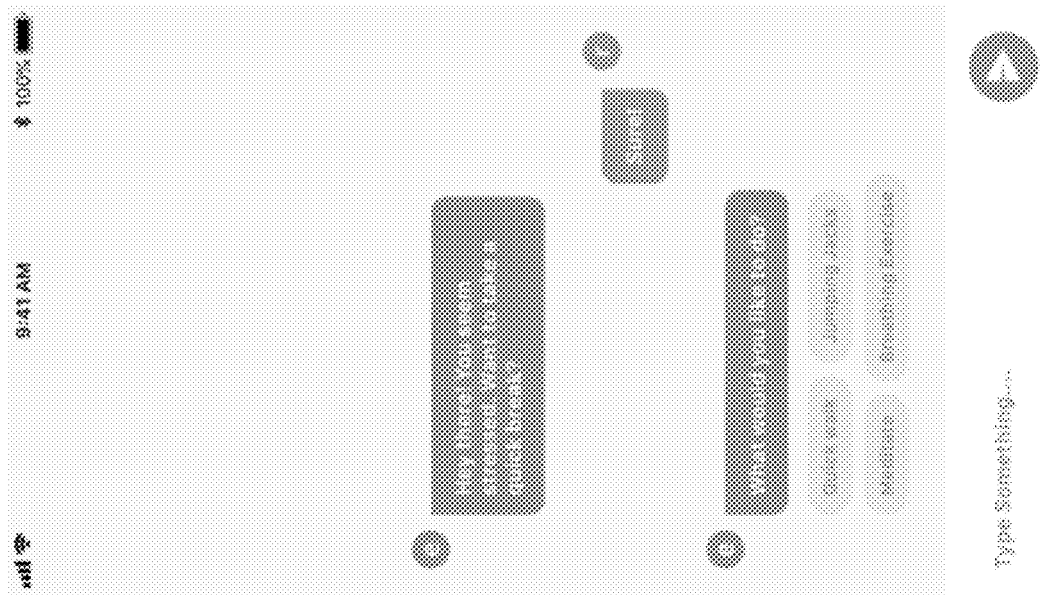
FIG. 50 illustrates an example of a chat where the chatbot asks what activity the user would like to complete.
Figure 49:
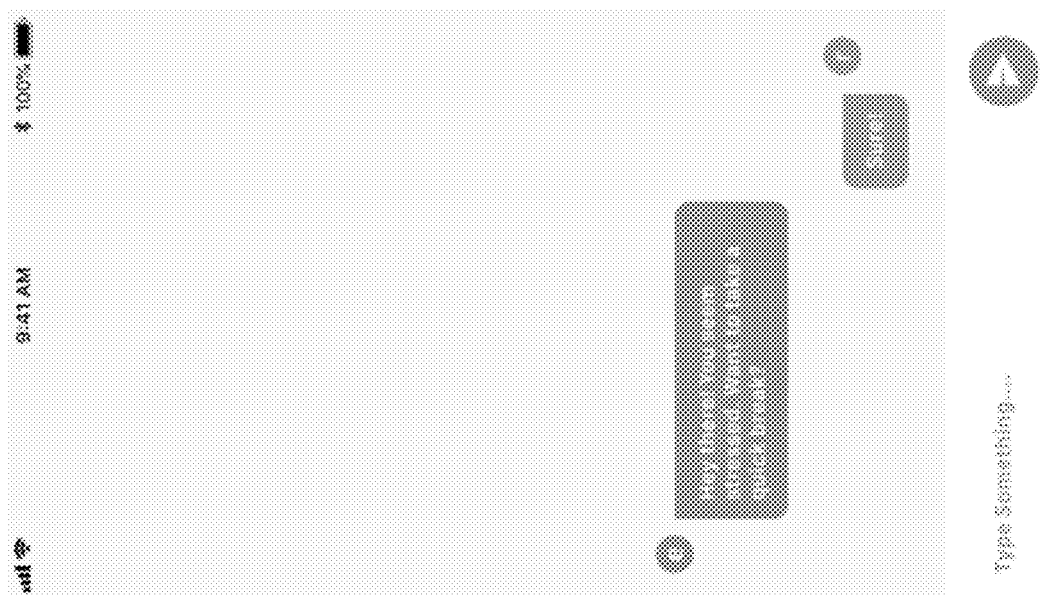
FIG. 49 illustrates an example of a chat where the user's response to the question in FIG. 48 is recorded.
Figure 52:
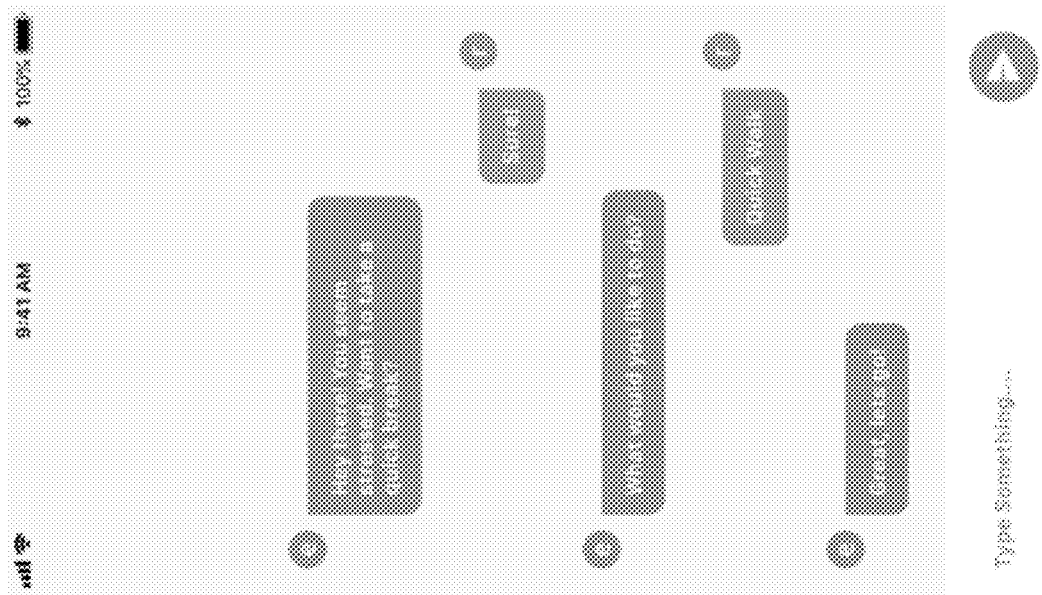
FIG. 52 illustrates an example of a chat where the chatbot encourages the user to participate in the activity.
Figure 51:
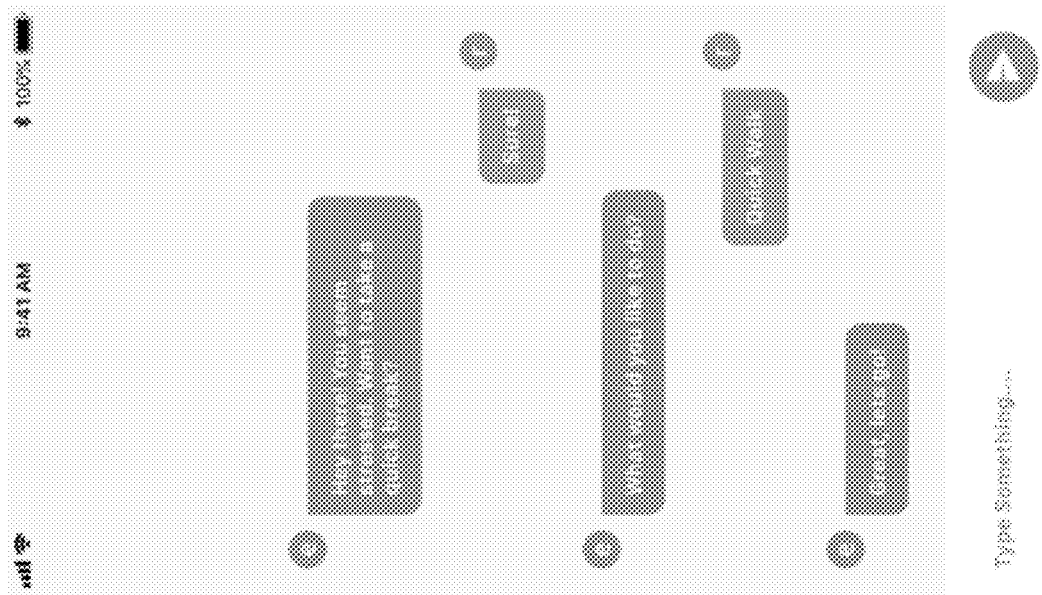
FIG. 51 illustrates an example of a chat where the user's response to the question in FIG. 50 is recorded.

FIGS. 48-52 illustrate examples of a stress break chat for one embodiment of a GUI for a mobile application. FIG. 48 illustrates an example of a chat where the chatbot observes that the user seems stressed and asks if the user would like to take a break. In the example shown in FIG. 48, the chatbot allows the user to select a response to the question (e.g., yes, no). FIG. 49 illustrates an example of a chat where the user's response to the question in FIG. 48 is recorded. FIG. 50 illustrates an example of a chat where the chatbot asks what activity the user would like to complete. In the example shown in FIG. 50, the chatbot allows the user to select a response to the question (e.g., quick walk, meditate, jumping jacks, breathing exercise). FIG. 51 illustrates an example of a chat where the user's response to the question in FIG. 50 is recorded. FIG. 52 illustrates an example of a chat where the chatbot encourages the user to participate in the activity.

Figure 54:
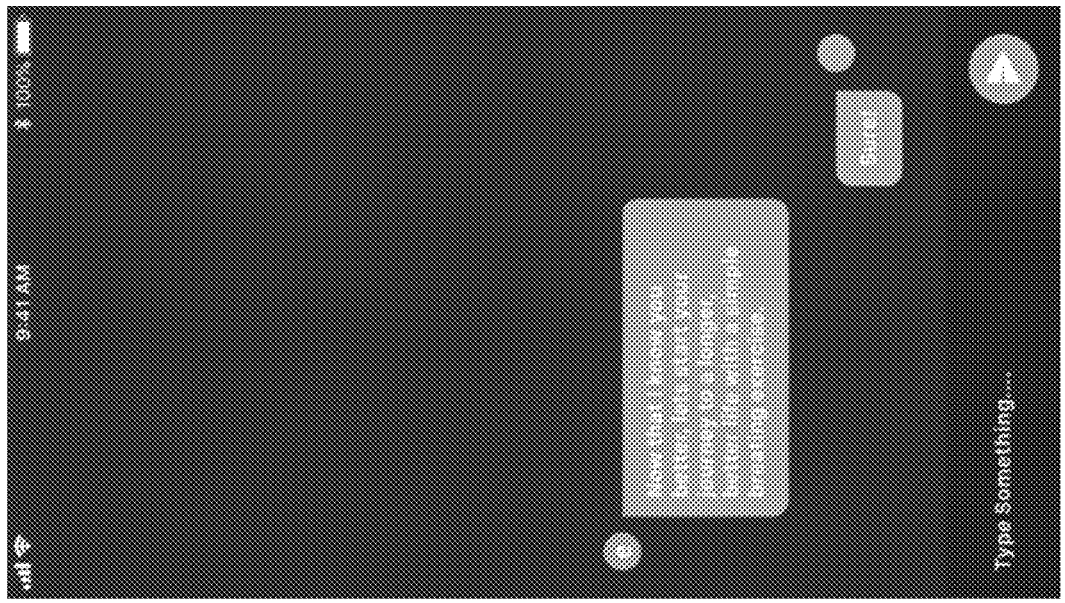
FIG. 54 illustrates an example of a chat where the user's response to the question in FIG. 53 is recorded.
Figure 53:
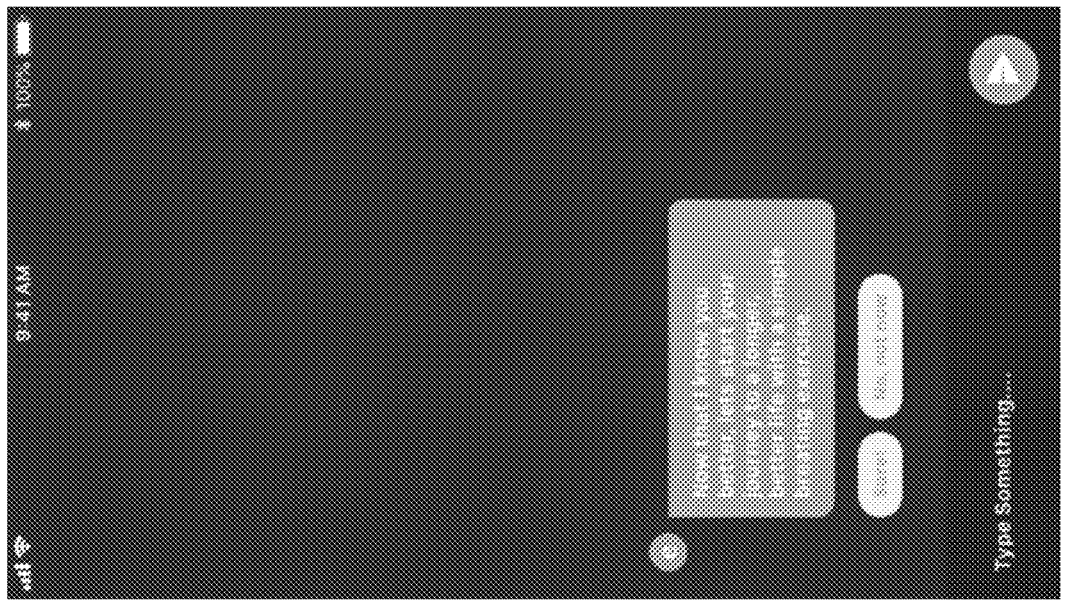
FIG. 53 illustrates an example of a night mode chat where the chatbot asks if the use would like to a breathing exercise.

FIGS. 53-54 illustrate examples of a night mode screen for one embodiment of a GUI for a mobile application. Advantageously, the GUI has a black background, which prevents the user from being exposed to large amounts of blue light. Blue light can suppress melatonin production and make it more difficult to sleep. FIG. 53 illustrates an example of a night mode chat where the chatbot asks if the use would like to a breathing exercise. In the example shown in FIG. 53, the chatbot allows the user to select a response to the question (e.g., yes, no). FIG. 54 illustrates an example of a chat where the user's response to the question in FIG. 53 is recorded.

Figure 56:
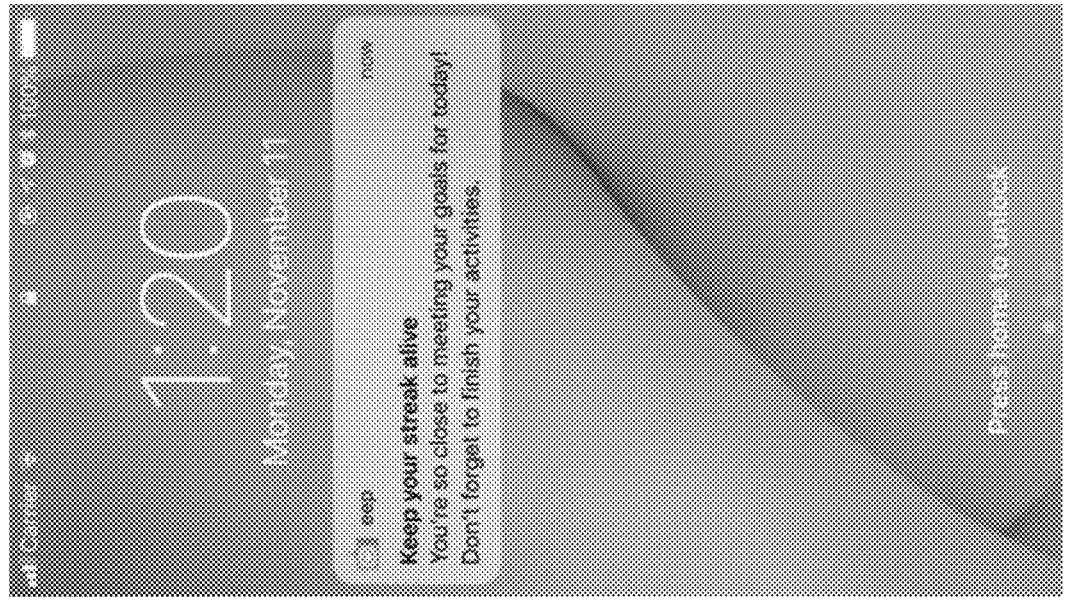
FIG. 56 illustrates an example of the mobile application sending a push notification to remind a user to complete activities to a mobile device.
Figure 55:
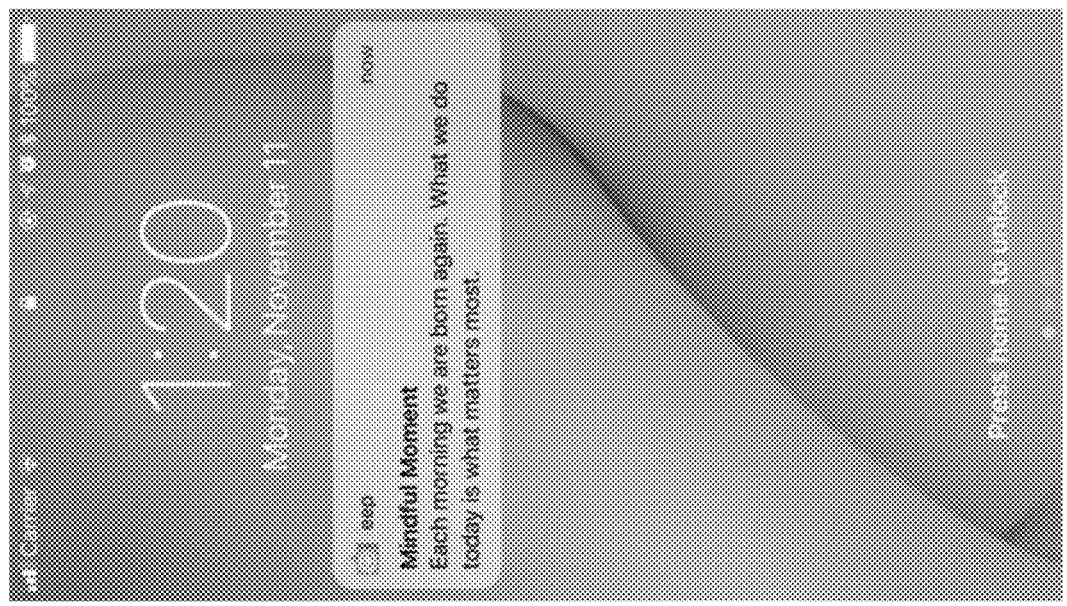
FIG. 55 illustrates an example of the mobile application sending a push notification about mindfulness to a mobile device.
Figure 58:
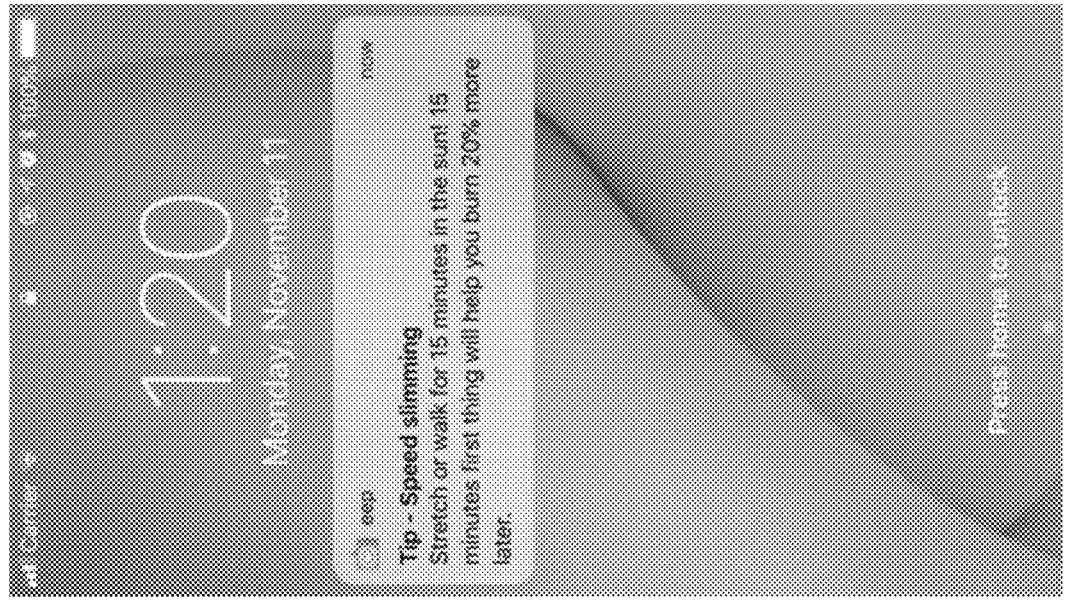
FIG. 58 illustrates an example of the mobile application sending a push notification regarding fitness to a mobile device.
Figure 57:
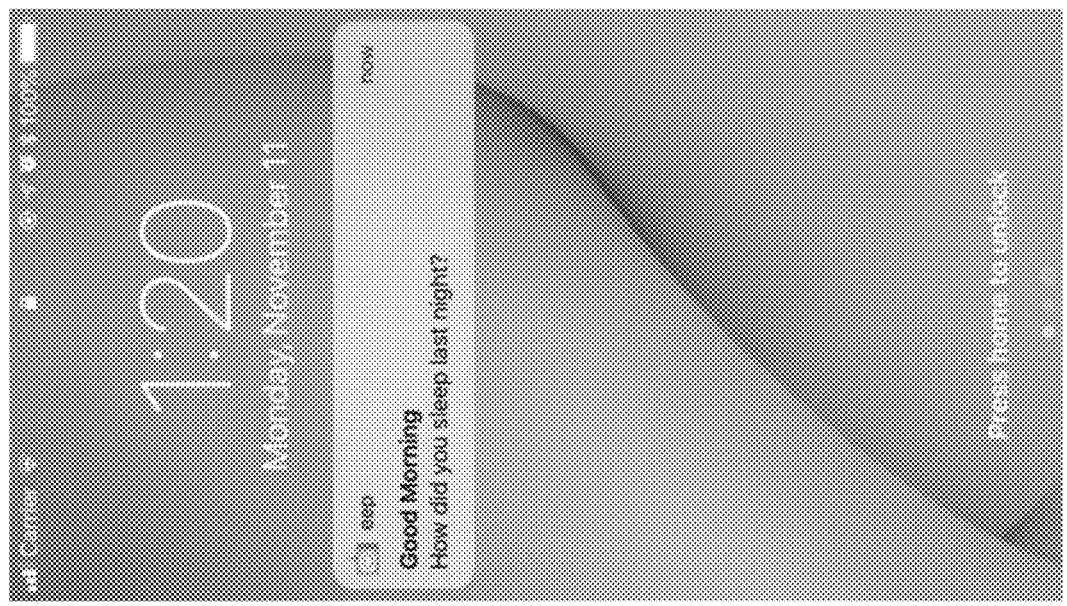
FIG. 57 illustrates an example of the mobile application sending a push notification regarding a sleep survey to a mobile device.
Figure 60:
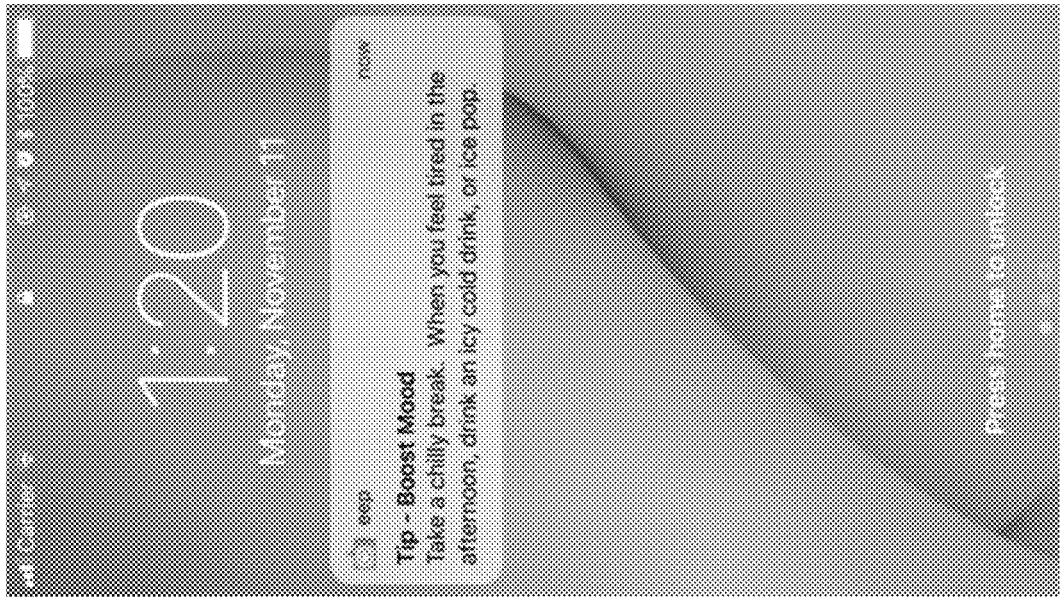
FIG. 60 illustrates an example of the mobile application sending a push notification with a mood boosting tip to a mobile device.
Figure 59:
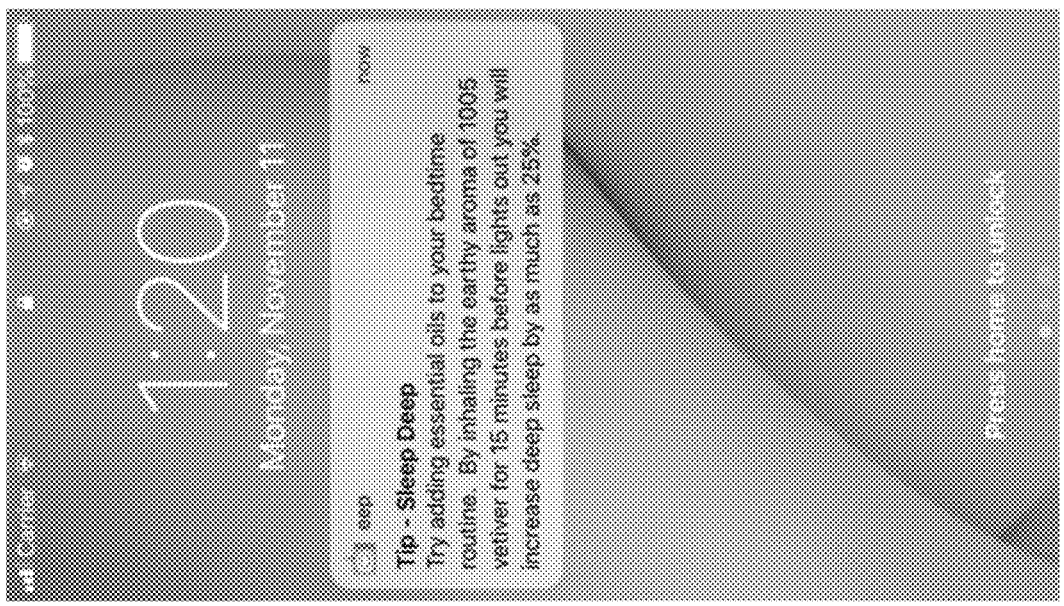
FIG. 59 illustrates an example of the mobile application sending a push notification with a sleep tip to a mobile device.
Figure 62:
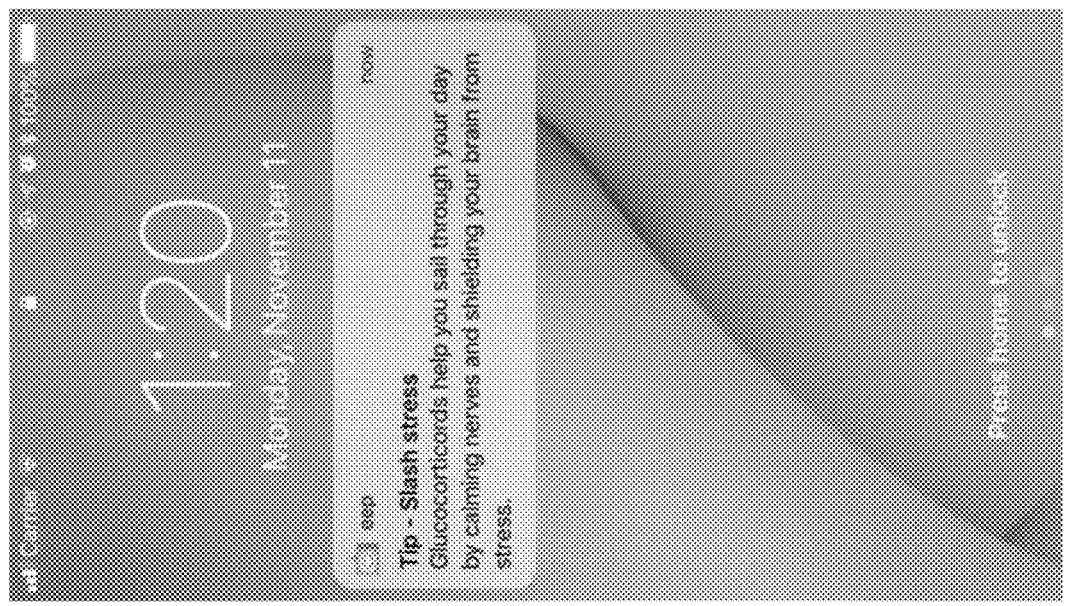
FIG. 62 illustrates an example of the mobile application sending a push notification with a focus improvement tip to a mobile device.
Figure 61:
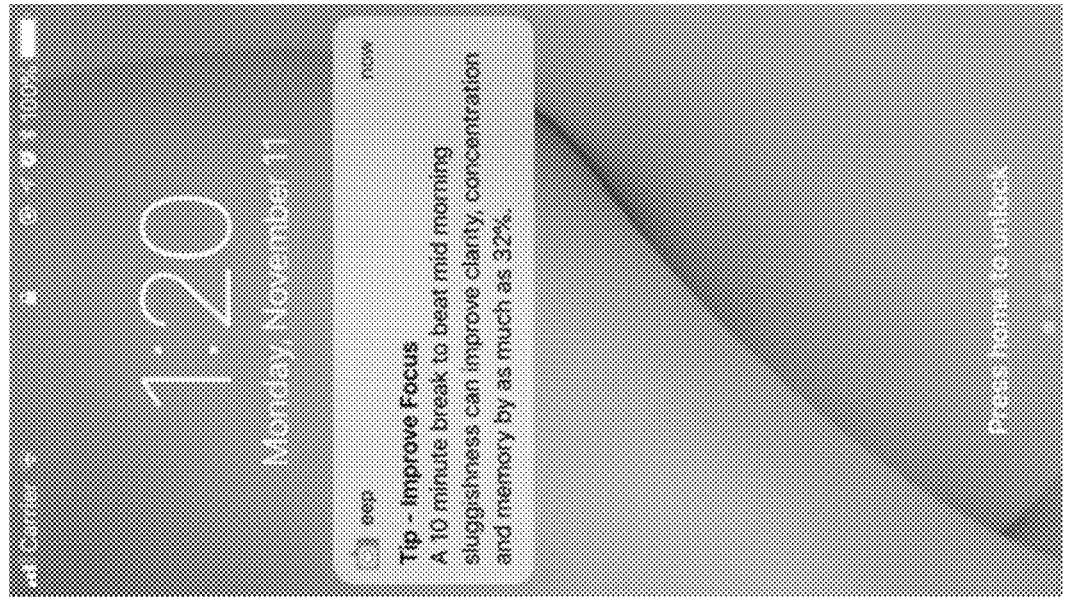
FIG. 61 illustrates an example of the mobile application sending a push notification with a stress relieving tip to a mobile device.

FIGS. 55-62 illustrate examples of push notifications to a mobile device. In FIG. 55, the mobile application sends a push notification about mindfulness to a mobile device. In FIG. 56, the mobile application sends a push notification to remind a user to complete activities to a mobile device. In FIG. 57, the mobile application sends a push notification regarding a sleep survey to a mobile device. In FIG. 58, the mobile application sends a push notification regarding fitness to a mobile device. In FIG. 59, the mobile application sends a push notification with a sleep tip to a mobile device. In FIG. 60, the mobile application sends a push notification with a mood boosting tip to a mobile device. In FIG. 61, the mobile application sends a push notification with a stress relieving tip to a mobile device. In FIG. 62, the mobile application sends a push notification with a focus improvement tip to a mobile device.

Figure 64:
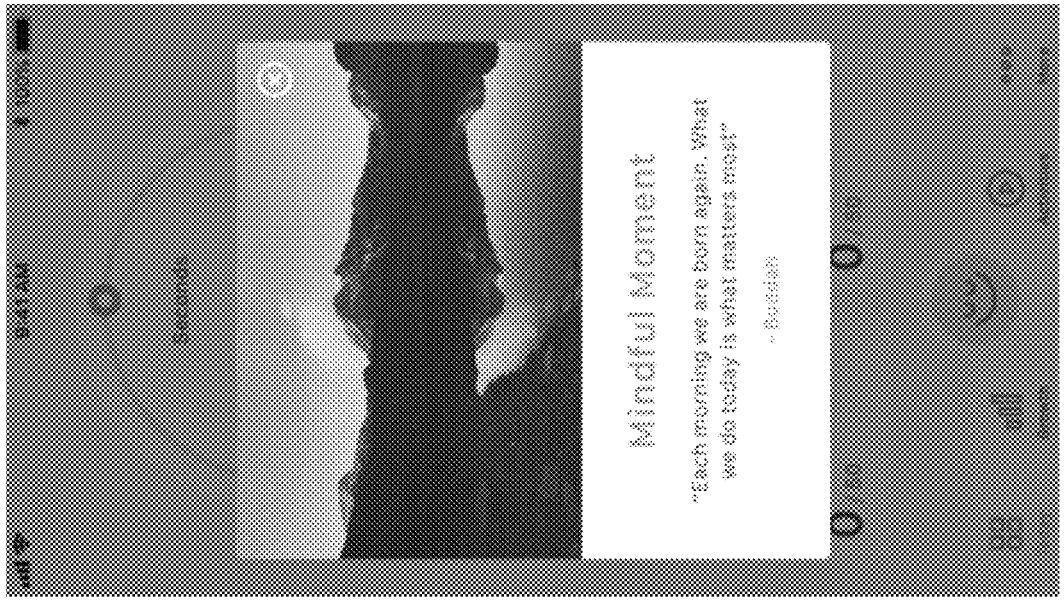
FIG. 64 illustrates a detail screen of the push notification in FIG. 55.
Figure 63:
FIG. 63 illustrates a detail screen of the push notification in FIG. 58.

FIG. 63 illustrates a detail screen of the push notification in FIG. 58. FIG. 64 illustrates a detail screen of the push notification in FIG. 55.

Figure 65:
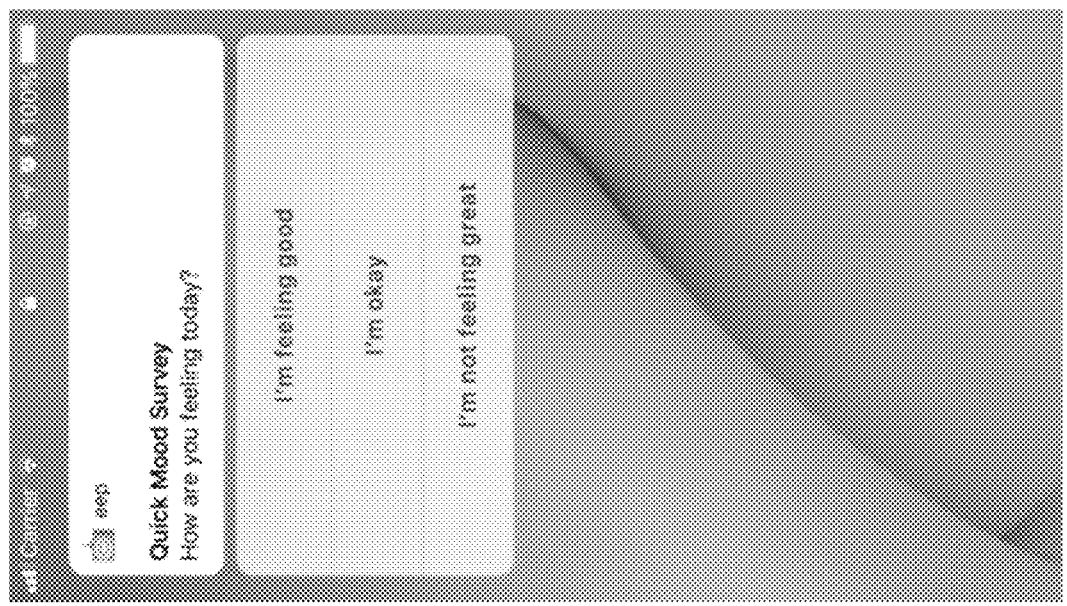
FIG. 65 illustrates an example of an interactive push notification.

FIG. 65 illustrates an example of an interactive push notification. In the example shown in FIG. 65, the mobile application asks the user to complete a mood survey. The push notification provides selectable responses to the question (e.g., good, okay, not good). Advantageously, the interactive push notification allows the mobile application to acquire data about the user directly from the interactive push notification without having to open the mobile application.

In one embodiment, the mobile application is on a smartphone or a tablet. The mobile application is preferably operable to interface with a camera on the smartphone or the tablet. In one embodiment, the mobile application is operable to estimate gender, age, and/or body mass index (BMI) from an image (e.g., a selfie) taken with the camera. In another embodiment, the mobile application is operable to detect chronic disease, alcohol use, and/or evidence of smoking from the image. In yet another embodiment, the mobile application is operable to age progress an image. In still another embodiment, the mobile application is operable to detect an emotion from a facial expression in the image. In one embodiment, the emotion includes, but is not limited to, joy, anger, fear, disgust, contempt, sadness, and/or surprise. The mobile application uses computer vision algorithms to perform facial analysis. In one embodiment, the mobile application uses the International Affective Picture System (TAPS) to determine a user's emotion. Examples of facial analysis software are disclosed in U.S. Pat. Nos. 9,646,046, 9,317,740, 9,311,564, 9,177,230, 9,152,845, 9,147,107, 9,008,416, 8,913,839, 8,818,111, 8,780,221, 8,705,875, and 8,676,740 and U.S. Publication Nos. 20170105568, 20140242560, and 20130158437, each of which is incorporated herein by reference in its entirety.

In another embodiment, the mobile application is operable to recognize an emotion based on a user's voice. Examples of voice analysis software are disclosed in U.S. Pat. Nos. 9,786,299, 8,965,770, 7,940,914, 7,451,079, and 7,340,393 and U.S. Publication Nos. 20180005646 and 20150310878, each of which is incorporated herein by reference in its entirety. In yet another embodiment, the mobile application is operable to classify at least one health state or condition from a voice sample, such as disclosed in U.S. Pat. No. 10,475,530 and U.S. Publication No. 20180254041, each of which is incorporated herein by reference in its entirety.

In still another embodiment, the mobile application is operable to educate a user. In one embodiment, the mobile application is operable to incorporate data from at least one genetic test (e.g., ANCESTRYDNA, 23ANDME). Based on the at least one genetic test, the mobile application is operable to inform a user about health habits (e.g., diet, supplements) that will optimize the user's future health. In one example, the mobile application advises a user that a lack of sleep, too much stress, and the results of the at least one genetic test indicate that the user is predisposed to diabetes and/or autoimmune disorders.

The mobile application is also operable to manage exchanges between a user and their environment. In one example, the mobile application notes that the user's commute time is negatively impacting their stress level. In another example, the mobile application notes that interaction with an individual raises their stress level (e.g., toxic relationship). In yet another example, the mobile application is operable to detect a negative impact of social media use on the user. The mobile application advises a user to minimize time on social media due to the negative impact (e.g., measured through stress responses by the EDA and/or heart sensors). The mobile application preferably identifies these exchanges and coaches the user to minimize stress. The mobile application is also operable to identify positive influences. In one example, the mobile application identifies at least one individual that positively impacts a user's stress level. When the user is stressed out, the mobile application suggests that the user contact the at least one individual for support.

In yet another embodiment, the system is a decentralized platform utilizing blockchain technology. The decentralized platform is operable to store information regarding the user's health, sleep, and stress levels. In one embodiment, the data blocks within the chain are encrypted using cryptography. Individual users can grant access to their data by providing another individual (e.g., healthcare provider) with a private password or key. The blockchain-based decentralized platform provides security for peer-to-peer sharing of medical information by preventing unauthorized access to the user's private medical information.

As previously stated, the user is able to grant access to their data to third parties (e.g., healthcare provider, psychologist, nutritionist, fitness coach, researchers). In one embodiment, the system allows the user to be compensated (e.g., micropayments) for sharing the user's data. In another embodiment, the system provides information to the user regarding clinical trials for medical conditions. In yet another embodiment, the system allows researchers to initially screen users to determine if a user is potentially eligible for a clinical trial. The system also allows insurance companies and/or employers to reward users for positive behaviors (e.g., sleep goals, nutrition goals, fitness goals).

The system preferably determines a chronotype for a user. In one embodiment, the chronotype includes, but is not limited to, morning person, less morning person, neither morning person or night owl, less night owl, and/or night owl. Alternatively, the chronotype includes dolphin, bear, lion, and/or wolf. In one embodiment, the chronotype is determined by a genetic test. In another embodiment, the chronotype is determine by measuring body temperature. For example, a dolphin experiences an increase in core body temperature at night, a morning person/a lion experiences a core body temperature drop around 7:00 pm, a neither morning person or night owl/a bear experiences a core body temperature drop around 9:00 μm, and a night owl/a wolf experiences a core body temperature drop around 10:00 μm. In yet another embodiment, the system determines the chronotype using a self-assessment quiz. FIG. 66 illustrates one embodiment of a quiz to determine chronotype.

In a preferred embodiment, the at least one remote device schedules at least one event or task (e.g., workout, meeting, test, meal, bedtime, wakeup time) based on the chronotype. In one embodiment, the system is operable to interact with at least one calendar on the at least one remote device. In one example, the mobile application suggests a morning person/a lion exercise between 5:00-6:00 pm to increase energy. In another example, the mobile application suggests that a neither morning person nor night owl/a bear refrain from eating after 8:00 pm. In yet another example, the mobile application suggests that a neither morning person nor night owl/a bear not consume caffeine until 9:30-10:00 am.

In a preferred embodiment, the system includes lifestyle assessment questions. In one embodiment, the lifestyle assessment questions include, but are not limited to, a preferred wake up time, a preferred bedtime, alarm clock usage, a time spent in bed prior to falling asleep (e.g., sleep latency), a time spent in bed prior to getting out of bed (e.g., sleep inertia), bed sharing status (i.e., user shares a bed with at least one other individual or pet), exposure to light (e.g., natural light outdoors, blue light, light emitting diodes (LEDs)), a work schedule (e.g., start time, end time, lunch break, days of the week, shift work, commute times), a travel schedule (e.g., time zone changes), financial information (e.g., budget for interventions, budget for joining a gym), and/or household information (e.g., children, ages of children, chronotype of children, spouse or partner, chronotype of spouse or partner). In another embodiment, the lifestyle assessment questions include questions about satisfaction with career, finance, home environment, personal growth, health, family, friends, love (e.g., relationship with significant other), social life, spirituality, emotional health, nutrition, purpose, fun, adventure, creativity, self-esteem, achievements, and/or creativity.

In one embodiment, the system includes questions regarding fatigue. In one embodiment, the questions regarding fatigue are from Krupp, et al. (1989). The Fatigue Severity Scale. Application to patients with multiple sclerosis and systemic lupus erythematosus. Archives of neurology. 46. 1121-3.

In another embodiment, the system determines a nap onset, a nap end, and a nap duration. The nap onset and the nap end are determined by the body sensors and/or from subjective information (e.g., questionnaires). In one embodiment, the system calculates a total duration of sleep in a 24-hour period (i.e., including the nap duration).

In yet another embodiment, the system includes information regarding a difficulty level for an intervention. In one embodiment, the information regarding a difficulty level for the intervention is determined by the user. In another embodiment, the information regarding the difficulty level for the intervention is determined by a coach and/or an influencer. In yet another embodiment, the information regarding the difficulty level for the intervention is determined by a machine learning algorithm. In one embodiment, the machine learning algorithm uses an adoption level of the intervention over all users, an adoption level of the intervention over similar users, a user's tolerance for and/or openness to adopt interventions, a financial cost of the intervention, a time required for the intervention, a user profile, a user medical history (e.g., injury), and/or a user history to determine the difficulty level for the intervention.

In one embodiment, the mobile application includes at least one challenge program. The at least one challenge program incorporates at least one small change into a user's life. The at least one challenge program is preferably for a predetermined period of time (e.g., 21 days, 4 weeks, 30 days, 1 month, 2 months, 3 months, etc.). In one embodiment, the at least one challenge program is related to sleep (e.g., bedtime, wake time, amount of sleep), nutrition (e.g., keto, WHOLE30, eat more vegetables, no candy, no soda, drink 8 glasses of water daily, no alcohol, bring lunch to work), fitness (e.g., daily exercise, push-ups, planks), mental health (e.g., gratitude journal, meditation, connecting with friends and family), and/or habits (e.g., quit smoking, spend time on a hobby, write a novel, reading, decluttering, no television, budget).

In one embodiment, the mobile application suggests additional interventions and/or lifestyle changes when a user is successful with current interventions and/or lifestyle changes. For example, if a user is getting enough sleep, the mobile application suggests that the user start walking or drink more water. In another embodiment, the mobile application suggests alternative interventions and/or lifestyle changes when a user is not successful with current interventions and/or lifestyle changes. For example, if a user is not successful with ice baths, the mobile application suggests cold showers. If the user is not successful with the cold showers, the mobile application suggests turning the temperature on the HVAC at night and/or adding a temperature-regulating mattress pad (e.g., ChiliPad and/or OOLER).

Figure 67:
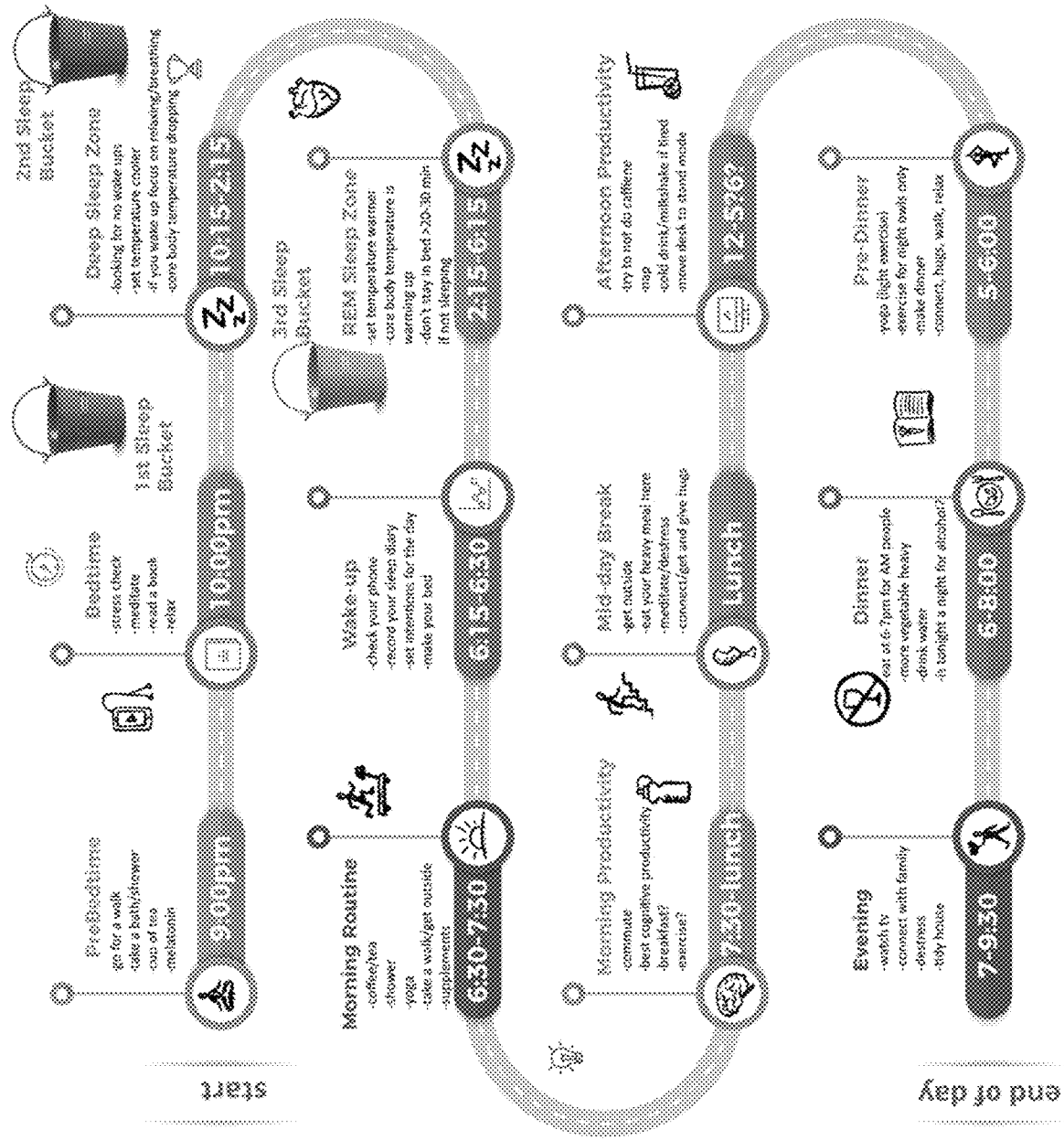
FIG. 67 illustrates an example of a breakdown of a 24-hour period.

FIG. 67 illustrates one example of a breakdown of a 24-hour period. Before bedtime (e.g., 9:00 pm), the mobile application suggests that a user take a walk, take a bath or shower, drink a cup of tea, or take melatonin. At bedtime (e.g., 10:00 pm), the mobile application does a stress check, and encourages a user to meditate, read a book, and/or relax. During the deep sleep zone (e.g., 10:15 pm-2:15 am), the mobile application determines whether there are any wake ups, sets temperature cooler (e.g., room temperature and/or surface temperature of a mattress/mattress pad/blanket), and monitors body temperature to determine that the body temperature is dropping. If the mobile application detects that the user wakes, the mobile application suggests relaxing and/or breathing exercises. During the REM sleep zone (e.g., 2:15-6:16 am), the mobile application sets the temperature warmer (e.g., room temperature and/or mattress/mattress pad temperature) and monitors the body temperature to determine that the body temperature is warming. If the mobile application detects that the user wakes, the mobile application suggests that the user not remain in bed more than 20-30 minutes after waking if the user cannot fall back asleep. At wake-up (e.g., 6:15-6:30 am), the mobile application prompts the user to record a sleep diary and set intentions for the day. In a preferred embodiment, the mobile application records and stores the sleep diary (e.g., in the historical subjective database and/or the global historical subjective database) and the intentions (e.g., in local storage). In one embodiment, the system records and stores the sleep diary, the intentions, and/or a journal (e.g., gratitude journal) on the cloud.

The mobile application is preferably operable to record caffeine consumption (e.g., coffee, tea, energy drinks), exercise information (e.g., type of exercise, duration, intensity, calories burned), and/or supplements (e.g., vitamins, minerals, herbs) taken, for example, during the morning routine. The morning productivity period is a time of best cognitive productivity. In a preferred embodiment, the mobile application records nutrition information (e.g., breakfast), including, but not limited to, number of calories, grams of fat, grams of carbohydrates, grams of protein, vitamins, minerals, and/or ingredients. During the mid-day break (e.g., lunch), the mobile application suggests that the user go outside, eat the heaviest meal of the day, meditate and/or destress, and/or connect with other individuals (e.g., communication, physical touch). The mobile application provides a prompt to not drink caffeine after a time point (e.g., noon). During a pre-dinner time, the mobile application suggests light exercise (e.g., yoga) for non-night owls, and suggests relaxing and connecting with other individuals.

Figure 68:
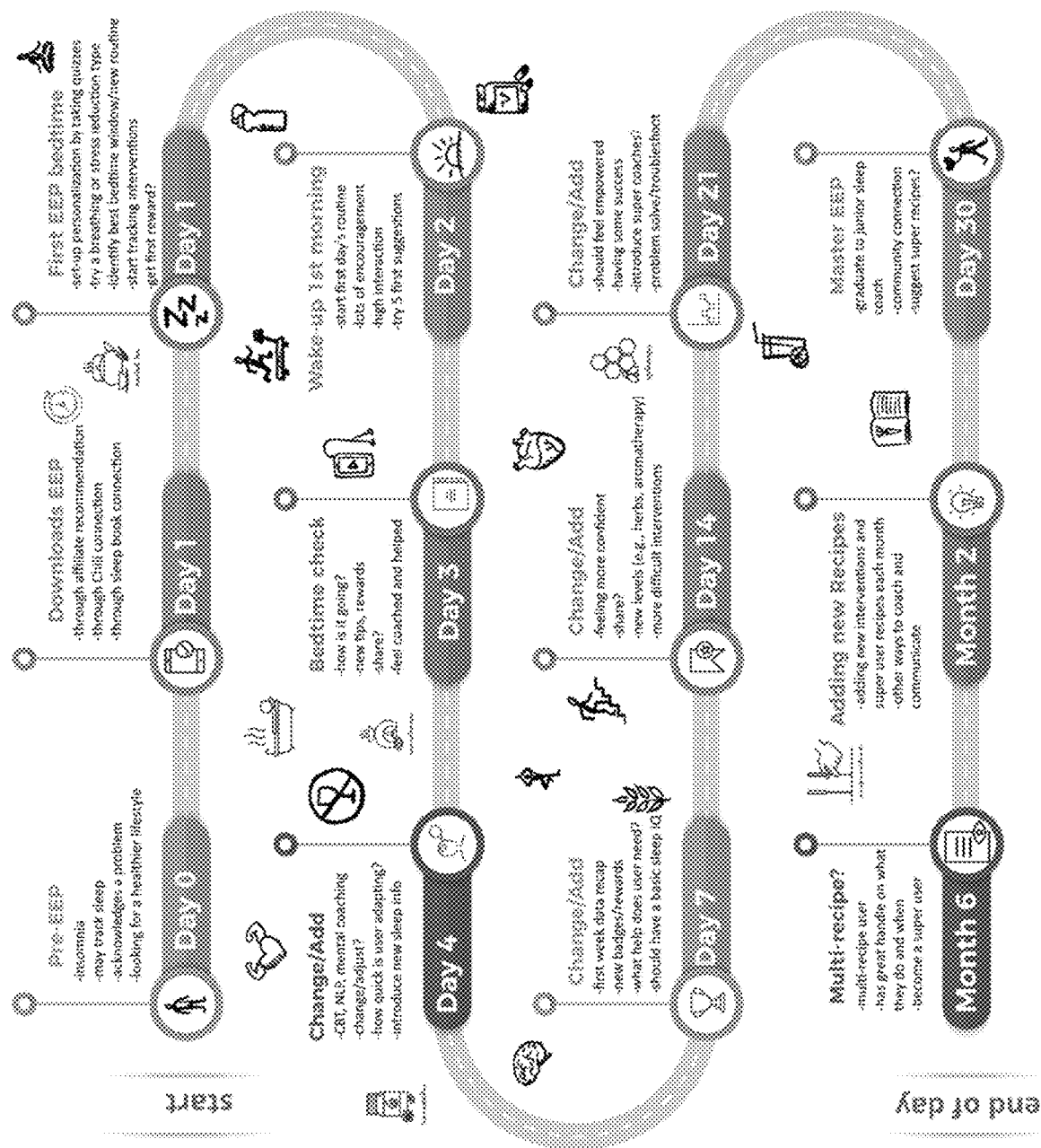
FIG. 68 illustrates one example of a breakdown of a 6-month period.

FIG. 68 illustrates one example of a breakdown of a 6-month period. Before using the mobile application, the user may have insomnia and/or want to be healthier. On the first day of use, the mobile application provides quizzes to personalize suggestions for the user, including determining a chronotype. The mobile application begins tracking interventions on the first day of use. One the second day, the mobile application requests feedback from the user, provides a routine (e.g., based on chronotype), and interacts with the user. The mobile application is preferably operable to provide at least one reward (e.g., badge, status level, icon) to a user. The mobile application evaluates interventions to determine if the interventions are successful or not successful. If one or more interventions are not successful, the mobile application is operable to suggest at least one alternative intervention. In a preferred embodiment, the mobile application initially suggests interventions that are easy (e.g., go to bed at a specific time). The mobile application then suggests more difficult interventions as time passes. Alternatively, the mobile application initially suggests interventions projected to have the greatest impact, followed by interventions projected to have less impact. For example, the mobile application suggests a change in bedtime and wake time based on the chronotype.

In one embodiment, the mobile application is operable to prioritize user goals. For example, a user wants to exercise more and sleep better. The mobile application prioritizes solving the user's sleep problems in the first week, which will allow the user to have more energy to exercise in the second week.

FIG. 69 shows a table with an example of connections for users. In the example shown in FIG. 69, users are connected to a chronotype, a diet, at least one fitness type, at least one intervention, at least one influencer, and/or at least one coach. In one embodiment, the chronotype includes, but is not limited to, morning person, less morning person, neither morning person or night owl, less night owl, and/or night owl. Alternatively, the chronotype includes dolphin, bear, lion, and/or wolf. Diet includes any way of eating, including, but not limited to, ketogenic (keto) diet, paleo diet, fasting (e.g., intermittent fasting), WHOLE30, caloric restriction, vegan diet, vegetarian diet, Mediterranean diet, and gluten-free diet. Fitness includes any form of exercise (e.g., aerobic, strength, flexibility, balance), including, but not limited to, yoga, swimming, weights, running, cycling, kickboxing, CROSSFIT, ORANGE THEORY, barre, Pilates, walking, high intensity interval training (HIIT), and bodyweight exercises (e.g., push-ups, burpees, planks, squats, lunges). Interventions include any intervention that reduces stress or promotes sleep, including, but not limited to, meditation, journaling, breathing exercises, tiny habits, and medication or supplements (e.g., antihistamines, benzodiazepines, antidepressants, melatonin, chamomile, ashwagandha, valerian root, omega-3 fatty acids, B-vitamins, L-theanine). Influencers are individuals with the ability to influence other users to adopt fitness, diet, and/or intervention regimens. Coaches are individuals with the ability to suggest users adopt particular fitness, diet, and/or intervention regimens based on personalized goals and/or needs.

In another embodiment, the connections also include, but are not limited to, health condition (e.g., injury), predisposition to health condition (e.g., family history of diabetes, history of gestational diabetes), age, relationship status (e.g., married, living with a partner, divorced, widowed, single), location, parental status, gender, medication, supplement, and/or a degree of willingness to accept alternative medicine.

Figure 70:
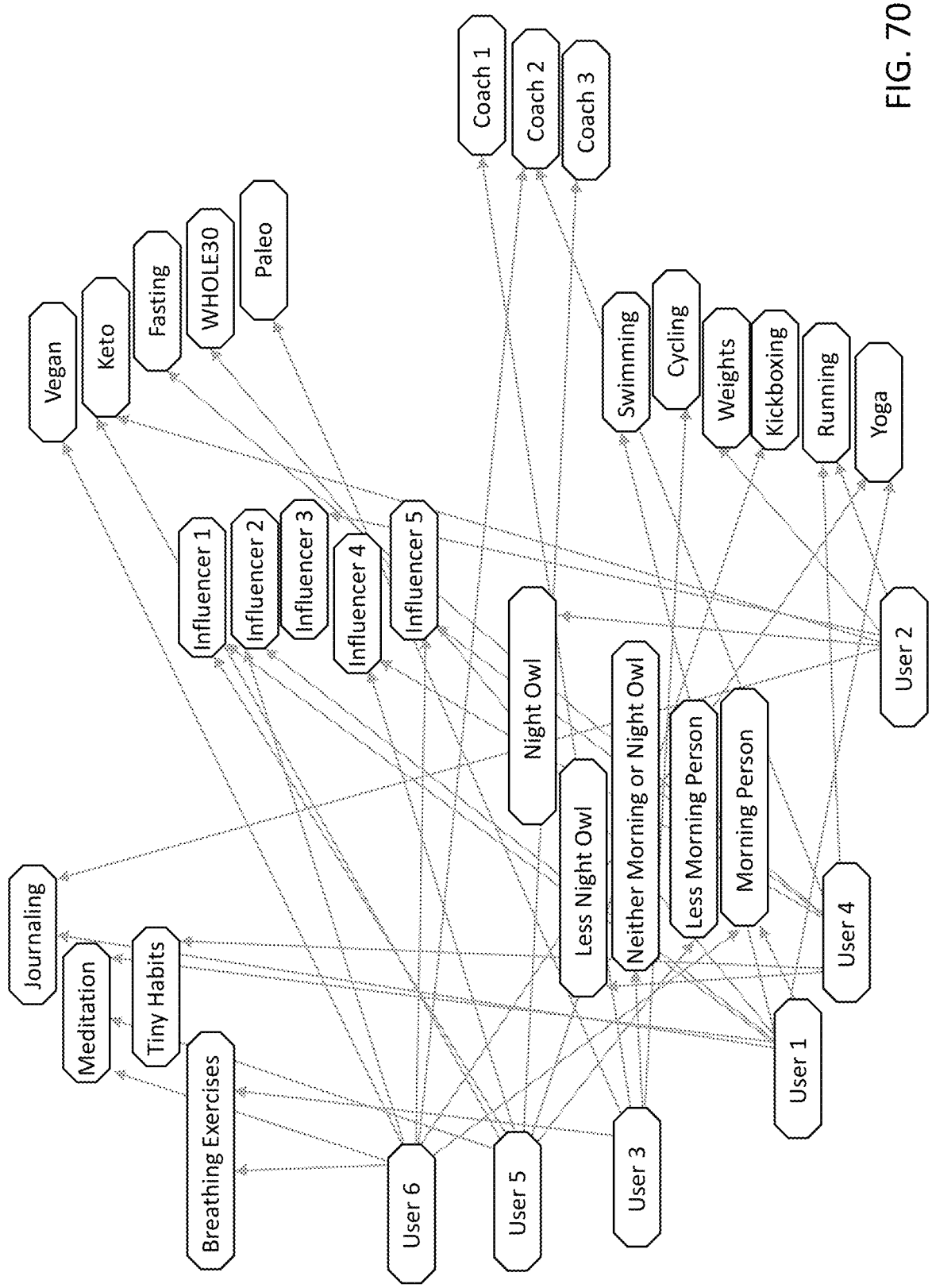
FIG. 70 shows a map of the connections from the table in FIG. 69.

FIG. 70 shows a map of the connections from the table in FIG. 69.

In one embodiment, the system allows a user to follow at least one influencer, at least one coach, and/or at least one other user. In another embodiment, the system provides a social networking component. The social networking component allows users to post updates and/or photos for other users to view, provide reactions (e.g., like, sad, etc.), and/or comment. In yet another embodiment, the social networking component is accessible via a third-party application.

In another embodiment, the mobile application updates the machine learning models based on recommendations from influencers. In one embodiment, the mobile application is operable to weigh recommendations based on ratings from the user. For example, if a user follows or is connected to two influencers and rates a first influencer as an 8/10 and a second influencer as a 6/10, the mobile application is operable to weigh recommendations from the first influencer higher than recommendations from the second influencer.

In one embodiment, the system uses global data (e.g., global historical subjective data, global historical objective data, global historical environmental data, global profile data) to initially train the machine learning algorithms. The machine learning algorithms preferably suggest at least one intervention to the user to reduce stress, increase health, and/or promote sleep. In another embodiment, the machine learning algorithms are further refined and/or personalized by sensor data (e.g., body sensors, environmental sensors), user data (e.g., user profile, historical subjective data, historical objective data, historical environmental data), and/or feedback (e.g., user feedback, healthcare professional feedback, expert feedback, etc.). In yet another embodiment, the mobile application uses if-then rules to provide interventions and/or suggestions. For example, if a heart rate sensor determines that a user's heart rate is high without accompanying movement detected on an accelerometer, the mobile application provides a suggestion to meditate or take a walk.

The system is preferably operable to detect pivots or changes in a user's lifestyle. For example, the system offers different interventions to a pregnant woman or a breastfeeding mother (e.g., supplements, less rigorous exercise) than to a fit woman. In one embodiment, the system detects whether a user has moved and/or is travelling. In another embodiment, the system uses GPS to determine whether the user has moved and/or is travelling.

The system is preferably operable to integrate with at least one calendar for the user. In one embodiment, the system provides notifications to a user and/or a checklist for a user. For example, the system provides a notification for the user to lay out supplements on Sunday.

In one embodiment, the camera on the at least one remote device is operable to scan a room and/or a sleeping environment. The system is operable to user the scan of the room and/or the sleeping environment to provide feedback to a user and/or suggest at least one intervention or at least one change to the room and/or the sleeping environment (e.g., darker blinds, declutter) to reduce stress and/or promote sleep. In one embodiment, the system uses augmented reality to display the at least one intervention or the at least one change to the room and/or the sleeping environment on the at least one remote device. Advantageously, this allows a user to see how the at least one intervention or the at least one change to the room and/or the sleeping environment would affect the room and/or sleeping environment.

Figure 71:
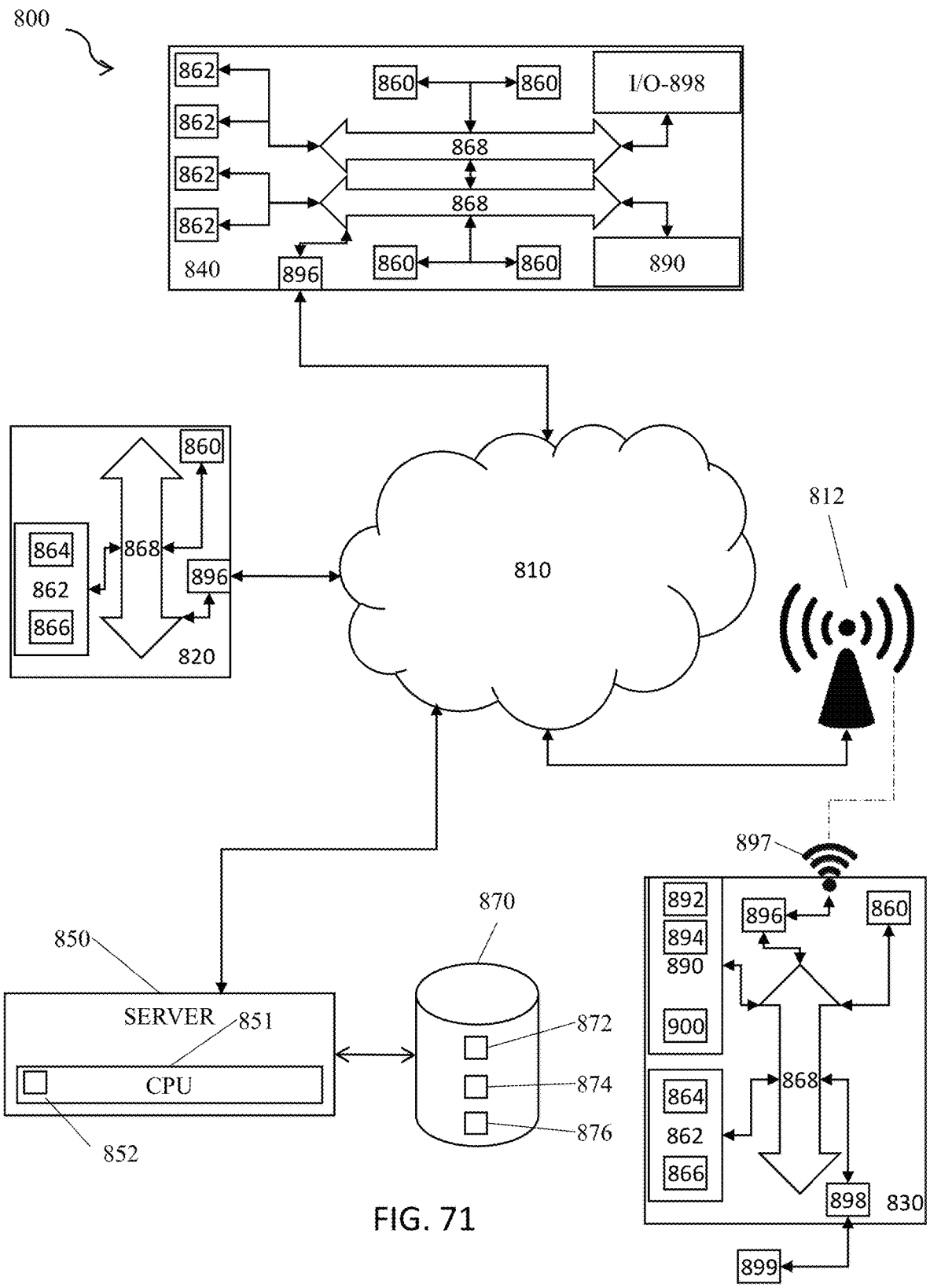
FIG. 71 shows a schematic diagram illustrating general components of a cloud-based computer system.

FIG. 71 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 may house an operating system 872, memory 874, and programs 876.

In one embodiment of the invention, the system 800 includes a cloud-based network 810 for distributed communication via a wireless communication antenna 812 and processing by at least one mobile communication computing device 830. In another embodiment of the invention, the system 800 is a virtualized computing system capable of executing any or all aspects of software and/or application components presented herein on the computing devices 820, 830, 840. In certain aspects, the computer system 800 may be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital computers 820, 840, 850 and mobile devices 830, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in this document In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 may additionally include components such as a storage device 890 for storing the operating system 892 and one or more application programs 894, a network interface unit 896, and/or an input/output controller 898. Each of the components may be coupled to each other through at least one bus 868. The input/output controller 898 may receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 71, multiple processors 860 and/or multiple buses 868 may be used, as appropriate, along with multiple memories 862 of multiple types (e.g., a combination of a DSP and a microprocessor, a plurality of microprocessors, one or more microprocessors in conjunction with a DSP core).

Also, multiple computing devices may be connected, with each device providing portions of the necessary operations (e.g., a server bank, a group of blade servers, or a multi-processor system). Alternatively, some steps or methods may be performed by circuitry that is specific to a given function.

According to various embodiments, the computer system 800 may operate in a networked environment using logical connections to local and/or remote computing devices 820, 830, 840, 850 through a network 810. A computing device 830 may connect to a network 810 through a network interface unit 896 connected to a bus 868. Computing devices may communicate communication media through wired networks, direct-wired connections or wirelessly, such as acoustic, RF, or infrared, through an antenna 897 in communication with the network antenna 812 and the network interface unit 896, which may include digital signal processing circuitry when necessary. The network interface unit 896 may provide for communications under various modes or protocols.

In one or more exemplary aspects, the instructions may be implemented in hardware, software, firmware, or any combinations thereof. A computer readable medium may provide volatile or non-volatile storage for one or more sets of instructions, such as operating systems, data structures, program modules, applications, or other data embodying any one or more of the methodologies or functions described herein. The computer readable medium may include the memory 862, the processor 860, and/or the storage media 890 and may be a single medium or multiple media (e.g., a centralized or distributed computer system) that store the one or more sets of instructions 900. Non-transitory computer readable media includes all computer readable media, with the sole exception being a transitory, propagating signal per se. The instructions 900 may further be transmitted or received over the network 810 via the network interface unit 896 as communication media, which may include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

It is also contemplated that the computer system 800 may not include all of the components shown in FIG. 71, may include other components that are not explicitly shown in FIG. 71, or may utilize an architecture completely different than that shown in FIG. 71. The various illustrative logical blocks, modules, elements, circuits, and algorithms described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

The above-mentioned examples are provided to serve the purpose of clarifying the aspects of the invention, and it will be apparent to one skilled in the art that they do not serve to limit the scope of the invention. The above-mentioned examples are just some of the many configurations that the mentioned components can take on. All modifications and improvements have been deleted herein for the sake of conciseness and readability but are properly within the scope of the present invention.

The invention claimed is:

1. A system to reduce stress and promote sleep comprising:
   at least one remote device;
   at least one remote server; and
   at least one body sensor;
   wherein the at least one remote device is in network communication with the at least one remote server and the at least one body sensor;
   wherein the at least one remote server collects body sensor data from the at least one body sensor;
   wherein the at least one remote server is operable to estimate sleep stages from the body sensor data;
   wherein the at least one remote server is operable to run at least one algorithm to suggest at least one intervention to a user to reduce stress and/or promote sleep based on a user profile, the body sensor data, and/or user provided information, and
   wherein the at least one remote server is operable to adjust parameters of the system based on a comparison of predicted values generated by a virtual model and optimized values generated by a simulation engine.

2. The system of claim 1, wherein the at least one body sensor includes a heart rate sensor, a respiration sensor, an electrooculography sensor, a body weight sensor, a movement sensor, an electromyography sensor, a brain wave sensor, a body temperature sensor, an analyte sensor, a pulse oximeter sensor, a blood pressure sensor, an electrodermal activity sensor, and/or a body fat sensor.

3. The system of claim 1, further comprising at least one environmental sensor, wherein the at least one environmental sensor includes a temperature sensor, a humidity sensor, a noise sensor, an air quality sensor, a light sensor, a motion sensor, a barometric sensor, and/or a camera.

4. The system of claim 1, further comprising a mattress with adjustable firmness and/or elevation; a mattress pad, a blanket, and/or a mattress with adjustable surface temperature; an alarm clock; a humidifier; a dehumidifier; a pulsed electromagnetic field device; a transcutaneous electrical nerve stimulation device; a sound generator; an air purifier; a scent generator; red and/or infrared lighting; a lighting system; a fan; a sunrise simulator; and/or a sunset simulator.

5. The system of claim 1, further comprising a home automation system, wherein the at least one remote device is operable to transmit commands to the home automation system to adjust environmental conditions.

6. The system of claim 1, wherein the at least one remote device is operable to recognize an emotion and/or classify at least one health state or condition based on a voice sample from a user.

7. The system of claim 1, wherein a camera on the at least one remote device is operable to scan a room and/or a sleeping environment, and wherein the at least one remote device is operable to provide feedback to a user and/or suggest at least one intervention or at least one change to the room and/or the sleeping environment to reduce stress and/or promote sleep.

8. The system of claim 1, wherein the at least one remote device is further operable to use an image of a user to estimate a gender, an age, a body mass index (BMI) for the user, and/or detect an emotion from a facial expression in the image of the user.

9. The system of claim 1, wherein the at least one body sensor and the at least one remote device are in real-time two-way communication.

10. A system to reduce stress and promote sleep comprising:
    at least one remote device;
    at least one remote server; and
    at least one body sensor;
    wherein the at least one remote device is in network communication with the at least one remote server, and the at least one body sensor;
    wherein the at least one remote server collects body sensor data from the at least one body sensor;
    wherein the at least one remote server is operable to estimate sleep stages from the body sensor data;
    wherein the at least one remote server is operable to run at least one algorithm to suggest at least one intervention to a user to reduce stress and/or promote sleep based on a user profile, the body sensor data, and/or user provided information;
    wherein the at least one intervention includes automatically adjusting a temperature of a sleeping surface using a mattress, a mattress pad, and/or a blanket, and
    wherein the at least one remote server is operable to adjust parameters of the system based on a comparison of predicted values generated by a virtual model and optimized values generated by a simulation engine.

11. The system of claim 10, the system further comprising at least one environmental sensor comprising a temperature sensor, a humidity sensor, a noise sensor, an air quality sensor, a light sensor, a motion sensor, a barometric sensor, and/or a camera.

12. The system of claim 11, wherein the at least one remote device is in real-time two-way communication with the at least one body sensor and/or the at least one environmental sensor.

13. The system of claim 10, further comprising a mattress with adjustable firmness and/or elevation, an alarm clock, a humidifier, a dehumidifier, a pulsed electromagnetic field device, a transcutaneous electrical nerve stimulation device, a sound generator, an air purifier, a scent generator, red and/or infrared lighting, a lighting system, a fan, a sunrise simulator, and/or a sunset simulator.

14. The system of claim 10, wherein the at least one remote device is operable to recognize an emotion and/or classify at least one health state or condition based on a voice sample from a user.

15. The system of claim 10, wherein a camera on the at least one remote device is operable to scan a room and/or a sleeping environment, and wherein the at least one remote device is operable to provide feedback to a user and/or suggest at least one intervention or at least one change to the room and/or the sleeping environment to reduce stress and/or promote sleep.

16. A system to reduce stress and promote sleep comprising:
- at least one remote device;
- at least one remote server;
- at least one body sensor; and
- at least one environmental sensor;
- wherein the at least one remote device is in network communication with the at least one remote server, the at least one body sensor, and the at least one environmental sensor;
- wherein the at least one remote server collects body sensor data from the at least one body sensor and environmental sensor data from the at least one environmental sensor;
- wherein the at least one remote server is operable to estimate sleep stages from the body sensor data;
- wherein the at least one remote server is operable to run at least one algorithm to suggest at least one intervention to a user to reduce stress and/or promote sleep based on a user profile, the body sensor data, and/or user provided information;
- wherein the at least one intervention includes automatically adjusting a temperature of a sleeping surface using a mattress, a mattress pad, and/or a blanket, and
- wherein the at least one remote server is operable to adjust parameters of the system based on a comparison of predicted values generated by a virtual model and optimized values generated by a simulation engine.

* * * * *